United States Patent
Foster et al.

(10) Patent No.: US 11,541,124 B2
(45) Date of Patent: Jan. 3, 2023

(54) BIOLOGICALLY ACTIVE COMPOUND CONJUGATED TO A STAPLED OR STITCHED PEPTIDE

(71) Applicant: Sutura Therapeutics Ltd, Providenciales (TC)

(72) Inventors: Keith Foster, Camberley (GB); Wouter Eilers, Reading (GB); Adam James Reginald Gadd, Reading (GB)

(73) Assignee: SUTURA THERAPEUTICS LTD, Providenciales (TC)

( * ) Notice: Subject to any disclaimer, the term of this patent is extended or adjusted under 35 U.S.C. 154(b) by 158 days.

(21) Appl. No.: 16/061,548

(22) PCT Filed: Dec. 21, 2016

(86) PCT No.: PCT/GB2016/054028
§ 371 (c)(1),
(2) Date: Jun. 12, 2018

(87) PCT Pub. No.: WO2017/109494
PCT Pub. Date: Jun. 29, 2017

(65) Prior Publication Data
US 2020/0353092 A1    Nov. 12, 2020

(30) Foreign Application Priority Data
Dec. 21, 2015   (GB) ........................... 1522548

(51) Int. Cl.
| | | |
|---|---|---|
| A61K 47/64 | (2017.01) | |
| A61K 48/00 | (2006.01) | |
| A61P 21/00 | (2006.01) | |
| C07K 1/107 | (2006.01) | |
| A61K 47/65 | (2017.01) | |
| C07K 7/02 | (2006.01) | |
| C07K 19/00 | (2006.01) | |
| C07C 13/00 | (2006.01) | |

(52) U.S. Cl.
CPC .............. *A61K 47/65* (2017.08); *A61K 47/64* (2017.08); *A61K 48/005* (2013.01); *A61K 48/0075* (2013.01); *A61P 21/00* (2018.01); *C07C 13/00* (2013.01); *C07K 7/02* (2013.01); *C07K 19/00* (2013.01)

(58) Field of Classification Search
CPC combination set(s) only.
See application file for complete search history.

(56) References Cited

U.S. PATENT DOCUMENTS

2022/0062431 A1   3/2022   Foster et al.

FOREIGN PATENT DOCUMENTS

| CN | 101790385 A | 7/2010 | |
|---|---|---|---|
| CN | 103121959 A | 5/2013 | |
| CN | 103626850 A | 3/2014 | |
| CN | 103998458 A | 8/2014 | |
| JP | 2018521970 A | 8/2018 | |
| WO | WO-1989003849 A1 | 5/1989 | |
| WO | 2009/008725 A2 | 1/2009 | |
| WO | WO-2009054725 A3 | 10/2009 | |
| WO | WO-2009149214 A2 | 12/2009 | |
| WO | WO-2010123369 A1 | 10/2010 | |
| WO | 2011/008260 A2 | 1/2011 | |
| WO | WO-2011008260 A2 * | 1/2011 | .............. A61P 35/04 |
| WO | WO-2011131693 A2 | 10/2011 | |
| WO | 2013/030569 A3 | 3/2013 | |
| WO | WO 2013/150338 A1 | 10/2013 | |
| WO | WO-2013150338 A1 * | 10/2013 | ........... C07K 14/001 |

(Continued)

OTHER PUBLICATIONS

Margus H, Padari K, Pooga M. "Cell-penetrating peptides as versatile vehicles for oligonucleotide delivery." Mol Ther. Mar. 2012;20(3):525-33; Epub Jan. 10, 2012 (Year: 2012).*

(Continued)

*Primary Examiner* — Julie Ha
*Assistant Examiner* — Kristina M Hellman
(74) *Attorney, Agent, or Firm* — Duane Morris LLP; Thomas J. Kowalski; Deborah L. Lu

(57) ABSTRACT

The invention relates to improvements in drug delivery and more particularly to the use of Cell Penetrating Agents (CPA's) or Cell Penetrating Peptides (CPP's) which have been stabilized by, for example: i) stapling two amino acids to form Stapled CPP's (StaP's) or ii) stitching three or more amino acids to form stitched CPP's (StiP's). These stabilized CPP's are conjugated to a drug or Biologically Active Compound (BAC) directly or via a Bi-Functional Linker (BFL) so that the BAC can be carried through a cell membrane by the CPP. The resulting molecules are referred to as Drug Carrying Cell Penetrating Molecules (DCCPM's). The preferred BAC is an electrically low charge carrying oligonucleotide such as a phosphorodiamidate morpholino oligonucleotide (PMO). The invention also relates to a method of facilitating the uptake of a BAC into a cell, the use of a DCCPM in the treatment of a disease requiring alteration of an endogenous or exogenous gene, a method of improving the bioavailability of a drug or BAC, a method of introducing a drug or BAC to a site which is refractory to the drug or BAC in its native state, a method of treating a subject comprising administering the DCCPM's of the invention and to a pharmaceutical composition comprising the DCCPM and one or more pharmaceutically acceptable excipients.

30 Claims, 44 Drawing Sheets
Specification includes a Sequence Listing.

(56) References Cited

FOREIGN PATENT DOCUMENTS

| WO | WO-2014053622 A1 | 4/2014 |
|---|---|---|
| WO | WO-2014064258 A1 | 5/2014 |
| WO | 2014/161284 A1 | 10/2014 |
| WO | WO 2016/187425 A | 11/2016 |
| WO | WO-2016187425 A1 | 11/2016 |
| WO | WO-2017011820 A2 | 1/2017 |
| WO | WO-2017109494 A1 | 6/2017 |
| WO | WO-2019002875 A1 | 1/2019 |

OTHER PUBLICATIONS

Munyendo WL, Lv H, Benza-Ingoula H, et al. "Cell penetrating peptides in the delivery of biopharmaceuticals." Biomolecules. 2012; 2(2):187-202. Published Mar. 3, 20120 (Year: 2012).*
SMCC, PubChem accessed Aug. 28, 2021 at URL: pubchem.ncbi.nlm.nih.gov/compound/125175, pp. 1-25 (2021) (Year: 2021).*
DSG, PubChem accessed Aug. 28, 2021 at URL: pubchem.ncbi.nlm.nih.gov/compound/4432628, pp. 1-15 (2021) (Year: 2021).*
Kim et al., Synthesis of all-hydrocarbon stapled a-helical peptides by ring-closing olefin metathesis, Nature Protocols 6: 761-771 (2011) (Year: 2011).*
Walensky et al., Hydrocarbon-Stapled Peptides: Principles, Practice, and Progress, J. Med. Chem. 57:6275-6288 (epub Feb. 2014) (Year: 2014).*
Moulton et al., "Cellular Uptake of Antisense Morpholino Oligomers Conjugated to Arginine-Rich Peptides," Bioconjugate Chem. 15: 290-299 (2004) (Year: 2004).*
Lebleu et al., "Cell penetrating peptide conjugates of steric block oligonucleotides," Advanced Drug Delivery Reviews 60:517-529 (2008) (Year: 2008).*
Moulton et al., "Morpholinos and their peptide conjugates: Therapeutic promise and challenge for Duchenne muscular dystrophy," Biochimica et Biophysics Acta 1798: 2296-2303 (2010) (Year: 2010).*
Archavala-Gomeza et al., "Comparative Analysis of Antisense Oligonucleotide Sequences for Targeted Skipping of Exon 51 During Dystrophin Pre-mRNA Splicing in Human Muscle," Human Gene Therapy 18:798-810 (2007) (Year: 2007).*
PCT/GB2016/054028, Mar. 24, 2017, International Search Reprt and Written Opinion.
PCT/GB2016/054028, Jul. 5, 2018, International Preliminary Report on Patentability.
Helinski et al., Stitched α-helical peptides via bis ring-closing metathesis. J Am Chem Soc. Sep. 3, 2014;136(35):12314-22. doi: 10.1021/ja505141j. Epub Aug. 21, 2014. Erratum in: J Am Chem Soc. Jul. 15, 2015;137(27):8858.
Kozlov et al., Efficient strategies for the conjugation of oligonucleotides to antibodies enabling highly sensitive protein detection. Biopolymers. Apr. 5, 2004;73(5):621-30. doi: 10.1002/bip.20009.
Aartsma-Rus, et al., "Therapeutic antisense-induced exon skipping in cultured muscle cells from six different DMD patients". Human Molecular Genetics (Apr. 15, 2003); 12(8): 907-914.
Agrawal, et al., "Site-specific excision from RNA by RNase H and mixed-phosphate-backbone oligodeoxynucleotides". Proceedings of the National Academy of Sciences (Feb. 1, 1990); 87(4): 1401-1405.
Alter, et al., "Systemic delivery of morpholino oligonucleotide restores dystrophin expression bodywide and improves dystrophic pathology". Nature Medicine (Feb. 2006); 12(2): 175-177.
Andaloussi, et al., "Use of cell-penetrating-peptides in oligonucleotide splice switching therapy". Current Gene Therapy (Jun. 1, 2012); 12(3): 161-178.
Balraju, et al., "Synthesis of conformationally constrained cyclic peptides using an intramolecular Sonogashira coupling." The Journal of Organic Chemistry (Nov. 11, 2005); 70(23): 9626-9628.
Bendifallah, et al., "Evaluation of cell-penetrating peptides (CPPs) as vehicles for intracellular delivery of antisense peptide nucleic acid (PNA)". Bioconjugate Chemistry (May 17, 2006); 17(3): 750-758.

Betts and Wood, "Cell penetrating peptide delivery of splice directing oligonucleotides as a treatment for Duchenne muscular dystrophy". Current Pharmaceutical Design (May 1, 2013); 19(16): 2948-2462.
Betts, et al., "Pip6-PMO, a new generation of peptide-oligonucleotide conjugates with improved cardiac exon skipping activity for DMD treatment". Molecular Therapy-Nucleic Acids (Aug. 1, 2012); 1:e38, 13 pages.
Bracken, et al., "Synthesis and Nuclear Magnetic Resonance Structure Determination of an. alpha.-Helical, Bicyclic, Lactam-Bridged Hexapeptide". Journal of the American Chemical Society (Jul. 1994); 116(14): 6431-6432.
Campbell, et al., "Oligodeoxynucleoside phosphorothioate stability in subcellular extracts, culture media, sera and cerebrospinal fluid". Journal of Biochemical and Biophysical Methods (Mar. 1, 1990); 20(3): 259-267.
Cantel, et al., "Synthesis and conformational analysis of a cyclic peptide obtained via i to i+ 4 intramolecular side-chain to side-chain azide- alkyne 1, 3-dipolar cycloaddition". The Journal of Organic Chemistry (Aug. 1, 2008); 73(15): 5663-5674.
Chang, et al., "Stapled a- helical peptide drug development: A potent dual inhibitor of MDM2 and MDMX for p53-dependent cancer therapy". Proceedings of the National Academy of Sciences (Sep. 3, 2013); 110(36): E3445-E3454.
Chiriboga, et al., "Results from a phase 1 study of nusinersen (ISIS-SMNRx) in children with spinal muscular atrophy". Neurology (Mar. 8, 2016); 86(10): 890-897.
Chu, Qian, I., "Targeted β-catenin Ubiquitination and Degradation Using Bifunctional Stapled Peptides II. Studies on Cell Penetration by Stapled Peptides". Doctoral Dissertation, Harvard University, Nov. 2013, pp. 1-153, 169 pages.
Cirak, et al., "Exon skipping and dystrophin restoration in patients with Duchenne muscular dystrophy after systemic phosphorodiamidate morpholino oligomer treatment: an open-label, phase 2, dose-escalation study". The Lancet (Aug. 13, 2011); 378(9791): 595-605. Epub Jul. 23, 2011.
Derossi, D. et al. (Apr. 8, 1994) "The Third Helix of the Antennapedia Homeodomain Translocates through Biological Membranes" J Biol Chem, 269(14):10444-10450.
Dirin, et al., "Influence of diverse chemical modifications on the ADME characteristics and toxicology of antisense oligonucleotides". Expert Opinion on Biological Therapy (Jun. 1, 2013); 13(6): 875-888. Epub Mar. 2, 2013.
Ferlini, et al., "T.I.2 Exon skipping and PRO044 in Duchenne muscular dystrophy: Extending the program". Abstracts / Neuromuscular Disorders (2013); 23: Abstract T.I.2, p. 847.
Gautam, et al., "CPPsite: a curated database of cell penetrating peptides". Database. (Jan. 1, 2012); Article IDS bas015, pp. 1-7.
Goemans, et al., "A randomized placebo-controlled phase 3 trial of an antisense oligonucleotide, drisapersen, in Duchenne muscular dystrophy". Neuromuscular Disorders (Jan. 1, 2018); 28(1): 4-15, 12 pages. Epub Dec. 6, 2017.
Goemans, et al., "Long-term efficacy, safety, and pharmacokinetics of drisapersen in Duchenne muscular dystrophy: results from an open-label extension study". PLoS One (Sep. 2, 2016); 11(9): e0161955, 20 pages.
Goemans, et al., "P.7.1 A prospective natural history study of the progression of physical impairment, activity limitation, and quality of life in Duchenne muscular dystrophy". Neuromuscular Disorders (2013); 23(9-10): 773.
Heald, et al., "Safety and pharmacokinetic profiles of phosphorodiamidate morpholino oligomers with activity against ebola virus and marburg virus: results of two single-ascending-dose studies". Antimicrobial Agents and Chemotherapy (Nov. 2014); 58(11): 6639-6647.
Heemskerk, et al., "In vivo comparison of 2'-O-methyl phosphorothioate and morpholino antisense oligonucleotides for Duchenne muscular dystrophy exon skipping". The Journal Of Gene Medicine: A Cross-Disciplinary Journal for Research on the Science of Gene Transfer and Its Clinical Applications (Mar. 2009); 11(3): 257-266.
Hirose, et al., "Transient focal membrane deformation induced by arginine-rich peptides leads to their direct penetration into cells". Molecular Therapy (May 1, 2012); 20(5): 984-993.

(56) References Cited

OTHER PUBLICATIONS

Hoffman, et al., "Dystrophin: the protein product of the Duchenne muscular dystrophy locus". Cell (Dec. 24, 1987); 51(6): 919-928.
International Preliminary Report on Patentability in International Application No. PCT/GB2016/054028 dated Jun. 26, 2018, 9 pages.
International Preliminary Report on Patentability in International Application No. PCT/GB2018/051818 dated Oct. 1, 2019, 19 pages.
International Search Report and Written Opinion in International Application No. PCT/GB2016/054028 dated Mar. 24, 2017, 13 pages.
International Search Report and Written Opinion in International Application No. PCT/GB2018/051818 dated Nov. 2, 2018, 16 pages.
Ivanova, et al., "Improved cell-penetrating peptide-PNA conjugates for splicing redirection in HeLa cells and exon skipping in mdx mouse muscle". Nucleic Acids Research (Nov. 1, 2008); 36(20): 6418-6428. Epub Oct. 8, 2008.
Iversen, et al., "Discovery and early development of AVI-7537 and AVI-7288 for the treatment of Ebola virus and Marburg virus infections". Viruses (Nov. 2012); 4(11): 2806-2830.
Jearawiriyapaisarn, et al., "Long-term improvement in mdx cardiomyopathy after therapy with peptide-conjugated morpholino oligomers". Cardiovascular Research (Feb. 1, 2010); 85(3): 444-453. Epub Oct. 8, 2009.
Jearawiriyapaisarn, et al., "Sustained dystrophin expression induced by peptide-conjugated morpholino oligomers in the muscles of mdx mice". Molecular Therapy (Sep. 1, 2008); 16(9): 1624-1629. Epub Jun. 10, 2008.
Kinali, et al., "Local restoration of dystrophin expression with the morpholino oligomer AVI-4658 in Duchenne muscular dystrophy: a single-blind, placebo-controlled, dose-escalation, proof-of-concept study". The Lancet Neurology (Oct. 1, 2009); 8(10): 918-928.
Kreutz, et al., "Antibody-antigen-adjuvant conjugates enable co-delivery of antigen and adjuvant to dendritic cells in cis but only have partial targeting specificity". PLoS One (Jul. 10, 2012); 7(7): e40208, 12 pages. Epub Jul. 10, 2012.
Lau, et al., "Peptide stapling techniques based on different macrocyclisation chemistries". Chemical Society Reviews (Sep. 8, 2015); 44(1): 91-102. Epub Sep. 8, 2014.
Lautrette, et al., "Nitrogen arylation for macrocyclization of unprotected peptides". Journal of the American Chemical Society (Jul. 13, 2016); 138(27): 8340-8343. Epub Jun. 30, 2016.
Lehto, et al., Cellular trafficking determines the exon skipping activity of Pip6a-PMO in mdx skeletal and cardiac muscle cells. Nucleic Acids Research (Mar. 1, 2014); 42(5): 3207-32017. Epub Dec. 23, 2013.
Lu, et al., "Systemic delivery of antisense oligoribonucleotide restores dystrophin expression in body-wide skeletal muscles". Proceedings of the National Academy of Sciences (Jan. 4, 2005); 102(1): 198-203.
Melacini, et al., "Multiconformational NMR analysis of sandostatin (octreotide): Equilibrium between β-sheet and partially helical structures". Biochemistry (Feb. 11, 1997); 36(6): 1233-1241.
Mendell, et al., Eteplirsen for the treatment of Duchenne muscular dystrophy. Annals of Neurology (Nov. 2013); 74(5): 637-647. Epub Sep. 10, 2013.
Mendell, et al., "Evidence-based path to newborn screening for Duchenne muscular dystrophy". Annals of Neurology (Mar. 2012); 71(3): 304-313.
Mier, et al., "Peptide-PNA conjugates: Targeted transport of antisense therapeutics into tumors". Angewandte Chemie International Edition (Apr. 29, 2003); 42(17): 1968-1971.
Ming Yang, Molecular Recognition in Pharmaceutical Research, Peking Union Medical College Press (Mar. 1999); pp. 88-90, and Machine translation, 9 pages.

Monaco, et al., "An explanation for the phenotypic differences between patients bearing partial deletions of the DMD locus". Genomics (Jan. 1, 1988); 2(1): 90-95.
Moulton, et al., "Morpholinos and their peptide conjugates: therapeutic promise and challenge for Duchenne muscular dystrophy". Biochimica et Biophysica Acta (BBA)-Biomembranes (Dec. 1, 2010); 1798(12): 2296-2303. Epub Feb. 17, 2010.
Nakase, et al., "Interaction of arginine-rich peptides with membrane-associated proteoglycans is crucial for induction of actin organization and macropinocytosis". Biochemistry (Jan. 16, 2007); 46(2): 492-501.
Sazani, et al.. "Safety pharmacology and genotoxicity evaluation of AVI-4658". International Journal of Toxicology (Mar. 2010); 29(2): 143-156. Epub Jan. 28, 2010.
Sazani, et al., "Repeat-dose toxicology evaluation in cynomolgus monkeys of AVI-4658, a phosphorodiamidate morpholino oligomer (PMO) drug for the treatment of duchenne muscular dystrophy". International Journal of Toxicology (May 2011); 30(3): 313-321. Epub May 3, 2011.
Shibahara, et al., "Inhibition of human immunodeficiency virus (HIV-1) replication by synthetic oligo-RNA derivatives". Nucleic Acids Research (Jan. 11, 1989); 17(1): 239-252.
Tereshko, et al., "Correlating structure and stability of DNA duplexes with incorporated 2 '-O-modified RNA analogues". Biochemistry (Jul. 28, 1998); 37(30): 10626-10634.
Tünnemann, et al., "Live-cell analysis of cell penetration ability and toxicity of oligo-arginines". Journal of Peptide Science: An Official Publication of the European Peptide Society (Apr. 2008); 14(4): 469-476.
U.S. Appl. No. 16/626,476 for Compounds Comprising Stapled or Stitched Peptides for Improved Drug Delivery, filed Jun. 28, 2018.
Van Deutekom, et al., "Local dystrophin restoration with antisense oligonucleotide PRO051". New England Journal of Medicine (Dec. 27, 2007); 357(26): 2677-2686.
Venkatesan and Kim, "Peptide conjugates of oligonucleotides: synthesis and applications". Chemical Reviews (Sep. 13, 2006); 106(9): 3712-3761.
Vitiello, et al., "In vivo delivery of naked antisense oligos in aged mdx mice: analysis of dystrophin restoration in skeletal and cardiac muscle". Neuromuscular Disorders (Aug. 1, 2008); 18(8): 597-605. Epub Jul. 3, 2008.
Wang and Chou, "A thiol-ene coupling approach to native peptide stapling and macrocyclization". Angewandte Chemie International Edition (Sep. 7, 2015); 54(37): 10931-10934. Epub Jul. 17, 2015.
Warren, et al., "Advanced antisense therapies for postexposure protection against lethal filovirus infections". Nature Medicine (Sep. 2010); 16(9): 991-994. Epub Aug. 22, 2010.
Williams and Chaput, "Synthesis of peptide-oligonucleotide conjugates using a heterobifunctional crosslinker". In: Current Protocols in Nucleic acid Chemistry (Sep. 2010); 42(1): Unit 4.41, pp. 4.41.1-4.41.20, ISBN: 978-0-471-14270-6.
Wu, B., et al., "Dose-dependent restoration of dystrophin expression in cardiac muscle of dystrophic mice by systemically delivered morpholino". Gene Therapy (Jan. 2010); 17(1): 132-140.
Wu, B., et al., "Effective rescue of dystrophin improves cardiac function in dystrophin-deficient mice by a modified morpholino oligomer". Proceedings of the National Academy of Sciences (Sep. 30, 2008); 105(39): 14814-148149. Epub Sep. 19, 2008.
Wu, et al., "One-year treatment of morpholino antisense oligomer improves skeletal and cardiac muscle functions in dystrophic mdx mice". Molecular Therapy (Mar. 1, 2011); 19(3): 576-583. Epub Dec. 21, 2010.
Xiaoliang Wang, Applied Molecular Pharmacology, Peking Union Medical College Press (Sep. 2015); pp. 533-535, and Machine translation, 8 pages.
Chu, Qian. "Towards Understanding Cell Penetration by Stapled Peptides." Med. Chem. Commun., 2015, 6, pp. 111-119.

* cited by examiner

Non-Cyclised peptide → RCM i,i+4

RCM i,i+4 → Reduced RCM i,i+4

Compound VI

PMO*

PMO-CP8M*

1 μmol/kg

PMO*

PMO-CP8M*

7.6 μmol/kg

PMO

PMO-CP8M 10.9 μmol/kg

SEQUENCE LISTING

```
<160> NUMBER OF SEQ ID NOS: 193

<210> SEQ ID NO 1
<211> LENGTH: 25
<212> TYPE: DNA
<213> ORGANISM: Homo sapiens

<400> SEQUENCE: 1
ggccaaacct cggcttacct gaaat                                                25

<210> SEQ ID NO 2
<211> LENGTH: 30
<212> TYPE: RNA
<213> ORGANISM: Homo sapiens

<400> SEQUENCE: 2
cuccaacauc aaggaagaug gcauuucuag                                           30

<210> SEQ ID NO 3
<211> LENGTH: 18
<212> TYPE: PRT
<213> ORGANISM: Artificial Sequence
<220> FEATURE:
<223> OTHER INFORMATION: Synthetic

<400> SEQUENCE: 3

Thr Arg Gln Ala Arg Arg Asn Arg Arg Arg Trp Arg Arg Ala Ala
1               5                   10                  15

Ala Ala

<210> SEQ ID NO 4
<211> LENGTH: 17
<212> TYPE: PRT
<213> ORGANISM: Artificial Sequence
<220> FEATURE:
<223> OTHER INFORMATION: Synthetic

<400> SEQUENCE: 4

Thr Arg Gln Ala Arg Arg Asn Arg Arg Arg Trp Arg Glu Arg Gln
1               5                   10                  15

Arg

<210> SEQ ID NO 5
<211> LENGTH: 16
<212> TYPE: PRT
```

```
<213> ORGANISM: Artificial Sequence
<220> FEATURE:
<223> OTHER INFORMATION: Synthetic

<400> SEQUENCE: 5

Arg Gln Ile Lys Ile Trp Phe Gln Asn Arg Arg Met Lys Trp Lys Lys
1               5                   10                  15

<210> SEQ ID NO 6
<211> LENGTH: 12
<212> TYPE: PRT
<213> ORGANISM: Artificial Sequence
<220> FEATURE:
<223> OTHER INFORMATION: Synthetic

<400> SEQUENCE: 6

Arg Arg Arg Arg Arg Arg Arg Arg Trp Arg Arg Arg
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Synthetic

<400> SEQUENCE: 7

Leu Ser Gln Glu Thr Phe Ser Asp Leu Trp Lys Leu Leu Pro Glu Asn
1               5                   10                  15

<210> SEQ ID NO 8
<211> LENGTH: 14
<212> TYPE: PRT
<213> ORGANISM: Artificial Sequence
<220> FEATURE:
<223> OTHER INFORMATION: Synthetic

<400> SEQUENCE: 8

Asn Gln Leu Lys Arg Ser Phe Phe Ala Leu Arg Asp Gln Ile
1               5                   10

<210> SEQ ID NO 9
<211> LENGTH: 23
<212> TYPE: PRT
<213> ORGANISM: Artificial Sequence
<220> FEATURE:
<223> OTHER INFORMATION: Synthetic

<400> SEQUENCE: 9

Thr Ile Leu Lys Ala Ser Val Asp Tyr Ile Arg Lys Leu Gln Arg Glu
1               5                   10                  15

Gln Gln Arg Ala Lys Glu Leu
            20

<210> SEQ ID NO 10
<211> LENGTH: 12
<212> TYPE: PRT
<213> ORGANISM: Artificial Sequence
<220> FEATURE:
<223> OTHER INFORMATION: Synthetic

<400> SEQUENCE: 10

Arg Arg Arg Arg Arg Arg Arg Arg Arg Arg Arg Arg
1               5                   10

<210> SEQ ID NO 11
```

-continued

```
<211> LENGTH: 12
<212> TYPE: PRT
<213> ORGANISM: Artificial Sequence
<220> FEATURE:
<223> OTHER INFORMATION: Synthetic

<400> SEQUENCE: 11

Tyr Gly Arg Lys Lys Arg Arg Gln Arg Arg Pro
1               5                   10

<210> SEQ ID NO 12
<211> LENGTH: 8
<212> TYPE: PRT
<213> ORGANISM: Artificial Sequence
<220> FEATURE:
<223> OTHER INFORMATION: Synthetic

<400> SEQUENCE: 12

Arg Lys Phe Lys Arg Leu Phe Gln
1               5

<210> SEQ ID NO 13
<211> LENGTH: 14
<212> TYPE: PRT
<213> ORGANISM: Artificial Sequence
<220> FEATURE:
<223> OTHER INFORMATION: Synthetic

<400> SEQUENCE: 13

Asn Glu Leu Lys Arg Ser Phe Phe Ala Leu Arg Asp Gln Ile
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8,
      S-octenylalanine
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain

<400> SEQUENCE: 14

Asn Gln Leu Xaa Arg Ser Phe Phe Ala Leu Xaa Asp Gln Ile
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Synthetic

<400> SEQUENCE: 15

Lys Asn His Thr His Gln Gln Asp Ile
1               5

<210> SEQ ID NO 16
<211> LENGTH: 42
<212> TYPE: PRT
<213> ORGANISM: Artificial Sequence
<220> FEATURE:
```

<223> OTHER INFORMATION: Synthetic

<400> SEQUENCE: 16

Asn Glu Leu Lys Arg Ser Phe Phe Ala Leu Arg Asp Gln Ile Pro Ser
1               5                   10                  15

Leu Gln Gly Glu Lys Ala Ser Arg Ala Gln Ile Leu Asp Lys Ala Thr
            20                  25                  30

Glu Tyr Ile Gln Tyr Asn Leu Arg Arg Lys
        35                  40

<210> SEQ ID NO 17
<211> LENGTH: 24
<212> TYPE: PRT
<213> ORGANISM: Artificial Sequence
<220> FEATURE:
<223> OTHER INFORMATION: Synthetic

<400> SEQUENCE: 17

Lys Ala Thr Glu Tyr Ile Gln Tyr Asn Leu Arg Arg Lys Asn His Thr
1               5                   10                  15

His Gln Gln Asp Ile Asp Asp Leu
            20

<210> SEQ ID NO 18
<211> LENGTH: 15
<212> TYPE: PRT
<213> ORGANISM: Artificial Sequence
<220> FEATURE:
<223> OTHER INFORMATION: Synthetic

<400> SEQUENCE: 18

Ala Ser Thr Leu Phe Glu Thr Phe Tyr Leu Gly Gly Leu Leu Gly
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: Xaa is S5, a-methyl, a-alkenylglycine with 5
      carbon chain
<220> FEATURE:
<221> NAME/KEY: misc_feature
<222> LOCATION: (14)..(14)
<223> OTHER INFORMATION: Xaa is S5, a-methyl, a-alkenylglycine with 5
      carbon chain

<400> SEQUENCE: 19

Arg Arg Gly Ser Arg Pro Ser Gly Ala Xaa Arg Arg Arg Xaa Arg
1               5                   10                  15

<210> SEQ ID NO 20
<211> LENGTH: 14
<212> TYPE: PRT
<213> ORGANISM: Artificial Sequence
<220> FEATURE:
<223> OTHER INFORMATION: Synthetic

<400> SEQUENCE: 20

Phe Asn Ile Asn Asp Arg Ile Lys Glu Leu Gly Thr Leu Ile
1               5                   10

```
<210> SEQ ID NO 21
<211> LENGTH: 42
<212> TYPE: PRT
<213> ORGANISM: Artificial Sequence
<220> FEATURE:
<223> OTHER INFORMATION: Synthetic

<400> SEQUENCE: 21

Asp His Ile Lys Asp Ser Phe His Ser Leu Arg Asp Ser Val Pro Ser
1               5                   10                  15

Leu Gln Gly Glu Lys Ala Ser Arg Ala Gln Ile Leu Asp Lys Ala Thr
            20                  25                  30

Glu Tyr Ile Gln Tyr Asn Leu Arg Arg Lys
        35                  40

<210> SEQ ID NO 22
<211> LENGTH: 36
<212> TYPE: PRT
<213> ORGANISM: Artificial Sequence
<220> FEATURE:
<223> OTHER INFORMATION: Synthetic

<400> SEQUENCE: 22

Glu Tyr Ile Gln Tyr Asn Leu Arg Lys Asn His Thr His Gln Gln Asp
1               5                   10                  15

Ile Asp Asp Leu Lys Arg Gln Asn Ala Leu Leu Glu Gln Gln Val Arg
            20                  25                  30

Ala Leu Gly Gly
        35

<210> SEQ ID NO 23
<211> LENGTH: 16
<212> TYPE: PRT
<213> ORGANISM: Artificial Sequence
<220> FEATURE:
<223> OTHER INFORMATION: Synthetic

<400> SEQUENCE: 23

Ser Ser Leu Phe Glu Arg Phe Tyr Asn Leu Val Thr Pro Ala Gly Gly
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Synthetic

<400> SEQUENCE: 24

Asn Ser Ser Phe Ala Asp Phe Phe His Thr Val Pro Tyr Asn Leu Leu
1               5                   10                  15

<210> SEQ ID NO 25
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
```

-continued carbon chain

<400> SEQUENCE: 25

Thr Arg Gln Ala Arg Arg Asn Xaa Arg Arg Arg Xaa Arg Arg
1               5                   10

<210> SEQ ID NO 26
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: Xaa is S5, a-methyl, a-alkenylglycine with 5
      carbon chain
<220> FEATURE:
<221> NAME/KEY: misc_feature
<222> LOCATION: (14)..(14)
<223> OTHER INFORMATION: Xaa is S5, a-methyl, a-alkenylglycine with 5
      carbon chain

<400> SEQUENCE: 26

Arg Arg Gly Ser Arg Pro Ser Gly Ala Xaa Arg Arg Arg Xaa Arg Ala
1               5                   10                  15

Ala Ala Ala

<210> SEQ ID NO 27
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is S5, a-methyl, a-alkenylglycine with 5
      carbon chain
<220> FEATURE:
<221> NAME/KEY: misc_feature
<222> LOCATION: (5)..(5)
<223> OTHER INFORMATION: Xaa is S5, a-methyl, a-alkenylglycine with 5
      carbon chain

<400> SEQUENCE: 27

Xaa Arg Arg Gln Xaa Arg Arg Asp Arg Gln Arg Arg Arg Arg Arg
1               5                   10                  15

<210> SEQ ID NO 28
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain

<400> SEQUENCE: 28

Thr Arg Gln Xaa Arg Arg Gln Xaa Arg Arg Arg Trp Arg Glu Arg Gln
1               5                   10                  15

Arg

```
<210> SEQ ID NO 29
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa is S5, a-methyl, a-alkenylglycine with 5
      carbon chain
<220> FEATURE:
<221> NAME/KEY: misc_feature
<222> LOCATION: (10)..(10)
<223> OTHER INFORMATION: Xaa is S5, a-methyl, a-alkenylglycine with 5
      carbon chain

<400> SEQUENCE: 29

Ser Glu Glu Leu Val Xaa Glu Ala His Xaa Leu Cys Thr Leu Leu Glu
1               5                   10                  15

Asn Ala Ile Gln Asp Thr Val Arg Glu Gln
            20                  25

<210> SEQ ID NO 30
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: Xaa is S5, a-methyl, a-alkenylglycine with 5
      carbon chain
<220> FEATURE:
<221> NAME/KEY: misc_feature
<222> LOCATION: (14)..(14)
<223> OTHER INFORMATION: Xaa is S5, a-methyl, a-alkenylglycine with 5
      carbon chain

<400> SEQUENCE: 30

Ser Glu Glu Leu Val Ala Glu Ala His Xaa Leu Cys Thr Xaa Leu Glu
1               5                   10                  15

Asn Ala Ile Gln Asp Thr Val Arg Glu Gln
            20                  25

<210> SEQ ID NO 31
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: Xaa is S5, a-methyl, a-alkenylglycine with 5
      carbon chain
<220> FEATURE:
<221> NAME/KEY: misc_feature
<222> LOCATION: (21)..(21)
<223> OTHER INFORMATION: Xaa is S5, a-methyl, a-alkenylglycine with 5
      carbon chain

<400> SEQUENCE: 31

Ser Glu Glu Leu Val Ala Glu Ala His Asn Leu Cys Thr Leu Leu Glu
1               5                   10                  15

Xaa Ala Ile Gln Xaa Thr Val Arg Glu Gln
            20                  25
```

```
<210> SEQ ID NO 32
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain

<400> SEQUENCE: 32

Asp Arg Arg Gln Arg Arg Arg Xaa Arg Gln Arg Xaa Arg Arg Arg
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is S5, a-methyl, a-alkenylglycine with 5
      carbon chain
<220> FEATURE:
<221> NAME/KEY: misc_feature
<222> LOCATION: (5)..(5)
<223> OTHER INFORMATION: Xaa is S5, a-methyl, a-alkenylglycine with 5
      carbon chain

<400> SEQUENCE: 33

Xaa Arg Arg Gln Xaa Arg Arg Arg Arg Gln Arg Arg Arg Arg Arg
1               5                   10                  15

<210> SEQ ID NO 34
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa is S5, a-methyl, a-alkenylglycine with 5
      carbon chain
<220> FEATURE:
<221> NAME/KEY: misc_feature
<222> LOCATION: (6)..(6)
<223> OTHER INFORMATION: Xaa is S5, a-methyl, a-alkenylglycine with 5
      carbon chain

<400> SEQUENCE: 34

Ser Xaa Glu Leu Val Xaa Glu Ala His Asn Leu Cys Thr Leu Leu Glu
1               5                   10                  15

Asn Ala Ile Gln Asp Thr Val Arg Glu Gln
            20                  25

<210> SEQ ID NO 35
<211> LENGTH: 26
<212> TYPE: PRT
<213> ORGANISM: Artificial Sequence
<220> FEATURE:
<223> OTHER INFORMATION: Synthetic
```

-continued

```
<220> FEATURE:
<221> NAME/KEY: misc_feature
<222> LOCATION: (9)..(9)
<223> OTHER INFORMATION: Xaa is S5, a-methyl, a-alkenylglycine with 5
      carbon chain
<220> FEATURE:
<221> NAME/KEY: misc_feature
<222> LOCATION: (13)..(13)
<223> OTHER INFORMATION: Xaa is S5, a-methyl, a-alkenylglycine with 5
      carbon chain

<400> SEQUENCE: 35

Ser Glu Glu Leu Val Ala Glu Ala Xaa Asn Leu Cys Xaa Leu Leu Glu
1               5                   10                  15

Asn Ala Ile Gln Asp Thr Val Arg Glu Gln
            20                  25

<210> SEQ ID NO 36
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(13)
<223> OTHER INFORMATION: Xaa is S5, a-methyl, a-alkenylglycine with 5
      carbon chain
<220> FEATURE:
<221> NAME/KEY: misc_feature
<222> LOCATION: (17)..(17)
<223> OTHER INFORMATION: Xaa is S5, a-methyl, a-alkenylglycine with 5
      carbon chain

<400> SEQUENCE: 36

Ser Glu Glu Leu Val Ala Glu Ala His Asn Leu Cys Xaa Leu Leu Glu
1               5                   10                  15

Xaa Ala Ile Gln Asp Thr Val Arg Glu Gln
            20                  25

<210> SEQ ID NO 37
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: Xaa is S5, a-methyl, a-alkenylglycine with 5
      carbon chain
<220> FEATURE:
<221> NAME/KEY: misc_feature
<222> LOCATION: (24)..(24)
<223> OTHER INFORMATION: Xaa is S5, a-methyl, a-alkenylglycine with 5
      carbon chaind

<400> SEQUENCE: 37

Ser Glu Glu Leu Val Ala Glu Ala His Asn Leu Cys Thr Leu Leu Glu
1               5                   10                  15

Asn Ala Ile Xaa Asp Thr Val Xaa Glu Gln
            20                  25

<210> SEQ ID NO 38
<211> LENGTH: 8
<212> TYPE: PRT
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (3)..(3)
<223> OTHER INFORMATION: Xaa is S5, a-methyl, a-alkenylglycine with 5
      carbon chain
<220> FEATURE:
<221> NAME/KEY: misc_feature
<222> LOCATION: (7)..(7)
<223> OTHER INFORMATION: Xaa is S5, a-methyl, a-alkenylglycine with 5
      carbon chain

<400> SEQUENCE: 38

Phe Ser Xaa Leu Trp Lys Xaa Leu
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is S5, a-methyl, a-alkenylglycine with 5
      carbon chain
<220> FEATURE:
<221> NAME/KEY: misc_feature
<222> LOCATION: (7)..(7)
<223> OTHER INFORMATION: Xaa is S5, a-methyl, a-alkenylglycine with 5
      carbon chain

<400> SEQUENCE: 39

Phe Met Xaa Tyr Trp Lys Xaa Leu
1               5

<210> SEQ ID NO 40
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa is S5, a-methyl, a-alkenylglycine with 5
      carbon chain
<220> FEATURE:
<221> NAME/KEY: misc_feature
<222> LOCATION: (9)..(9)
<223> OTHER INFORMATION: Xaa is S5, a-methyl, a-alkenylglycine with 5
      carbon chain

<400> SEQUENCE: 40

Gln Thr Phe Ser Xaa Leu Trp Lys Xaa Leu
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa is S5, a-methyl, a-alkenylglycine with 5
      carbon chain
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain
```

```
<400> SEQUENCE: 41

Pro Pro Lys Lys Phe Arg Xaa Leu Phe Phe Xaa Ser
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is pff, pentafluoro-L-phenylalanine
<220> FEATURE:
<221> NAME/KEY: misc_feature
<222> LOCATION: (5)..(5)
<223> OTHER INFORMATION: Xaa is S5, a-methyl, a-alkenylglycine with 5
      carbon chain
<220> FEATURE:
<221> NAME/KEY: misc_feature
<222> LOCATION: (9)..(9)
<223> OTHER INFORMATION: Xaa is S5, a-methyl, a-alkenylglycine with 5
      carbon chain

<400> SEQUENCE: 42

Lys Lys Xaa Arg Xaa Leu Phe Phe Xaa Ser
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is pff, pentafluoro-L-phenylalanine
<220> FEATURE:
<221> NAME/KEY: misc_feature
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain

<400> SEQUENCE: 43

Arg Lys Xaa Xaa Arg Leu Phe Xaa Ser Tyr
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain

<400> SEQUENCE: 44
```

Arg Lys Phe Xaa Arg Leu Phe Xaa Ser Tyr
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa is pff, pentafluoro-L-phenylalanine
<220> FEATURE:
<221> NAME/KEY: misc_feature
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain

<400> SEQUENCE: 45

Arg Xaa Lys Xaa Arg Leu Phe Xaa Ser Tyr
1               5                   10

<210> SEQ ID NO 46
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is S5, a-methyl, a-alkenylglycine with 5
      carbon chain
<220> FEATURE:
<221> NAME/KEY: misc_feature
<222> LOCATION: (7)..(7)
<223> OTHER INFORMATION: Xaa is S5, a-methyl, a-alkenylglycine with 5
      carbon chain

<400> SEQUENCE: 46

Ala Met Xaa Tyr Trp Lys Xaa Leu
1               5

<210> SEQ ID NO 47
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa is R5, an enantiomer of S5, a-methyl,
      a-alkenylglycine with 5 carbon chain
<220> FEATURE:
<221> NAME/KEY: misc_feature
<222> LOCATION: (9)..(9)
<223> OTHER INFORMATION: Xaa is S5, a-methyl, a-alkenylglycine with 5
      carbon chain

<400> SEQUENCE: 47

Gln Thr Phe Ser Asp Xaa Trp Lys Xaa Leu
1               5                   10

<210> SEQ ID NO 48
<211> LENGTH: 10

```
<212> TYPE: PRT
<213> ORGANISM: Artificial Sequence
<220> FEATURE:
<223> OTHER INFORMATION: Synthetic 220>
<220> FEATURE:
<221> NAME/KEY: misc_feature
<222> LOCATION: (5)..(5)
<223> OTHER INFORMATION: Xaa is S5, a-methyl, a-alkenylglycine with 5
      carbon chain
<220> FEATURE:
<221> NAME/KEY: misc_feature
<222> LOCATION: (9)..(9)
<223> OTHER INFORMATION: Xaa is S5, a-methyl, a-alkenylglycine with 5
      carbon chain

<400> SEQUENCE: 48

Lys Lys Phe Arg Xaa Leu Phe Phe Xaa Ser
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa is is S5, a-methyl, a-alkenylglycine with 5
      carbon chain
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain

<400> SEQUENCE: 49

Arg Arg Leu Phe Arg Xaa Asn Leu Phe Leu Xaa Thr
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is pff, pentafluoro-L-phenylalanine
<220> FEATURE:
<221> NAME/KEY: misc_feature
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain

<400> SEQUENCE: 50

Arg Arg Xaa Xaa Arg Leu Phe Xaa Ser Tyr
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain

<400> SEQUENCE: 51

Arg Lys Ala Xaa Arg Leu Phe Xaa Ser Tyr
1               5                   10

<210> SEQ ID NO 52
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is S5, a-methyl, a-alkenylglycine with 5
      carbon chain
<220> FEATURE:
<221> NAME/KEY: misc_feature
<222> LOCATION: (5)..(5)
<223> OTHER INFORMATION: Xaa is S5, a-methyl, a-alkenylglycine with 5
      carbon chain

<400> SEQUENCE: 52

Xaa Arg Leu Phe Xaa Ser Tyr
1               5

<210> SEQ ID NO 53
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain

<400> SEQUENCE: 53

Lys Gln Lys Arg Lys Phe Ser Xaa Phe Phe Lys Xaa Leu
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa is pff, pentafluoro-L-phenylalanine
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain
<220> FEATURE:
<221> NAME/KEY: misc_feature
<222> LOCATION: (12)..(12)
```

<223> OTHER INFORMATION: Xaa is S5, a-methyl, a-alkenylglycine with 5
      carbon chain

<400> SEQUENCE: 54

Lys Gln Lys Arg Lys Xaa Ser Xaa Phe Phe Lys Xaa Leu
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is S5, a-methyl, a-alkenylglycine with 5
      carbon chain
<220> FEATURE:
<221> NAME/KEY: misc_feature
<222> LOCATION: (7)..(7)
<223> OTHER INFORMATION: Xaa is S5, a-methyl, a-alkenylglycine with 5
      carbon chain

<400> SEQUENCE: 55

Lys Phe Xaa Arg Leu Phe Xaa
1               5

<210> SEQ ID NO 56
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is S5, a-methyl, a-alkenylglycine with 5
      carbon chain
<220> FEATURE:
<221> NAME/KEY: misc_feature
<222> LOCATION: (5)..(5)
<223> OTHER INFORMATION: Xaa is S5, a-methyl, a-alkenylglycine with 5
      carbon chain

<400> SEQUENCE: 56

Xaa Arg Leu Phe Xaa
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain

<400> SEQUENCE: 57

Arg Lys Phe Xaa Arg Leu Phe Xaa
1               5

<210> SEQ ID NO 58

```
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain

<400> SEQUENCE: 58

Lys Gln Lys Arg Lys Phe Ser Xaa Phe Phe Lys Xaa Leu Val
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is pff, pentafluoro-L-phenylalanine
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain

<400> SEQUENCE: 59

Lys Gln Xaa Arg Lys Lys Ser Xaa Phe Phe Lys Xaa Leu
1               5                   10

<210> SEQ ID NO 60
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is pff, pentafluoro-L-phenylalanine
<220> FEATURE:
<221> NAME/KEY: misc_feature
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain

<400> SEQUENCE: 60

Arg Lys Xaa Xaa Arg Leu Phe Xaa
1               5

<210> SEQ ID NO 61
<211> LENGTH: 6
<212> TYPE: PRT
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa is S5, a-methyl, a-alkenylglycine with 5
      carbon chain
<220> FEATURE:
<221> NAME/KEY: misc_feature
<222> LOCATION: (6)..(6)
<223> OTHER INFORMATION: Xaa is S5, a-methyl, a-alkenylglycine with 5
      carbon chain

<400> SEQUENCE: 61

Phe Xaa Arg Leu Phe Xaa
1               5

<210> SEQ ID NO 62
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa is S5, a-methyl, a-alkenylglycine with 5
      carbon chain
<220> FEATURE:
<221> NAME/KEY: misc_feature
<222> LOCATION: (13)..(13)
<223> OTHER INFORMATION: Xaa is S5, a-methyl, a-alkenylglycine with 5
      carbon chain

<400> SEQUENCE: 62

Lys Thr Tyr Arg Gly Ala Phe Gln Xaa Leu Phe Gln Xaa Val Arg Glu
1               5                   10                  15

<210> SEQ ID NO 63
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa is S5, a-methyl, a-alkenylglycine with 5
      carbon chain
<220> FEATURE:
<221> NAME/KEY: misc_feature
<222> LOCATION: (10)..(10)
<223> OTHER INFORMATION: Xaa is S5, a-methyl, a-alkenylglycine with 5
      carbon chain

<400> SEQUENCE: 63

Ser Thr Ala Leu Arg Xaa Leu Ile Glu Xaa Leu Val Asn Ile Thr Gln
1               5                   10                  15

Asn Gln Lys Ala Pro Leu
            20

<210> SEQ ID NO 64
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa is S5, a-methyl, a-alkenylglycine with 5
``` carbon chain
<220> FEATURE:
<221> NAME/KEY: misc_feature
<222> LOCATION: (13)..(13)
<223> OTHER INFORMATION: Xaa is S5, a-methyl, a-alkenylglycine with 5
      carbon chain

<400> SEQUENCE: 64

Ser Thr Ala Leu Arg Glu Leu Ile Xaa Glu Leu Val Xaa Ile Thr Gln
1               5                   10                  15

Asn Gln Lys Ala Pro Leu
            20

<210> SEQ ID NO 65
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain
<220> FEATURE:
<221> NAME/KEY: misc_feature
<222> LOCATION: (16)..(16)
<223> OTHER INFORMATION: Xaa is S5, a-methyl, a-alkenylglycine with 5
      carbon chain

<400> SEQUENCE: 65

Ser Thr Ala Leu Arg Glu Leu Ile Glu Glu Leu Xaa Asn Ile Thr Xaa
1               5                   10                  15

Asn Gln Lys Ala Pro Leu
            20

<210> SEQ ID NO 66
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa is S5, a-methyl, a-alkenylglycine with 5
      carbon chain
<220> FEATURE:
<221> NAME/KEY: misc_feature
<222> LOCATION: (9)..(9)
<223> OTHER INFORMATION: Xaa is S5, a-methyl, a-alkenylglycine with 5
      carbon chain

<400> SEQUENCE: 66

Asn Glu Leu Lys Xaa Ser Phe Phe Xaa Leu Arg Asp Gln Ile Pro Glu
1               5                   10                  15

Leu Glu Asn Asn Glu Lys Ala Pro
            20

<210> SEQ ID NO 67
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa is S5, a-methyl, a-alkenylglycine with 5
      carbon chain

```
<220> FEATURE:
<221> NAME/KEY: misc_feature
<222> LOCATION: (10)..(10)
<223> OTHER INFORMATION: Xaa is S5, a-methyl, a-alkenylglycine with 5
      carbon chain

<400> SEQUENCE: 67

Leu Glu Asn Arg Gln Xaa Lys Leu Glu Xaa Ala Asn Arg His Leu Leu
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is S5, a-methyl, a-alkenylglycine with 5
      carbon chain
<220> FEATURE:
<221> NAME/KEY: misc_feature
<222> LOCATION: (7)..(7)
<223> OTHER INFORMATION: Xaa is S5, a-methyl, a-alkenylglycine with 5
      carbon chain

<400> SEQUENCE: 68

Ile Leu Xaa Ala Ser Val Xaa Tyr Ile Arg Lys Leu Gln Arg Glu Gln
1               5                   10                  15

<210> SEQ ID NO 69
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain

<400> SEQUENCE: 69

Phe Asn Ile Xaa Asp Arg Ile Xaa Glu Leu Gly Thr Leu Ile
1               5                   10

<210> SEQ ID NO 70
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is S5, a-methyl, a-alkenylglycine with 5
      carbon chain
<220> FEATURE:
<221> NAME/KEY: misc_feature
<222> LOCATION: (7)..(7)
<223> OTHER INFORMATION: Xaa is S5, a-methyl, a-alkenylglycine with 5
      carbon chain

<400> SEQUENCE: 70

Lys Asn Xaa Thr His Gln Xaa Asp Ile
1               5
```

```
<210> SEQ ID NO 71
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(13)
<223> OTHER INFORMATION: Xaa is S5, a-methyl, a-alkenylglycine with 5
      carbon chain
<220> FEATURE:
<221> NAME/KEY: misc_feature
<222> LOCATION: (17)..(17)
<223> OTHER INFORMATION: Xaa is S5, a-methyl, a-alkenylglycine with 5
      carbon chain

<400> SEQUENCE: 71

Ser Thr Ala Leu Arg Glu Leu Ile Glu Glu Leu Val Xaa Ile Thr Gln
1               5                   10                  15

Xaa Gln Lys Ala Pro Leu
            20

<210> SEQ ID NO 72
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa is S5, a-methyl, a-alkenylglycine with 5
      carbon chain
<220> FEATURE:
<221> NAME/KEY: misc_feature
<222> LOCATION: (9)..(9)
<223> OTHER INFORMATION: Xaa is S5, a-methyl, a-alkenylglycine with 5
      carbon chain

<400> SEQUENCE: 72

Asn Glu Leu Lys Xaa Ser Phe Phe Xaa Leu Arg Asp Gln Ile
1               5                   10

<210> SEQ ID NO 73
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: Xaa is S5, a-methyl, a-alkenylglycine with 5
      carbon chain
<220> FEATURE:
<221> NAME/KEY: misc_feature
<222> LOCATION: (14)..(14)
<223> OTHER INFORMATION: Xaa is S5, a-methyl, a-alkenylglycine with 5
      carbon chain

<400> SEQUENCE: 73

Leu Glu Asn Arg Gln Lys Lys Leu Glu Xaa Ala Asn Arg Xaa Leu Leu
1               5                   10                  15

<210> SEQ ID NO 74
<211> LENGTH: 16
<212> TYPE: PRT
<213> ORGANISM: Artificial Sequence
<220> FEATURE:
```

<223> OTHER INFORMATION: Synthetic
<220> FEATURE:
<221> NAME/KEY: misc_feature
<222> LOCATION: (6)..(6)
<223> OTHER INFORMATION: Xaa is S5, a-methyl, a-alkenylglycine with 5
      carbon chain
<220> FEATURE:
<221> NAME/KEY: misc_feature
<222> LOCATION: (10)..(10)
<223> OTHER INFORMATION: Xaa is S5, a-methyl, a-alkenylglycine with 5
      carbon chain

<400> SEQUENCE: 74

Ile Leu Lys Ala Ser Xaa Asp Tyr Ile Xaa Lys Leu Gln Arg Glu Gln
1               5                   10                  15

<210> SEQ ID NO 75
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa is S5, a-methyl, a-alkenylglycine with 5
      carbon chain
<220> FEATURE:
<221> NAME/KEY: misc_feature
<222> LOCATION: (9)..(9)
<223> OTHER INFORMATION: Xaa is S5, a-methyl, a-alkenylglycine with 5
      carbon chain

<400> SEQUENCE: 75

Asp His Ile Lys Xaa Ser Phe His Xaa Leu Arg Asp Ser Val
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain

<400> SEQUENCE: 76

Asp His Ile Lys Asp Ser Phe Xaa Ser Leu Arg Xaa Ser Val
1               5                   10

<210> SEQ ID NO 77
<211> LENGTH: 38
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is S5, a-methyl, a-alkenylglycine with 5
      carbon chain
<220> FEATURE:
<221> NAME/KEY: misc_feature
<222> LOCATION: (5)..(5)
<223> OTHER INFORMATION: Xaa is S5, a-methyl, a-alkenylglycine with 5 carbon chain

<400> SEQUENCE: 77

Xaa Tyr Ile Gln Xaa Asn Leu Arg Arg Lys Asn His Thr His Gln Gln
1               5                   10                  15

Asp Ile Asp Asp Leu Leu Lys Arg Gln Asn Ala Leu Leu Glu Gln Gln
            20                  25                  30

Val Arg Ala Leu Gly Gly
        35

<210> SEQ ID NO 78
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain

<400> SEQUENCE: 78

Thr Tyr Arg Gly Ala Ala Gln Xaa Ala Ala Gln Xaa Val Arg Glu Val
1               5                   10                  15

<210> SEQ ID NO 79
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is S5, a-methyl, a-alkenylglycine with 5
      carbon chain
<220> FEATURE:
<221> NAME/KEY: misc_feature
<222> LOCATION: (7)..(7)
<223> OTHER INFORMATION: Xaa is S5, a-methyl, a-alkenylglycine with 5
      carbon chain

<400> SEQUENCE: 79

Thr Tyr Xaa Gly Ala Phe Xaa Asn Leu Phe Gln Ser Val Arg Glu Val
1               5                   10                  15

<210> SEQ ID NO 80
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa is S5, a-methyl, a-alkenylglycine with 5
      carbon chain
<220> FEATURE:
<221> NAME/KEY: misc_feature
<222> LOCATION: (6)..(6)
<223> OTHER INFORMATION: Xaa is S5, a-methyl, a-alkenylglycine with 5
      carbon chain

<400> SEQUENCE: 80

-continued

```
Ala Xaa Ser Val Phe Xaa Asn Tyr Phe His Ser Val Pro Tyr Phe Glu
1               5                   10                  15

Leu

<210> SEQ ID NO 81
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain

<400> SEQUENCE: 81

Gly Ala Phe Xaa Asn Leu Phe Xaa Ser Val
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is S5, a-methyl, a-alkenylglycine with 5
      carbon chain
<220> FEATURE:
<221> NAME/KEY: misc_feature
<222> LOCATION: (5)..(5)
<223> OTHER INFORMATION: Xaa is S5, a-methyl, a-alkenylglycine with 5
      carbon chain
<220> FEATURE:
<221> NAME/KEY: misc_feature
<222> LOCATION: (9)..(9)
<223> OTHER INFORMATION: Xaa is R5, an enantiomer of S5, a-methyl,
      a-alkenylglycine with 5 carbon chain

<400> SEQUENCE: 82

Xaa Gly Ala Phe Xaa Asn Leu Phe Xaa Ser Val
1               5                   10

<210> SEQ ID NO 83
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain

<400> SEQUENCE: 83

Ser Tyr Arg Gly Ala Phe Gln Xaa Leu Phe Gln Xaa Val Arg Glu Val
1               5                   10                  15
```

<210> SEQ ID NO 84
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa is S5, a-methyl, a-alkenylglycine with 5
      carbon chain
<220> FEATURE:
<221> NAME/KEY: misc_feature
<222> LOCATION: (10)..(10)
<223> OTHER INFORMATION: Xaa is S5, a-methyl, a-alkenylglycine with 5
      carbon chain

<400> SEQUENCE: 84

Ser Ser Val Phe Tyr Xaa Tyr Phe His Xaa Val Pro Tyr Phe Glu Leu
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa is S5, a-methyl, a-alkenylglycine with 5
      carbon chain
<220> FEATURE:
<221> NAME/KEY: misc_feature
<222> LOCATION: (6)..(6)
<223> OTHER INFORMATION: Xaa is S5, a-methyl, a-alkenylglycine with 5
      carbon chain

<400> SEQUENCE: 85

Ala Xaa Thr Leu Phe Xaa Thr Phe Tyr Leu Gly Gly Leu Leu Gly
1               5                   10                  15

<210> SEQ ID NO 86
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (2)..(2)
<223> OTHER INFORMATION: Xaa is S5, a-methyl, a-alkenylglycine with 5
      carbon chain
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa is S5, a-methyl, a-alkenylglycine with 5
      carbon chain

<400> SEQUENCE: 86

Xaa Gly Ala Phe Xaa Asn Leu Phe Gln Ser Val
1               5                   10

<210> SEQ ID NO 87

```
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa is S5, a-methyl, a-alkenylglycine with 5
      carbon chain
<220> FEATURE:
<221> NAME/KEY: misc_feature
<222> LOCATION: (6)..(6)
<223> OTHER INFORMATION: Xaa is S5, a-methyl, a-alkenylglycine with 5
      carbon chain

<400> SEQUENCE: 87

Ala Xaa Ser Ser Phe Xaa Asp Phe Phe His Thr Val Pro Tyr Asn Leu
1               5                   10                  15

Leu

<210> SEQ ID NO 88
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain

<400> SEQUENCE: 88

Glu Arg Leu Arg Arg Arg Ile Xaa Leu Cys Arg Xaa His His Ser Thr
1               5                   10                  15

<210> SEQ ID NO 89
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain
<220> FEATURE:
<221> NAME/KEY: misc_feature
<222> LOCATION: (13)..(13)
<223> OTHER INFORMATION: Xaa is S5, a-methyl, a-alkenylglycine with 5
      carbon chain

<400> SEQUENCE: 89

Glu Arg Leu Arg Arg Arg Ile Xaa Asn Leu Cys Arg Xaa His His Ser
1               5                   10                  15

Thr

<210> SEQ ID NO 90
<211> LENGTH: 16
<212> TYPE: PRT
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (8)..(8)
<223> OTHER INFORMATION: Xaa is S5, a-methyl, a-alkenylglycine with 5
      carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain

<400> SEQUENCE: 90

Glu Arg Leu Arg Arg Arg Leu Xaa Leu Cys Arg Xaa His His Ser Thr
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain

<400> SEQUENCE: 91

Glu Arg Leu Arg Arg Arg Phe Xaa Leu Cys Arg Xaa His His Ser Thr
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain

<400> SEQUENCE: 92

Glu Arg Phe Arg Arg Arg Ile Xaa Leu Cys Arg Xaa His His Ser Thr
1               5                   10                  15

<210> SEQ ID NO 93
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain
```

<400> SEQUENCE: 93

Glu Arg Leu Ala Arg Arg Ile Xaa Leu Cys Arg Xaa His His Ser Thr
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa is S5, a-methyl, a-alkenylglycine with 5
      carbon chain
<220> FEATURE:
<221> NAME/KEY: misc_feature
<222> LOCATION: (13)..(13)
<223> OTHER INFORMATION: Xaa is S5, a-methyl, a-alkenylglycine with 5
      carbon chain

<400> SEQUENCE: 94

Glu Asn Pro Glu Ser Ile Leu Asp Xaa His Val Gln Xaa Val Met
1               5                   10                  15

<210> SEQ ID NO 95
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is S5, a-methyl, a-alkenylglycine with 5
      carbon chain
<220> FEATURE:
<221> NAME/KEY: misc_feature
<222> LOCATION: (7)..(7)
<223> OTHER INFORMATION: Xaa is S5, a-methyl, a-alkenylglycine with 5
      carbon chain

<400> SEQUENCE: 95

Pro Glu Xaa Ile Leu Asp Xaa His Val Gln Arg Val Met
1               5                   10

<210> SEQ ID NO 96
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain

<400> SEQUENCE: 96

Glu Arg Leu Arg Arg Arg Ile Xaa Phe Cys Arg Xaa His His Ser Thr
1               5                   10                  15

<210> SEQ ID NO 97
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa is S5, a-methyl, a-alkenylglycine with 5
      carbon chain
<220> FEATURE:
<221> NAME/KEY: misc_feature
<222> LOCATION: (13)..(13)
<223> OTHER INFORMATION: Xaa is S5, a-methyl, a-alkenylglycine with 5
      carbon chain

<400> SEQUENCE: 97

Glu Arg Leu Arg Arg Arg Asn Leu Xaa Leu Cys Arg Xaa His His Ser
1               5                   10                  15

Thr

<210> SEQ ID NO 98
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa is S5, a-methyl, a-alkenylglycine with 5
      carbon chain
<220> FEATURE:
<221> NAME/KEY: misc_feature
<222> LOCATION: (13)..(13)
<223> OTHER INFORMATION: Xaa is S5, a-methyl, a-alkenylglycine with 5
      carbon chain

<400> SEQUENCE: 98

Glu Arg Asn Leu Arg Arg Arg Ile Xaa Leu Cys Arg Xaa His His Ser
1               5                   10                  15

Thr

<210> SEQ ID NO 99
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain

<400> SEQUENCE: 99

Glu Arg Trp Arg Arg Arg Ile Xaa Leu Cys Arg Xaa His His Ser Thr
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa is S5, a-methyl, a-alkenylglycine with 5

```
            carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain

<400> SEQUENCE: 100

Arg Glu Leu Arg Arg Glu Ile Xaa Leu Cys Arg Xaa His His Ser Thr
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa is S5, a-methyl, a-alkenylglycine with 5
      carbon chain
<220> FEATURE:
<221> NAME/KEY: misc_feature
<222> LOCATION: (9)..(9)
<223> OTHER INFORMATION: Xaa is S5, a-methyl, a-alkenylglycine with 5
      carbon chain

<400> SEQUENCE: 101

Glu Asn Pro Glu Xaa Ile Leu Asp Xaa His Val Gln Arg Val Met
1               5                   10                  15

<210> SEQ ID NO 102
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain

<400> SEQUENCE: 102

Asn Pro Glu Xaa Ile Leu Asp Xaa His Val Gln Arg Val Met
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain

<400> SEQUENCE: 103

Trp Pro Glu Xaa Ile Leu Asp Xaa His Val Gln Arg Val Met
```

```
1               5              10

<210> SEQ ID NO 104
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is S5, a-methyl, a-alkenylglycine with 5
      carbon chain
<220> FEATURE:
<221> NAME/KEY: misc_feature
<222> LOCATION: (7)..(7)
<223> OTHER INFORMATION: Xaa is S5, a-methyl, a-alkenylglycine with 5
      carbon chain

<400> SEQUENCE: 104

Pro Glu Xaa Ile Leu Asp Xaa His Val Arg Arg Val Met Arg
1               5                   10

<210> SEQ ID NO 105
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain

<400> SEQUENCE: 105

Arg Pro Glu Xaa Ile Leu Asp Xaa His Val Arg Arg Val Met Arg
1               5                   10                  15

<210> SEQ ID NO 106
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain

<400> SEQUENCE: 106

Thr Arg Gln Ala Xaa Arg Asn Arg Arg Arg Arg Xaa Arg Arg
1               5                   10

<210> SEQ ID NO 107
<211> LENGTH: 17
<212> TYPE: PRT
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (10)..(10)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (17)..(17)
<223> OTHER INFORMATION: Xaa is S5, a-methyl, a-alkenylglycine with 5
      carbon chain

<400> SEQUENCE: 107

Arg Arg Gly Ser Arg Pro Ser Gly Ala Xaa Arg Arg Arg Arg Arg Ala
1               5                   10                  15

Xaa

<210> SEQ ID NO 108
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (17)..(17)
<223> OTHER INFORMATION: Xaa is S5, a-methyl, a-alkenylglycine with 5
      carbon chain

<400> SEQUENCE: 108

Arg Arg Gly Ser Arg Pro Ser Gly Ala Xaa Arg Arg Arg Arg Arg Ala
1               5                   10                  15

Xaa Ala Ala

<210> SEQ ID NO 109
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (15)..(15)
<223> OTHER INFORMATION: Xaa is S5, a-methyl, a-alkenylglycine with 5
      carbon chain

<400> SEQUENCE: 109

Thr Arg Gln Ala Arg Arg Asn Xaa Arg Arg Arg Trp Arg Glu Xaa Gln
1               5                   10                  15

Arg

<210> SEQ ID NO 110
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa is R5, an enantiomer of S5, a-methyl,
      a-alkenylglycine with 5 carbon chain
```

```
<220> FEATURE:
<221> NAME/KEY: misc_feature
<222> LOCATION: (12)..(12)
<223> OTHER INFORMATION: Xaa is S8, a-methyl, a-alkenylglycine with 8
      carbon chain

<400> SEQUENCE: 110

Arg Arg Arg Arg Xaa Arg Arg Arg Trp Arg Arg Xaa
1               5                   10

<210> SEQ ID NO 111
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain

<400> SEQUENCE: 111

Lys Pro Glu Xaa Ile Leu Asp Xaa His Val Gln Arg Val Met
1               5                   10

<210> SEQ ID NO 112
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain

<400> SEQUENCE: 112

Trp Pro Glu Xaa Ile Leu Asp Xaa His Val Arg Arg Val Met Arg
1               5                   10                  15

<210> SEQ ID NO 113
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain

<400> SEQUENCE: 113

Arg Arg Arg Arg Xaa Arg Gln Arg Arg Arg Xaa Arg Arg
1               5                   10
```

<210> SEQ ID NO 114
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (17)..(17)
<223> OTHER INFORMATION: Xaa is S5, a-methyl, a-alkenylglycine with 5
      carbon chain

<400> SEQUENCE: 114

Arg Arg Gly Ser Arg Pro Ser Gly Ala Xaa Arg Arg Arg Arg Arg
1               5                   10                  15

Xaa

<210> SEQ ID NO 115
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain

<400> SEQUENCE: 115

Xaa Arg Arg Gln Arg Arg Arg Xaa Arg Gln Arg Arg Arg Arg
1               5                   10                  15

<210> SEQ ID NO 116
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa is R5, an enantiomer of S5, a-methyl,
      a-alkenylglycine with 5 carbon chain
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa is S8, a-methyl, a-alkenylglycine with 8
      carbon chain

<400> SEQUENCE: 116

Arg Arg Arg Arg Xaa Arg Arg Xaa Arg Arg Arg Xaa
1               5                   10

```
<210> SEQ ID NO 117
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa is R5, an enantiomer of S5, a-methyl,
      a-alkenylglycine with 5 carbon chain
<220> FEATURE:
<221> NAME/KEY: misc_feature
<222> LOCATION: (12)..(12)
<223> OTHER INFORMATION: Xaa is S8, a-methyl, a-alkenylglycine with 8
      carbon chain

<400> SEQUENCE: 117

Tyr Gly Arg Lys Xaa Arg Arg Gln Arg Arg Arg Xaa
1               5                   10

<210> SEQ ID NO 118
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (9)..(9)
<223> OTHER INFORMATION: Xaa is S5, a-methyl, a-alkenylglycine with 5
      carbon chain

<400> SEQUENCE: 118

Ser Xaa Glu Leu Val Ala Glu Ala Xaa Asn Leu Cys Thr Leu Leu Glu
1               5                   10                  15

Asn Ala Ile Gln Asp Thr Val Arg Glu Gln
            20                  25

<210> SEQ ID NO 119
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (17)..(17)
<223> OTHER INFORMATION: Xaa is S5, a-methyl, a-alkenylglycine with 5
      carbon chain

<400> SEQUENCE: 119

Ser Glu Glu Leu Val Ala Glu Ala His Xaa Leu Cys Thr Leu Leu Glu
1               5                   10                  15

Xaa Ala Ile Gln Asp Thr Val Arg Glu Gln
            20                  25

<210> SEQ ID NO 120
<211> LENGTH: 26
```

```
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (21)..(21)
<223> OTHER INFORMATION: Xaa is S5, a-methyl, a-alkenylglycine with 5
      carbon chain

<400> SEQUENCE: 120

Ser Glu Glu Leu Val Ala Glu Ala His Asn Leu Cys Thr Xaa Leu Glu
1               5                   10                  15

Asn Ala Ile Gln Xaa Thr Val Arg Glu Gln
            20                  25

<210> SEQ ID NO 121
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa is R5, an enantiomer of S5, a-methyl,
      a-alkenylglycine with 5 carbon chain
<220> FEATURE:
<221> NAME/KEY: misc_feature
<222> LOCATION: (14)..(14)
<223> OTHER INFORMATION: Xaa is S8, a-methyl, a-alkenylglycine with 8
      carbon chain

<400> SEQUENCE: 121

Arg Gln Ile Lys Ile Trp Xaa Gln Asn Arg Arg Met Lys Xaa Lys Lys
1               5                   10                  15

<210> SEQ ID NO 122
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (10)..(10)
<223> OTHER INFORMATION: Xaa is S5, a-methyl, a-alkenylglycine with 5
      carbon chain

<400> SEQUENCE: 122

Ser Glu Xaa Leu Val Ala Glu Ala His Xaa Leu Cys Thr Leu Leu Glu
1               5                   10                  15

Asn Ala Ile Gln Asp Thr Val Arg Glu Gln
            20                  25

<210> SEQ ID NO 123
<211> LENGTH: 26
<212> TYPE: PRT
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (13)..(13)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (20)..(20)
<223> OTHER INFORMATION: Xaa is S5, a-methyl, a-alkenylglycine with 5
      carbon chain

<400> SEQUENCE: 123

Ser Glu Glu Leu Val Ala Glu Ala His Asn Leu Cys Xaa Leu Leu Glu
1               5                   10                  15

Asn Ala Ile Xaa Asp Thr Val Arg Glu Gln
            20                  25

<210> SEQ ID NO 124
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (24)..(24)
<223> OTHER INFORMATION: Xaa is S5, a-methyl, a-alkenylglycine with 5
      carbon chain

<400> SEQUENCE: 124

Ser Glu Glu Leu Val Ala Glu Ala His Asn Leu Cys Thr Leu Leu Glu
1               5                   10                  15

Xaa Ala Ile Gln Asp Thr Val Xaa Glu Gln
            20                  25

<210> SEQ ID NO 125
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (14)..(14)
<223> OTHER INFORMATION: Xaa is S5, a-methyl, a-alkenylglycine with 5
      carbon chain

<400> SEQUENCE: 125

Leu Ser Gln Glu Thr Phe Xaa Asp Leu Trp Lys Leu Leu Xaa Glu Asn
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
``` a-alkenylglycine with 8 carbon chain
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain

<400> SEQUENCE: 126

Ile Leu Arg Xaa Ala Val Ser His Met Lys Xaa Leu Arg Gly Thr
1               5                   10                  15

<210> SEQ ID NO 127
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain

<400> SEQUENCE: 127

Asn Glu Leu Xaa Arg Ser Phe Arg Ser Leu Xaa Asp Ser Ile
1               5                   10

<210> SEQ ID NO 128
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain

<400> SEQUENCE: 128

Asn Glu Leu Xaa Arg Ser Phe Arg Ala Leu Xaa Asp Gln Ile
1               5                   10

<210> SEQ ID NO 129
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain

<400> SEQUENCE: 129

Asn Glu Leu Xaa Arg Ser Phe Phe Ala Leu Xaa Asp Ser Ile

```
1               5                   10
```

```
<210> SEQ ID NO 130
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain

<400> SEQUENCE: 130

Asn Glu Leu Xaa Arg Ser Phe Phe Ala Leu Xaa Asp Gln Ile
1               5                   10

<210> SEQ ID NO 131
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (10)..(10)
<223> OTHER INFORMATION: Xaa is S5, a-methyl, a-alkenylglycine with 5
      carbon chain

<400> SEQUENCE: 131

Ile Leu Xaa Met Ala Val Ser His Met Xaa Ser Leu Arg Gly Thr
1               5                   10                  15

<210> SEQ ID NO 132
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain

<400> SEQUENCE: 132

Asn Glu Leu Xaa Arg Ser Phe Arg Ala Leu Xaa Asp Ser Ile
1               5                   10

<210> SEQ ID NO 133
<211> LENGTH: 14
<212> TYPE: PRT
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain

<400> SEQUENCE: 133

Asn Glu Leu Xaa Arg Ser Phe Phe Ser Leu Xaa Asp Gln Ile
1               5                   10

<210> SEQ ID NO 134
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain

<400> SEQUENCE: 134

Trp Asn Glu Leu Xaa Arg Ser Phe Arg Ser Leu Xaa Asp Gln Ile
1               5                   10                  15

<210> SEQ ID NO 135
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain

<400> SEQUENCE: 135

Asn Gln Arg Xaa Leu Ser Phe Phe Ala Leu Xaa Asp Gln Ile
1               5                   10

<210> SEQ ID NO 136
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain
```

```
<400> SEQUENCE: 136

Asn Gln Leu Xaa Leu Ser Phe Phe Ala Arg Xaa Asp Gln Ile
1               5                   10

<210> SEQ ID NO 137
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain

<400> SEQUENCE: 137

Asn Lys Leu Xaa Arg Ser Phe Phe Ala Leu Xaa Asp Gln Ile
1               5                   10

<210> SEQ ID NO 138
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain

<400> SEQUENCE: 138

Asn Glu Leu Lys Xaa Ser Phe Phe Ala Leu Arg Xaa Gln Ile Pro Glu
1               5                   10                  15

Leu Glu Asn Asn Glu Lys Ala Pro
            20

<210> SEQ ID NO 139
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain

<400> SEQUENCE: 139

Ala His Leu Xaa Leu Cys Leu Glu Lys Leu Xaa Gly Leu Val
1               5                   10

<210> SEQ ID NO 140
```

```
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain

<400> SEQUENCE: 140

Asn Lys Leu Xaa Arg Ser Phe Lys Ala Leu Xaa Lys Gln Ile
1               5                   10

<210> SEQ ID NO 141
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain

<400> SEQUENCE: 141

Asn Glu Leu Lys Xaa Ser Phe Phe Ala Leu Arg Xaa Gln Ile
1               5                   10

<210> SEQ ID NO 142
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain

<400> SEQUENCE: 142

Asn Gln Leu Xaa Arg Ser Phe Phe Ala Leu Xaa Asp Gln Ile Pro Glu
1               5                   10                  15

Leu Glu Asn Asn Glu Lys Ala Pro
            20

<210> SEQ ID NO 143
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (3)..(3)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (10)..(10)
<223> OTHER INFORMATION: Xaa is S5, a-methyl, a-alkenylglycine with 5
      carbon chain

<400> SEQUENCE: 143

Lys Val Xaa Ile Leu Lys Lys Ala Thr Xaa Tyr Ile Leu Ser
1               5                   10

<210> SEQ ID NO 144
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain

<400> SEQUENCE: 144

Xaa Lys Arg Arg Ala His Ala Xaa Ala Glu Arg Ala Arg Arg
1               5                   10

<210> SEQ ID NO 145
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (15)..(15)
<223> OTHER INFORMATION: Xaa is S5, a-methyl, a-alkenylglycine with 5
      carbon chain

<400> SEQUENCE: 145

Glu Glu Asn Ala Lys Arg Arg Xaa His Asn Ala Leu Glu Arg Xaa Arg
1               5                   10                  15

Arg

<210> SEQ ID NO 146
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (7)..(7)
<223> OTHER INFORMATION: Xaa is S5, a-methyl, a-alkenylglycine with 5
      carbon chain
```

<400> SEQUENCE: 146

Asn Gln Leu Xaa Leu Ser Xaa Asp Gln Ile
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (7)..(7)
<223> OTHER INFORMATION: Xaa is S5, a-methyl, a-alkenylglycine with 5
      carbon chain

<400> SEQUENCE: 147

Asn Gln Leu Xaa Phe Ser Xaa Asp Gln Ile
1               5                   10

<210> SEQ ID NO 148
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (21)..(21)
<223> OTHER INFORMATION: Xaa is S5, a-methyl, a-alkenylglycine with 5
      carbon chain

<400> SEQUENCE: 148

Thr Ile Leu Lys Ala Ser Val Asp Tyr Ile Arg Lys Leu Xaa Arg Glu
1               5                   10                  15

Gln Gln Arg Ala Xaa Glu Leu
            20

<210> SEQ ID NO 149
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain

<400> SEQUENCE: 149

Phe Asn Ile Xaa Asp Arg Ile Xaa Thr Leu Ile
1               5                   10

```
<210> SEQ ID NO 150
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (8)..(8)
<223> OTHER INFORMATION: Xaa is S5, a-methyl, a-alkenylglycine with 5
      carbon chain

<400> SEQUENCE: 150

Arg Asn Ile Xaa Asp Arg Ile Xaa Thr Arg Ile
1               5                   10

<210> SEQ ID NO 151
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(15)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (22)..(22)
<223> OTHER INFORMATION: Xaa is S5, a-methyl, a-alkenylglycine with 5
      carbon chain

<400> SEQUENCE: 151

Lys Ala Thr Glu Tyr Ile Gln Tyr Asn Leu Arg Arg Lys Asn Xaa Thr
1               5                   10                  15

His Gln Gln Asp Ile Xaa Asp Leu
            20

<210> SEQ ID NO 152
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain

<400> SEQUENCE: 152

Asn Glu Leu Xaa Arg Ser Phe Phe Ala Leu Xaa Asp Gln Ile Asp Gln
1               5                   10                  15

Ile Pro Ala Ala Lys Arg Val Lys Leu Asp
            20                  25

<210> SEQ ID NO 153
<211> LENGTH: 14
<212> TYPE: PRT
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain

<400> SEQUENCE: 153

Arg Asn Ile Xaa Asp Arg Ile Lys Glu Leu Xaa Thr Leu Ile
1               5                   10

<210> SEQ ID NO 154
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain

<400> SEQUENCE: 154

Phe Asn Ile Asn Xaa Arg Ile Lys Glu Leu Gly Xaa Leu Ile
1               5                   10

<210> SEQ ID NO 155
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain

<400> SEQUENCE: 155

Phe Asn Ile Xaa Asp Arg Ile Lys Glu Leu Xaa Thr Arg Ile
1               5                   10

<210> SEQ ID NO 156
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (11)..(11)
```

```
<223> OTHER INFORMATION: Xaa is S5, a-methyl, a-alkenylglycine with 5
      carbon chain

<400> SEQUENCE: 156

Asn Gln Leu Xaa Arg Ser Phe Arg Ala Leu Xaa Asp Gln Ile
1               5                   10

<210> SEQ ID NO 157
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain

<400> SEQUENCE: 157

Asn Glu Leu Xaa Arg Ser Phe Phe Ala Leu Xaa Asp Gln Ile Asp Gln
1               5                   10                  15

Ile Pro Lys Lys Lys Arg Lys Val
            20

<210> SEQ ID NO 158
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (12)..(12)
<223> OTHER INFORMATION: Xaa is S5, a-methyl, a-alkenylglycine with 5
      carbon chain

<400> SEQUENCE: 158

Glu Asn Pro Glu Xaa Ile Leu Asp Glu His Val Xaa Arg Val Met
1               5                   10                  15

<210> SEQ ID NO 159
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (8)..(8)
<223> OTHER INFORMATION: Xaa is B5, a-methyl, a-alkenylglycine with two
      5 carbon chain
<220> FEATURE:
<221> NAME/KEY: misc_feature
<222> LOCATION: (15)..(15)
<223> OTHER INFORMATION: Xaa is S8, a-methyl, a-alkenylglycine with 8
      carbon chain
```

```
<400> SEQUENCE: 159

Thr Arg Gln Xaa Arg Arg Ala Xaa Arg Arg Trp Arg Glu Xaa Gln
1               5                   10                  15

Arg

<210> SEQ ID NO 160
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is S8, a-methyl, a-alkenylglycine with 8
      carbon chain
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa is B5, a-methyl, a-alkenylglycine with two
      5 carbon chain
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa is S8, a-methyl, a-alkenylglycine with 8
      carbon chain

<400> SEQUENCE: 160

Xaa Arg Arg Asn Xaa Arg Arg Arg Trp Arg Glu Xaa
1               5                   10

<210> SEQ ID NO 161
<211> LENGTH: 37
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa is R5, an enantiomer of S5, a-methyl,
      a-alkenylglycine with 5 carbon chain
<220> FEATURE:
<221> NAME/KEY: misc_feature
<222> LOCATION: (13)..(13)
<223> OTHER INFORMATION: Xaa is S8, a-methyl, a-alkenylglycine with 8
      carbon chain

<400> SEQUENCE: 161

Glu Tyr Ile Gln Xaa Asn Leu Arg Arg Lys Asn His Xaa His Gln Gln
1               5                   10                  15

Asp Ile Asp Asp Leu Lys Arg Gln Asn Ala Leu Leu Glu Gln Gln Val
            20                  25                  30

Arg Ala Leu Gly Gly
        35

<210> SEQ ID NO 162
<211> LENGTH: 15
<212> TYPE: PRT
<213> ORGANISM: Artificial Sequence
<220> FEATURE:
```

-continued

```
<223> OTHER INFORMATION: Synthetic
<220> FEATURE:
<221> NAME/KEY: misc_feature
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (6)..(6)
<223> OTHER INFORMATION: Xaa is B5, a-methyl, a-alkenylglycine with two
      5 carbon chain
<220> FEATURE:
<221> NAME/KEY: misc_feature
<222> LOCATION: (13)..(13)
<223> OTHER INFORMATION: Xaa is S8, a-methyl, a-alkenylglycine with 8
      carbon chain

<400> SEQUENCE: 162

Thr Arg Gln Xaa Gln Xaa Arg Arg Trp Arg Glu Xaa Gln Arg
1               5                   10                  15

<210> SEQ ID NO 163
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (8)..(8)
<223> OTHER INFORMATION: Xaa is B5, a-methyl, a-alkenylglycine with two
      5 carbon chain
<220> FEATURE:
<221> NAME/KEY: misc_feature
<222> LOCATION: (15)..(15)
<223> OTHER INFORMATION: Xaa is S8, a-methyl, a-alkenylglycine with 8
      carbon chain

<400> SEQUENCE: 163

Thr Arg Gln Xaa Arg Arg Asn Xaa Arg Arg Trp Arg Glu Xaa Gln
1               5                   10                  15

Arg

<210> SEQ ID NO 164
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (8)..(8)
<223> OTHER INFORMATION: Xaa is B5, a-methyl, a-alkenylglycine with two
      5 carbon chain
<220> FEATURE:
<221> NAME/KEY: misc_feature
<222> LOCATION: (15)..(15)
<223> OTHER INFORMATION: Xaa is S8, a-methyl, a-alkenylglycine with 8
      carbon chain

<400> SEQUENCE: 164

Xaa Arg Gln Ala Arg Arg Asn Xaa Arg Arg Trp Arg Glu Xaa Gln
1               5                   10                  15
```

Arg

<210> SEQ ID NO 165
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is is R8, an enantiomer of S8, a-methyl,
      a-alkenylglycine with 8 carbon chain
<220> FEATURE:
<221> NAME/KEY: misc_feature
<222> LOCATION: (8)..(8)
<223> OTHER INFORMATION: Xaa is B5, a-methyl, a-alkenylglycine with two
      5 carbon chain
<220> FEATURE:
<221> NAME/KEY: misc_feature
<222> LOCATION: (15)..(15)
<223> OTHER INFORMATION: Xaa is S8, a-methyl, a-alkenylglycine with 8
      carbon chain

<400> SEQUENCE: 165

Xaa Arg Gln Ala Arg Arg Gln Xaa Arg Arg Arg Trp Arg Glu Xaa Gln
1               5                   10                  15

Arg

<210> SEQ ID NO 166
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is S5, a-methyl, a-alkenylglycine with 5
      carbon chain
<220> FEATURE:
<221> NAME/KEY: misc_feature
<222> LOCATION: (5)..(5)
<223> OTHER INFORMATION: Xaa is B5, a-methyl, a-alkenylglycine with two
      5 carbon chain
<220> FEATURE:
<221> NAME/KEY: misc_feature
<222> LOCATION: (12)..(12)
<223> OTHER INFORMATION: Xaa is S8, a-methyl, a-alkenylglycine with 8
      carbon chain

<400> SEQUENCE: 166

Xaa Arg Arg Asn Xaa Arg Arg Arg Trp Arg Arg Xaa
1               5                   10

<210> SEQ ID NO 167
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is B5, a-methyl, a-alkenylglycine with two
      5 carbon chain
<220> FEATURE:
<221> NAME/KEY: misc_feature
<222> LOCATION: (11)..(11)
<223> OTHER INFORMATION: Xaa is S8, a-methyl, a-alkenylglycine with 8
      carbon chain

```
<400> SEQUENCE: 167

Arg Arg Ala Xaa Arg Arg Trp Arg Arg Xaa
1               5                   10

<210> SEQ ID NO 168
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is S5, a-methyl, a-alkenylglycine with 5
      carbon chain
<220> FEATURE:
<221> NAME/KEY: misc_feature
<222> LOCATION: (5)..(5)
<223> OTHER INFORMATION: Xaa is B5, a-methyl, a-alkenylglycine with two
      5 carbon chain
<220> FEATURE:
<221> NAME/KEY: misc_feature
<222> LOCATION: (12)..(12)
<223> OTHER INFORMATION: Xaa is S8, a-methyl, a-alkenylglycine with 8
      carbon chain
<220> FEATURE:
<221> NAME/KEY: misc_feature
<222> LOCATION: (13)..(13)
<223> OTHER INFORMATION: Xaa can be any naturally occurring amino acid

<400> SEQUENCE: 168

Xaa Lys Ile Trp Xaa Gln Asn Arg Arg Asn Leu Lys Xaa
1               5                   10

<210> SEQ ID NO 169
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is S5, a-methyl, a-alkenylglycine with 5
      carbon chain
<220> FEATURE:
<221> NAME/KEY: misc_feature
<222> LOCATION: (5)..(5)
<223> OTHER INFORMATION: Xaa is B5, a-methyl, a-alkenylglycine with two
      5 carbon chain
<220> FEATURE:
<221> NAME/KEY: misc_feature
<222> LOCATION: (12)..(12)
<223> OTHER INFORMATION: Xaa is S8, a-methyl, a-alkenylglycine with 8
      carbon chain

<400> SEQUENCE: 169

Xaa Arg Arg Arg Xaa Arg Arg Arg Arg Arg Xaa
1               5                   10

<210> SEQ ID NO 170
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is S5, a-methyl, a-alkenylglycine with 5
      carbon chain
<220> FEATURE:
<221> NAME/KEY: misc_feature
```

```
<222> LOCATION: (5)..(5)
<223> OTHER INFORMATION: Xaa is B5, a-methyl, a-alkenylglycine with two
      5 carbon chain
<220> FEATURE:
<221> NAME/KEY: misc_feature
<222> LOCATION: (12)..(12)
<223> OTHER INFORMATION: Xaa is S8, a-methyl, a-alkenylglycine with 8
      carbon chain

<400> SEQUENCE: 170

Xaa Gly Arg Lys Xaa Arg Arg Gln Arg Arg Arg Xaa
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is S5, a-methyl, a-alkenylglycine with 5
      carbon chain
<220> FEATURE:
<221> NAME/KEY: misc_feature
<222> LOCATION: (5)..(5)
<223> OTHER INFORMATION: Xaa is B5, a-methyl, a-alkenylglycine with two
      5 carbon chain
<220> FEATURE:
<221> NAME/KEY: misc_feature
<222> LOCATION: (12)..(12)
<223> OTHER INFORMATION: Xaa is S8, a-methyl, a-alkenylglycine with 8
      carbon chain

<400> SEQUENCE: 171

Xaa Arg Arg Gln Xaa Arg Arg Arg Trp Arg Arg Xaa
1               5                   10

<210> SEQ ID NO 172
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is S5, a-methyl, a-alkenylglycine with 5
      carbon chain
<220> FEATURE:
<221> NAME/KEY: misc_feature
<222> LOCATION: (7)..(7)
<223> OTHER INFORMATION: Xaa is B5, a-methyl, a-alkenylglycine with two
      5 carbon chain
<220> FEATURE:
<221> NAME/KEY: misc_feature
<222> LOCATION: (14)..(14)
<223> OTHER INFORMATION: Xaa is S8, a-methyl, a-alkenylglycine with 8
      carbon chain

<400> SEQUENCE: 172

Arg Gln Xaa Lys Ile Trp Xaa Gln Asn Arg Arg Met Lys Xaa Lys Lys
1               5                   10                  15

<210> SEQ ID NO 173
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (1)..(1)
<223> OTHER INFORMATION: Xaa is S5, a-methyl, a-alkenylglycine with 5
      carbon chain
<220> FEATURE:
<221> NAME/KEY: misc_feature
<222> LOCATION: (5)..(5)
<223> OTHER INFORMATION: Xaa is B5, a-methyl, a-alkenylglycine with two
      5 carbon chain
<220> FEATURE:
<221> NAME/KEY: misc_feature
<222> LOCATION: (12)..(12)
<223> OTHER INFORMATION: Xaa is S8, a-methyl, a-alkenylglycine with 8
      carbon chain

<400> SEQUENCE: 173

Xaa Lys Ile Trp Xaa Gln Asn Arg Arg Ala Lys Xaa
1               5                   10

<210> SEQ ID NO 174
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is S5, a-methyl, a-alkenylglycine with 5
      carbon chain
<220> FEATURE:
<221> NAME/KEY: misc_feature
<222> LOCATION: (5)..(5)
<223> OTHER INFORMATION: Xaa is B5, a-methyl, a-alkenylglycine with two
      5 carbon chain
<220> FEATURE:
<221> NAME/KEY: misc_feature
<222> LOCATION: (12)..(12)
<223> OTHER INFORMATION: Xaa is S8, a-methyl, a-alkenylglycine with 8
      carbon chain

<400> SEQUENCE: 174

Xaa Arg Arg Arg Xaa Arg Arg Arg Trp Arg Arg Xaa
1               5                   10

<210> SEQ ID NO 175
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa is S5, a-methyl, a-alkenylglycine with 5
      carbon chain
<220> FEATURE:
<221> NAME/KEY: misc_feature
<222> LOCATION: (6)..(6)
<223> OTHER INFORMATION: Xaa is B5, a-methyl, a-alkenylglycine with two
      5 carbon chain
<220> FEATURE:
<221> NAME/KEY: misc_feature
<222> LOCATION: (13)..(13)
<223> OTHER INFORMATION: Xaa is S8, a-methyl, a-alkenylglycine with 8
      carbon chain

<400> SEQUENCE: 175

Leu Xaa Ile Leu Gln Xaa Ala Val Gln Val Ile Leu Xaa Leu Glu Gln
1               5                   10                  15

Gln Val Arg Glu Arg
            20
```

```
<210> SEQ ID NO 176
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa is S5, a-methyl, a-alkenylglycine with 5
      carbon chain
<220> FEATURE:
<221> NAME/KEY: misc_feature
<222> LOCATION: (13)..(13)
<223> OTHER INFORMATION: Xaa is B5, a-methyl, a-alkenylglycine with two
      5 carbon chain
<220> FEATURE:
<221> NAME/KEY: misc_feature
<222> LOCATION: (20)..(20)
<223> OTHER INFORMATION: Xaa is S8, a-methyl, a-alkenylglycine with 8
      carbon chain

<400> SEQUENCE: 176

Leu Leu Ile Leu Gln Gln Ala Val Xaa Val Ile Leu Xaa Leu Glu Gln
1               5                   10                  15

Gln Val Arg Xaa Arg
            20

<210> SEQ ID NO 177
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is S5, a-methyl, a-alkenylglycine with 5
      carbon chain
<220> FEATURE:
<221> NAME/KEY: misc_feature
<222> LOCATION: (7)..(7)
<223> OTHER INFORMATION: Xaa is B8, a-methyl, a-alkenylglycine with two
      8 carbon chain
<220> FEATURE:
<221> NAME/KEY: misc_feature
<222> LOCATION: (14)..(14)
<223> OTHER INFORMATION: Xaa is S8, a-methyl, a-alkenylglycine with 8
      carbon chain

<400> SEQUENCE: 177

Leu Ser Xaa Glu Thr Phe Xaa Asp Leu Trp Lys Leu Leu Xaa Glu Asn
1               5                   10                  15

<210> SEQ ID NO 178
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (8)..(8)
<223> OTHER INFORMATION: Xaa is B8, a-methyl, a-alkenylglycine with two
      8 carbon chain
<220> FEATURE:
<221> NAME/KEY: misc_feature
<222> LOCATION: (15)..(15)
<223> OTHER INFORMATION: Xaa is S8, a-methyl, a-alkenylglycine with 8
```

```
                                    carbon chain

<400> SEQUENCE: 178

Leu Ser Gln Xaa Thr Phe Ser Xaa Leu Trp Lys Leu Leu Ala Xaa Asn
1               5                   10                  15

<210> SEQ ID NO 179
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa is S5, a-methyl, a-alkenylglycine with 5
      carbon chain
<220> FEATURE:
<221> NAME/KEY: misc_feature
<222> LOCATION: (6)..(6)
<223> OTHER INFORMATION: Xaa is B5, a-methyl, a-alkenylglycine with two
      5 carbon chain
<220> FEATURE:
<221> NAME/KEY: misc_feature
<222> LOCATION: (10)..(10)
<223> OTHER INFORMATION: Xaa is R5, an enantiomer of S5, a-methyl,
      a-alkenylglycine with 5 carbon chain

<400> SEQUENCE: 179

Leu Xaa Ile Leu Gln Xaa Ala Val Gln Xaa Ile Leu Gly Leu Glu Gln
1               5                   10                  15

Gln Val Arg Glu Arg
            20

<210> SEQ ID NO 180
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa is S5, a-methyl, a-alkenylglycine with 5
      carbon chain
<220> FEATURE:
<221> NAME/KEY: misc_feature
<222> LOCATION: (13)..(13)
<223> OTHER INFORMATION: Xaa is B5, a-methyl, a-alkenylglycine with two
      5 carbon chain
<220> FEATURE:
<221> NAME/KEY: misc_feature
<222> LOCATION: (17)..(17)
<223> OTHER INFORMATION: Xaa is R5, an enantiomer of S5, a-methyl,
      a-alkenylglycine with 5 carbon chain

<400> SEQUENCE: 180

Leu Leu Ile Leu Gln Gln Ala Val Xaa Val Ile Leu Xaa Leu Glu Gln
1               5                   10                  15

Xaa Val Arg Glu Arg
            20

<210> SEQ ID NO 181
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
```

```
<223> OTHER INFORMATION: Xaa is S5, a-methyl, a-alkenylglycine with 5
      carbon chain
<220> FEATURE:
<221> NAME/KEY: misc_feature
<222> LOCATION: (9)..(9)
<223> OTHER INFORMATION: Xaa is B5, a-methyl, a-alkenylglycine with two
      5 carbon chain
<220> FEATURE:
<221> NAME/KEY: misc_feature
<222> LOCATION: (13)..(13)
<223> OTHER INFORMATION: Xaa is R5, an enantiomer of S5, a-methyl,
      a-alkenylglycine with 5 carbon chain

<400> SEQUENCE: 181

Leu Leu Ile Leu Xaa Gln Ala Val Xaa Val Ile Leu Xaa Leu Glu Gln
1               5                   10                  15

Gln Val Arg Glu Arg
            20

<210> SEQ ID NO 182
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is R5, an enantiomer of S5, a-methyl,
      a-alkenylglycine with 5 carbon chain
<220> FEATURE:
<221> NAME/KEY: misc_feature
<222> LOCATION: (5)..(5)
<223> OTHER INFORMATION: Xaa is B5, a-methyl, a-alkenylglycine with two
      5 carbon chain
<220> FEATURE:
<221> NAME/KEY: misc_feature
<222> LOCATION: (9)..(9)
<223> OTHER INFORMATION: Xaa is S5, a-methyl, a-alkenylglycine with 5
      carbon chain

<400> SEQUENCE: 182

Xaa Asp Phe Ser Xaa Tyr Trp Lys Xaa Leu
1               5                   10

<210> SEQ ID NO 183
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is S5, a-methyl, a-alkenylglycine with 5
      carbon chain
<220> FEATURE:
<221> NAME/KEY: misc_feature
<222> LOCATION: (7)..(7)
<223> OTHER INFORMATION: Xaa is B8, a-methyl, a-alkenylglycine with two
      8 carbon chain
<220> FEATURE:
<221> NAME/KEY: misc_feature
<222> LOCATION: (14)..(14)
<223> OTHER INFORMATION: Xaa is S8, a-methyl, a-alkenylglycine with 8
      carbon chain

<400> SEQUENCE: 183

Leu Ser Xaa Glu Thr Ala Xaa Asp Leu Trp Lys Leu Leu Xaa Glu Asn
1               5                   10                  15

<210> SEQ ID NO 184
```

```
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa is S5, a-methyl, a-alkenylglycine with 5
      carbon chain
<220> FEATURE:
<221> NAME/KEY: misc_feature
<222> LOCATION: (13)..(13)
<223> OTHER INFORMATION: Xaa is B5, a-methyl, a-alkenylglycine with two
      5 carbon chain
<220> FEATURE:
<221> NAME/KEY: misc_feature
<222> LOCATION: (21)..(21)
<223> OTHER INFORMATION: Xaa is S8, a-methyl, a-alkenylglycine with 8
      carbon chain

<400> SEQUENCE: 184

Glu Asp Ile Ile Arg Asn Ile Ala Xaa His Leu Ala Xaa Val Gly Asp
1               5                   10                  15

Trp Asn Leu Asp Xaa Ser Ile
            20

<210> SEQ ID NO 185
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (8)..(8)
<223> OTHER INFORMATION: Xaa is B5, a-methyl, a-alkenylglycine with two
      5 carbon chain
<220> FEATURE:
<221> NAME/KEY: misc_feature
<222> LOCATION: (16)..(16)
<223> OTHER INFORMATION: Xaa is S8, a-methyl, a-alkenylglycine with 8
      carbon chain

<400> SEQUENCE: 185

Asn Ile Ala Xaa His Leu Ala Xaa Val Gly Asp Trp Asn Leu Asp Xaa
1               5                   10                  15

Ser Ile

<210> SEQ ID NO 186
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is S5, a-methyl, a-alkenylglycine with 5
      carbon chain
<220> FEATURE:
<221> NAME/KEY: misc_feature
<222> LOCATION: (5)..(5)
<223> OTHER INFORMATION: Xaa is B5, a-methyl, a-alkenylglycine with two
      5 carbon chain
<220> FEATURE:
<221> NAME/KEY: misc_feature
<222> LOCATION: (13)..(13)
```

<223> OTHER INFORMATION: Xaa is S8, a-methyl, a-alkenylglycine with 8
      carbon chain

<400> SEQUENCE: 186

Xaa His Leu Ala Xaa Val Gly Asp Trp Asn Leu Asp Xaa
1               5                   10

<210> SEQ ID NO 187
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (13)..(13)
<223> OTHER INFORMATION: Xaa is S5, a-methyl, a-alkenylglycine with 5
      carbon chain
<220> FEATURE:
<221> NAME/KEY: misc_feature
<222> LOCATION: (19)..(19)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (26)..(26)
<223> OTHER INFORMATION: Xaa is S5, a-methyl, a-alkenylglycine with 5
      carbon chain

<400> SEQUENCE: 187

Asn Val Lys Arg Arg Xaa His Asn Val Leu Glu Arg Xaa Arg Arg Asn
1               5                   10                  15

Glu Leu Xaa Arg Ser Phe Phe Ala Leu Xaa Asp Gln Ile
            20                  25

<210> SEQ ID NO 188
<211> LENGTH: 38
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is S5, a-methyl, a-alkenylglycine with 5
      carbon chain
<220> FEATURE:
<221> NAME/KEY: misc_feature
<222> LOCATION: (5)..(5)
<223> OTHER INFORMATION: Xaa is B5, a-methyl, a-alkenylglycine with two
      5 carbon chain
<220> FEATURE:
<221> NAME/KEY: misc_feature
<222> LOCATION: (13)..(13)
<223> OTHER INFORMATION: Xaa is S8, a-methyl, a-alkenylglycine with 8
      carbon chain

<400> SEQUENCE: 188

Xaa Tyr Ile Gln Xaa Asn Leu Arg Arg Lys Asn His Xaa His Gln Gln
1               5                   10                  15

Asp Ile Asp Asp Leu Leu Lys Arg Gln Asn Ala Leu Leu Glu Gln Gln
            20                  25                  30

Val Arg Ala Leu Gly Gly
            35

-continued

```
<210> SEQ ID NO 189
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (8)..(8)
<223> OTHER INFORMATION: Xaa is B5, a-methyl, a-alkenylglycine with two
      5 carbon chain
<220> FEATURE:
<221> NAME/KEY: misc_feature
<222> LOCATION: (16)..(16)
<223> OTHER INFORMATION: Xaa is S8, a-methyl, a-alkenylglycine with 8
      carbon chain

<400> SEQUENCE: 189

Asn Ile Ala Xaa His Leu Ala Xaa Val Gly Asp Trp Asn Leu Asp Xaa
1               5                   10                  15

<210> SEQ ID NO 190
<211> LENGTH: 37
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa is S5, a-methyl, a-alkenylglycine with 5
      carbon chain
<220> FEATURE:
<221> NAME/KEY: misc_feature
<222> LOCATION: (13)..(13)
<223> OTHER INFORMATION: Xaa is B5, a-methyl, a-alkenylglycine with two
      5 carbon chain
<220> FEATURE:
<221> NAME/KEY: misc_feature
<222> LOCATION: (20)..(20)
<223> OTHER INFORMATION: Xaa is S8, a-methyl, a-alkenylglycine with 8
      carbon chain

<400> SEQUENCE: 190

Glu Tyr Ile Gln Tyr Asn Leu Arg Xaa Lys Asn His Xaa His Gln Gln
1               5                   10                  15

Asp Ile Asp Xaa Leu Lys Arg Gln Asn Ala Leu Leu Glu Gln Gln Val
            20                  25                  30

Arg Ala Leu Gly Gly
        35

<210> SEQ ID NO 191
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is S5, a-methyl, a-alkenylglycine with 5
      carbon chain
<220> FEATURE:
<221> NAME/KEY: misc_feature
<222> LOCATION: (11)..(11)
<223> OTHER INFORMATION: Xaa is R8, an enantiomer of S8, a-methyl,
      a-alkenylglycine with 8 carbon chain
```

```
<400> SEQUENCE: 191

Ile Gln Asp Xaa Leu Ala Phe Phe Ser Arg Xaa Leu Gln Asn
1               5                   10

<210> SEQ ID NO 192
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain

<400> SEQUENCE: 192

Ala His Leu Xaa Leu Cys Leu Glu Lys Leu Xaa Gly Leu Val Lys
1               5                   10                  15

<210> SEQ ID NO 193
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R8, an enantiomer of S8, a-methyl,
      a-alkenylglycine with 8 carbon chain
<220> FEATURE:
<221> NAME/KEY: misc_feature
<222> LOCATION: (11)..(11)
<223> OTHER INFORMATION: Xaa is S5, a-methyl, a-alkenylglycine with 5
      carbon chain

<400> SEQUENCE: 193

Asn Gln Leu Xaa Phe Ser Arg Phe Ala Leu Xaa Asp Gln Ile
1               5                   10
```

BIOLOGICALLY ACTIVE COMPOUND CONJUGATED TO A STAPLED OR STITCHED PEPTIDE

RELATED APPLICATION

This application is a national stage filing under 35 U.S.C. § 371 of International Patent Application Serial No. PCT/GB2016/054028, filed Dec. 21, 2016, the contents of which is incorporated herein by reference in its entirety.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on May 11, 2021, is named H066470091U500-SUBSEQ-DQP and is 94,142 bytes in size.

The present invention relates to improvements in drug delivery.

More particularly it relates to the use of Cell Penetrating Agents (CPA's), and more particularly still to the use of Cell Penetrating Peptides (CPP's) which have been stabilized by, for example: i) stapling two amino acids to form Stapled CPP's (StaP's) or ii) stitching three or more amino acids to form stitched CPP's (StiP's).

These stabilized CPP's are conjugated to a drug or Biologically Active Compound (BAC) directly or via a Bi-Functional Linker (BFL) so that the BAC can be carried though a cell membrane by the CPP. The resulting molecules are referred to as Drug Carrying Cell Penetrating Molecules (DCCPM's).

The preferred BAC's delivered in this manner are oligonucleotides (ON's), more preferably still electrically low charge carrying oligonucleotides (charge −3 to +3 at pH 7.5) and most preferably electrically neutral oligonucleotides (charge −1 to +1 at pH 7.5), such as, but not limited to, polynucleic acids (PNAs), phosphorodiamidate morpholino oligonucleotides (PMO's) or modified derivatives thereof.

The preferred BFL may be PEGylated, comprising poly ethylene glycol (PEG) groups including modifications such as an amine group, or incorporate a spacer, such as 3-Ala. These modifications can improve solubilisation or provide appropriate spacing between functional moieties.

The invention also relates to a method of facilitating the uptake of a BAC into a cell, the use of a DCCPM in the treatment of a disease requiring alteration of an endogenous or exogenous gene, a method of improving the bioavailability of a drug or BAC, a method of introducing a drug or BAC to a site which is refractory to the drug or BAC in its native state, a method of treating a subject comprising administering the DCCPM's of the invention and to a pharmaceutical composition comprising the DCCPM and one or more pharmaceutically acceptable excipients.

Still further aspects will be apparent from the detailed description.

BACKGROUND TO THE INVENTION

In the treatment of all diseases it is desirable to deliver a drug or BAC into the body, and more preferably into a cell, at a target site, in a manner that ensures a maximal effect with minimal toxicity. This can be challenging.

An example of drugs or BACs which are delivered in a targeted manner are oligonucleotides (ON's), which term includes ON analogues.

ON's can target essential DNA, RNA and protein sequences and can modulate gene expression in a number of ways that includes steric blocking to suppress (i) RNA splicing, (ii) protein translation or (iii) other nucleic acid:nucleic acid or nucleic acid:protein interactions.

Specifically, the hybridisation of ON's to specific RNA sequence motifs prevents correct assembly of the spliceosome, so that it is unable to recognise the target exon(s) in the pre-mRNA and hence excludes these exon in the mature gene transcript. Exclusion of an in-frame exon can lead to a truncated yet functional gene product; exclusion of an out of frame exon results in a frame-shift of the transcript, potentially leading to a premature stop codon and a reduction in the target gene expression level.

Additionally, ON's can be designed to target 5' translation initiation start sites of viral gene transcript(s) to prevent binding of the translational machinery. Using antisense oligonucleotides (ASO) to suppress viral translation is a well-established technology[1] and has progressed into clinical trials for viral haemorrhagic fevers such as Marburg and Ebola[2,3].

Also, ON's can be designed to form aptamers such that the secondary and tertiary structures can bind proteins or other cellular targets thus impacting on specific gene expression levels or other cellular processes (e.g. post-translational modifications).

An advantage of steric blocking based suppression over that of siRNA/RNAi based RNase H-induction of the RNA Induced Silencing Complex is the reduced likelihood of off target side effects.

Modifications of an ON to produce a negatively charged backbone improve stability[4-7], but these backbone chemistries e.g. 2'0-Methyl Phosphothioate analogues, elicit membrane toxicity issues, cause thrombocytopaenia and injection site problems upon clinical translation[8], such that efficacy is prevented by toxicity issues, even when administration protocols become increasingly intermittent[9].

Indeed WO2013/150338 and WO 2014/053622 both disclose delivering negatively charged ON's of small size (typically smaller than 1.5 KDa) by complexing them with positively charged linear or stapled peptides of equal or greater than 15 amino acids and in the range of 15-27 amino acids.

JACS, Vol 136, 2014, G J Hilnski et al, describe stapled and stitched peptides that are able to penetrate cells. Reference is made to the possibility that these peptides could be used to deliver an oligonucleotide, presumably in the same manner as disclosed in the international applications disclosed above, i.e. by complexation. There is nothing to suggest creating new entities of much larger size (greater than 1.5 KDa, through 2.5 KDa, 5 KDa, 7.5 KDa, 10 KDa, 12.5 KDa or more) by covalently linking a BAC with a CPA, optionally via a BFL and indeed, the prior methodology requires the respective components to have opposite charges to facilitate complexing.

The use of electrically low charge carrying oligonucleotides (charge −3 to +3 at pH 7.5) and most preferably electrically neutral oligonucleotides (charge −1 to +1 at pH 7.5), such as, but not limited to, polynucleic acids (PNAs), phosphorodiamidate morpholino oligonucleotides (PMO's), (covalently) conjugated directly or indirectly, using a BFL, was not apparent and indeed, limiting the charge on the ON further allows the use of smaller peptides (less than 15 amino acids in length, through 14, 13, 12, 11, 10, 9, 8, 7, 6 to as few as 4 or 5) as carriers.

The use of uncharged ON backbones, such as phosphorodiamidate morpholino oligonucleotides (PMOs), represent attractive BAC's as they have an impeccable safety record in a preclinical and clinical setting.[2,10-13]

However, their ability to penetrate cells and access their targets is compromised due to their uncharged nature[14].

Overcoming the problem of facilitating their entry into cells is therefore desirable.

Over the last 20 years much research has been dedicated to developing CPA's that facilitate delivery of drugs and BAC's to the biological site of action.

The approach has generally been to use charged peptides as non-covalent complexes to facilitate cell entry of a BAC. Conjugation has also been tried.

WO2014/064258 is an example of the existing conjugating art. A negatively charged ON is coupled to a targeting peptide via a linker. The targeting peptide is a receptor targeting moiety, and not a stapled or stitched peptide, and indeed considerable doubt exists as to whether DNA or RNA molecules can gain cell entry using a receptor targeting moiety as once a negatively charged ON is bound to such a moiety, non-covalent interactions alter its conformation[15].

WO89/03849 discloses oligonucleotide-polyamide conjugates. There is no disclosure of the use of stitched or stapled peptides. The methodology described uses oligonucleotides as a scaffold for the chain extension of peptides and not as a conjugate for delivery, per se.

WO2011/131693 describes nucleic acid constructs which contain a nucleic acid specific for a given target gene and a selective inhibitor of a neurotransmitter transporter. There is no disclosure of the use of stitched or stapled peptides as a delivery agent.

A peptide capable of effecting peptide-mediated cell delivery may also be referred to as a Cell Delivery Peptide (CDP). Examples include: poly arginine, penetratin (based upon an antennapedia homeodomain), or PMO internalization peptides (PIPs).

However, since their first description[16] and given that many CPPs contain multiple arginines, β-alanine and 6-aminohexanoic acid residues, (e.g. poly-Arg12, TAT, Penetratin, Pip6a) [database maintained at crdd.osdd.net/raghava/cpp-site/[17], it is surprising that no CPP-delivered drug has progressed through all phases of clinical trials. In part, this may be because the common arginine-rich core, which makes most CPP's effective, also causes membrane deformities[18] and in higher mammals this manifests as prohibitive toxic side effects, such as tubular degeneration of the kidney[19].

At a physiological pH, and based on pKa of amino acid R groups, a formal charge (FC) can be calculated based on the formula:

$$FC = V - N - \frac{B}{2}$$

Where, V=valence electrons of the neutral atom in isolation; N=the number of non-bonding valence electrons on the defined atom; B=the total number of electrons shared in bonds.

Indeed, based on this, the CPPs typically used to date harbour many positively charged residues. It has been shown that there is a correlation between this positive charge and membrane toxicity[20].

Therefore, CPPs with a lower amount of positively charged residues within the amino acid sequence, whilst retaining the ability to cross a biological membrane, will be more clinically relevant.

The Applicant has overcome this major impediment by utilising stabilized CPA's. By linking a drug or BAC to a stabilized CPA, including stitched and stapled peptides, they have surprisingly obtained enhanced cellular uptake dynamics, 10-20 fold better than current state of the art for CPA[21,22].

They have illustrated this by delivering an ON targeted to repair a gene producing dystrophin. Targeting specific genes with ON is of course in itself known, as illustrated by, for example, WO2009/054725 and WO2010/123369. These publications however use a negatively charged backbone and deliver the cargo directly or using complexation.

One way to prepare stapled and stitched peptides, two linked amino acids (stapled) or three or more linked amino acids (stitched), is to incorporate amino acids into the peptide that are modified to bear e.g. an olefin (alkene) group (which may be incorporated at defined relative positions during solid-phase peptide synthesis). For example, on-resin ring-closing metathesis is then used to close one (stapled [denoted as StaP herein]) or two or more (stitched [denoted as StiP herein]) all-hydrocarbon cross-links that induce the peptide to adopt a stabilised structure, typically, but not essentially an alpha helix. For StaP's, it is preferred to use either one or both enantiomers of the un-natural amino acids, termed the S5 (S-pentenylalanine) or R5 (R-pentenylalanine), or the S8 (S-octenylalanine) or R8 (R-octenylalanine), depending on the stereo-chemical configuration. For StiP's, a further un-natural olefin-bearing α,α-di-substituted amino acid (B5 or B8) is utilised. Cross linking strategies are however not restricted to ring-closing metathesis of un-natural olefin-bearing α,α-di-substituted amino acids. Other cross-linking chemistry's may be used to stabilize the peptide, such as ring-closing metathesis between O-allylserine analogues (S-OAS or R-OAS).

The cellular entry dynamics of existing CPAs and the StiP's and StaP's differ. Traditional CPPs enter cells via energy-independent direct plasma membrane translocation or via energy-dependent, clathrin and caveolin-mediated endocytosis; whereas the StiP's and StaP's utilised in the invention enter via an energy dependent, but clathrin and caveolin independent mechanism[21,23]. Given that StiP's and StaP's uptake is abrogated with reduced cellular decoration of heparin sulphate[21] a macropinocytotic entry mechanism is infered[24], suggesting this altered entry mechanism enables enhanced cellular uptake and bio-distribution compared to the state of the art.

Relative to their unmodified peptide precursors, StaP's and StiP's generally exhibit robust cellular uptake, significant resistance to proteolytic degradation, and in vivo stability that can support a half-life of more than 12 hours in non-human primates[25]. It is likely that this increase in drug-likeness stems from the highly rigidified structure and the burial of the backbone amide bonds in the core of e.g. the α-helix. This structural rigidity also decreases the likelihood that StiP's and StaP's will be immunogenic, as the design of major histocompatibility complexes is such that peptides must adopt an extended conformation to be presented. The potential reduced or lack of membrane toxicity and immunogenicity enhances the clinical translatability of compounds when conjugated to drugs and BAC's such as ON's.

The BAC and CPP can be covalently conjugated directly, or covalently conjugated via a BFL. Many functional groups may be used for conjugation reactions.

ONs can be used to induce a steric block to any gene in humans, animals and lower order organisms and thus can be applied to natural disease (including genetic and age-related diseases) or acquired diseases in humans and animals.

For example, viral haemorrhagic fevers (VHFs) are animal-borne illnesses in which a prolonged inflammatory cytokine response leads to the gradual destruction of veins and arteries. Causes of VHF include Ebola and Marburg viruses and several Arena viruses; these diseases are presently considered untreatable. Viral haemorrhagic fevers are characterized by high fever and bleeding disorders, and can cause death by shock and organ failure. ASOs can be designed to target 5' translation initiation start sites of viral gene transcript(s) to prevent binding of the translational machinery. Using ASO to suppress viral translation is a well-established technology[1] and has progressed into clinical trials for viral haemorrhagic fevers such as Marburg and Ebola[2,3]. One PMO, AVI-7537 was evaluated for human use in the West African Ebola outbreak in 2014-15.

Some tissues are particularly refractory to naked PMO transfection, e.g. heart, which may reflect differential vesicle-mediated PMO uptake mechanisms[23]. In fact, direct intra-cardiac injection of naked PMO does not even lead to efficient transfection[26], and refractory tissues tend to require repeat administration or high dose strategies[27-23]. However, whilst CPP conjugation improves PMO bio-distribution and serum stability[36-32], toxicity is still a major roadblock for pipeline development[19].

For effective clinical translation of steric blocking ASOs, CPPs need to effectively deliver the BAC to either the cytoplasm or nucleoplasm whilst limiting any toxicity associated with cell entry.

Thus, providing DCCPM's which are able to deliver a drug or BAC more efficiently or to a target site, or with lower toxicity and immunogenicity would be highly desirable.

BRIEF SUMMARY OF THE DISCLOSURE

In accordance with a first aspect of the present invention there is provided a drug carrying cell penetrating molecule (DCCPM) comprising:

i. a biologically active compound (BAC), and ii. a cell penetrating agent (CPA), which BAC and CPA are linked directly or via a bi-functional linker (BFL), and wherein the CPA is a stabilized peptide (CPP) which has a conformation imposed upon it by stapling to form a stapled peptide (StaP) or stitching to form a stitched peptide (StiP).

A stapled peptide (StaP) may be formed by, for example, stapling two conformationally adjacent amino acids together, and a stitched peptide (StiP) may be formed by, for example, stitching at least three conformationally adjacent amino acids to form a stitched peptide (StiP).

The stapling or stitching results in the formation of a cross link or bridge between two conformationally adjacent amino acids of the peptide.

In a preferred embodiment the cross link or bridge comprises two components, a hydrocarbon bridge and a terminal methyl group. The hydrocarbon bridge may be composed of a double hydrocarbon bond or a single hydrocarbon bond.

The CPP preferably comprises at least two un-natural amino acids bearing all-hydrocarbon tethers (e.g. α-methyl, α-pentenyl glycine).

The preferred stapled or stitched CPPs incorporate one or more of: a (S)-pentenylalanine (S5) or its enantiomer (R5), a S-octenylalanine (S8) or its enantiomer (R8) or combinations thereof (e.g. R-octenylalanine/S-pentenylalanine (R8/S5) or S-octenylalanine/R-pentenylalanine (S8/R5).

The preferred unnatural amino acids incorporated into the CPPs and reacted to form a cross link or bridge between them are illustrated in Table 1 and some exemplary and preferred resulting CPPs are illustrated in Table 2.

TABLE 1

| Unnatural Amino Acids | | |
|---|---|---|
| 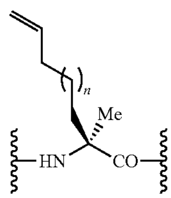  S5: n = 1 S8: n = 4 | 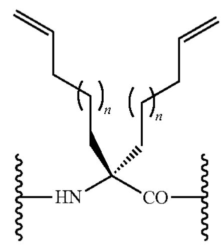  B5: n = 1 B8: n = 4 | 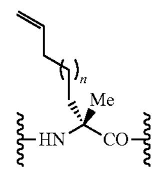  R5: n = 1 R8: n = 4 |
| 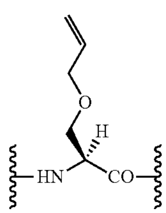  S-OAS | 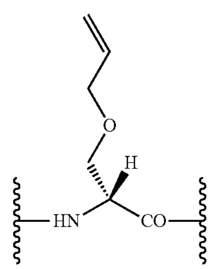  R-OAS | |

TABLE 2

| Entry | Peptide Sequence | Length | Peptide Type |
|---|---|---|---|
| 3 | TRQARRNRRRRWRRAAAA | 18 | Non RCM |
| 4 | TRQARRNRRRRWRERQR | 17 | Non RCM |
| 5 | RQIKIWFQNRRMKWKK | 16 | Non RCM |
| 6 | RRRRRRRRWRRR | 12 | Non RCM |
| 7 | LSQETFSDLWKLLPEN | 16 | Non RCM |
| 8 | NQLKRSFFALRDQI | 14 | Non RCM |
| 8 | NQLKRSFFALRDQI | 14 | Non RCM |
| 9 | TILKASVDYIRKLQREQQRAKEL | 23 | Non RCM |

TABLE 2-continued

| Entry | Peptide Sequence | Length | Peptide Type |
|---|---|---|---|
| 6 | RRRRRRRRWRRR | 12 | Non RCM |
| 10 | RRRRRRRRRRRR | 12 | Non RCM |
| 11 | YGRKKRRQRRRP | 12 | Non RCM |
| 12 | RKFKRLFQ | 8 | Non RCM |
| 13 | NELKRSFFALRDQI | 14 | Non RCM |
| 14 | NQL-R8-RS-FFAL-S5-DQI | 14 | Non RCM |
| 15 | KNHTHQQDI | 9 | Non RCM |
| 16 | NELKRSFFALRDQIPSLQGEKASRAQILDKATEYIQYNLRRK | 42 | Non RCM |
| 17 | KATEYIQYNLRRKNHTHQQDIDDL | 24 | Non RCM |
| 18 | ASTLFETFYLGGLLG | 15 | Non RCM |
| 19 | RRGSRPSGA-S5-RRR-S5-R | 15 | Non RCM |
| 20 | FNINDRIKELGTLI | 14 | Non RCM |
| 21 | DHIKDSFHSLRDSVPSLQGEKASRAQILDKATEYIQYNLRRK | 42 | Non RCM |
| 22 | EYIQYNLRKNHTHQQDIDDLKRQNALLEQQVRALGG | 36 | Non RCM |
| 23 | SSLFERFYNLVTPAGG | 16 | Non RCM |
| 24 | NSSFADFFHTVPYNLL | 16 | Non RCM |
| 25 | TRQARRN-S5-RRR-S5-RR | 14 | Non RCM |
| 26 | RRGSRPSGA-S5-RRR-S5-RAAAA | 19 | i, i + 4 Staple |
| 27 | S5-RRQ-S5-RRDRQRRRRR | 15 | i, i + 4 Staple |
| 28 | TRQ-S5-RRQ-S5-RRRWRERQR | 17 | i, i + 4 Staple |
| 29 | SEELV-S5-EAH-S5-LCTLLENAIQDTVREQ | 26 | i, i + 4 Staple |
| 30 | SEELVAEAH-S5-LCT-S5-LENAIQDTVREQ | 26 | i, i + 4 Staple |
| 31 | SEELVAEAHNLCTLLE-S5-AIQ-S5-TVREQ | 26 | i, i + 4 Staple |
| 32 | DRRQRRR-S5-RQR-S5-RRR | 15 | i, i + 4 Staple |
| 33 | S5-RRQ-S5-RRRRQRRRRR | 15 | i, i + 4 Staple |
| 34 | S-S5-ELV-S5-EAHNLCTLLENAIQDTVREQ | 26 | i, i + 4 Staple |
| 35 | SEELVAEA-S5-NLC-S5-LLENAIQDTVREQ | 26 | i, i + 4 Staple |
| 36 | SEELVAEAHNLC-S5-LLE-S5-AIQDTVREQ | 26 | i, i + 4 Staple |
| 37 | SEELVAEAHNLCTLLENAI-S5-DTV-S5-EQ | 26 | i, i + 4 Staple |
| 38 | FS-S5-LWK-S5-L | 8 | i, i + 4 Staple |
| 39 | FM-S5-YWK-S5-L | 8 | i, i + 4 Staple |
| 40 | QTFS-S5-LWK-S5-L | 10 | i, i + 4 Staple |
| 41 | PPKKFR-S5-LFF-S5-S | 12 | i, i + 4 Staple |
| 42 | KK-pff-R-S5-LFF-S5-S | 10 | i, i + 4 Staple |
| 43 | RK-pff-S5-RLF-S5-SY | 10 | i, i + 4 Staple |
| 44 | RKF-S5-RLF-S5-SY | 10 | i, i + 4 Staple |
| 45 | R-pff-K-S5-RLF-S5-SY | 10 | i, i + 4 Staple |
| 46 | AM-S5-YVVK-S5-L | 8 | i, i + 4 Staple |

TABLE 2-continued

| Entry | Peptide Sequence | Length | Peptide Type |
|---|---|---|---|
| 47 | QTFSD-R5-WK-S5-L | 10 | i, i + 4 Staple |
| 48 | KKFR-S5-LFF-S5-S | 10 | i, i + 4 Staple |
| 49 | RRLFR-S5-NLFL-S5-T | 12 | i, i + 4 Staple |
| 50 | RR-pff-S5-RLF-S5-SY | 10 | i, i + 4 Staple |
| 51 | RKA-S5-RLF-S5-SY | 10 | i, i + 4 Staple |
| 43 | RK-pff-S5-RLF-S5-SY | 10 | i, i + 4 Staple |
| 52 | S5-RLF-S5-SY | 7 | i, i + 4 Staple |
| 53 | KQKRKFS-S5-FFK-S5-L | 13 | i, i + 4 Staple |
| 54 | KQKRK-pff-S-S5-FFK-S5-L | 13 | i, i + 4 Staple |
| 54 | KQKRK-pff-S-S5-FFK-S5-L | 13 | i, i + 4 Staple |
| 55 | KF-S5-RLF-S5 | 7 | i, i + 4 Staple |
| 56 | S5-RLF-S5 | 5 | i, i + 4 Staple |
| 57 | RKF-S5-RLF-S5 | 8 | i, i + 4 Staple |
| 58 | KQKRKFS-S5-FFK-S5-LV | 13 | i, i + 4 Staple |
| 59 | KQ-pff-RKKS-S5-FFK-S5-L | 13 | i, i + 4 Staple |
| 60 | RK-pff-S5-RLF-S5 | 8 | i, i + 4 Staple |
| 61 | F-S5-RLF-S5 | 6 | i, i + 4 Staple |
| 62 | KTYRGAFQ-S5-LFQ-S5-VRE | 16 | i, i + 4 Staple |
| 63 | STALR-S5-LIE-S5-LVNITQNQKAPL | 22 | i, i + 4 Staple |
| 64 | STALRELI-S5-ELV-S5-ITQNQKAPL | 22 | i, i + 4 Staple |
| 65 | STALRELIEEL-S5-NIT-S5-NQKAPL | 22 | i, i + 4 Staple |
| 66 | NELK-S5-SFF-S5-LRDQIPELENNEKAP | 24 | i, i + 4 Staple |
| 67 | LENRQ-S5-KLE-S5-ANRHLL | 16 | i, i + 4 Staple |
| 68 | IL-S5-ASV-S5-YIRKLQREQ | 16 | i, i + 4 Staple |
| 69 | FNI-S5-DRI-S5-ELGTLI | 14 | i, i + 4 Staple |
| 70 | KN-S5-THQ-S5-DI | 9 | i, i + 4 Staple |
| 71 | STALRELIEE LV-S5-ITQ-S5-QKAPL | 21 | i, i + 4 Staple |
| 72 | NELK-S5-SFF-S5-LRDQI | 14 | i, i + 4 Staple |
| 73 | LENRQKKLE-S5-ANR-S5-LL | 16 | i, i + 4 Staple |
| 74 | ILKAS-S5-DYI-S5-KLQREQ | 16 | i, i + 4 Staple |
| 75 | DHIK-S5-SFH-S5-LRDSV | 14 | i, i + 4 Staple |
| 76 | DHIKDSF-S5-SLR-S5-SV | 14 | i, i + 4 Staple |
| 77 | S5-Y1Q-S5-NLRRKNHTHQQDIDDLLKRQNALLEQQVRALGG | 38 | i, i + 4 Staple |
| 78 | TYRGAAQ-S5-AAQ-S5-VREV | 16 | i, i + 4 Staple |
| 79 | TY-S5-GAF-S5-NLFQSVREV | 16 | i, i + 4 Staple |
| 80 | A-S5-SVF-S5-NYFHSVPYFEL | 17 | i, i + 4 Staple |
| 81 | GAF-S5-NLF-S5-SV | 10 | i, i + 4 Staple |
| 82 | S5-GAF-S5-NLF-R5-SV | 11 | i, i + 4 Staple |

TABLE 2-continued

| Entry | Peptide Sequence | Length | Peptide Type |
|---|---|---|---|
| 83 | SYRGAFQ-S5-LFQ-S5-VREV | 16 | i, i + 4 Staple |
| 84 | SSVFY-S5-YFH-S5-VPYFEL | 16 | i, i + 4 Staple |
| 85 | A-S5-TLF-S5-TFYLGGLLG | 15 | i, i + 4 Staple |
| 86 | S5-GAF-S5-NLFQSV | 11 | i, i + 4 Staple |
| 87 | A-S5-SSF-S5-DFFHTVPYNLL | 17 | i, i + 4 Staple |
| 88 | ERLRRRI-S5-LCR-S5-HHST | 16 | i, i + 4 Staple |
| 89 | ERLRRRI-S5-NLCR-S5-HHST | 17 | i, i + 4 Staple |
| 90 | ERLRRRL-S5-LCR-S5-HHST | 16 | i, i + 4 Staple |
| 91 | ERLRRRF-S5-LCR-S5-HHST | 16 | i, i + 4 Staple |
| 92 | ERFRRRI-S5-LCR-S5-HHST | 16 | i, i + 4 Staple |
| 93 | ERLARRI-S5-LCR-S5-HHST | 16 | i, i + 4 Staple |
| 94 | ENPESILD-S5-HVQ-S5-VM | 15 | i, i + 4 Staple |
| 95 | PE-S5-ILD-S5-HVQRVM | 13 | i, i + 4 Staple |
| 96 | ERLRRRI-S5-FCR-S5-HHST | 16 | i, i + 4 Staple |
| 97 | ERLRRRNL-S5-LCR-S5-HHST | 17 | i, i + 4 Staple |
| 98 | ERNLRRRI-S5-LCR-S5-HHST | 17 | i, i + 4 Staple |
| 99 | ERWRRRI-S5-LCR-S5-HHST | 16 | i, i + 4 Staple |
| 100 | RELRREI-S5-LCR-S5-HHST | 16 | i, i + 4 Staple |
| 101 | ENPE-S5-ILD-S5-HVQRVM | 15 | i, i + 4 Staple |
| 102 | NPE-S5-ILD-S5-HVQRVM | 14 | i, i + 4 Staple |
| 103 | WPE-S5-ILD-S5-HVQRVM | 14 | i, i + 4 Staple |
| 104 | PE-S5-ILD-S5-HVRRVMR | 14 | i, i + 4 Staple |
| 105 | RPE-S5-ILD-S5-HVRRVMR | 15 | i, i + 4 Staple |
| 106 | TRQA-R8-RNRRRR-S5-RR | 14 | i, i + 7 Staple |
| 107 | RRGSRPSGA-R8-RRRRRA-S5 | 17 | i, i + 7 Staple |
| 108 | RRGSRPSGA-R8-RRRRRA-S5-AA | 19 | i, i + 7 Staple |
| 109 | TRQARRN-R8-RRRWRE-S5-QR | 17 | i, i + 7 Staple |
| 110 | RRRR-R5-RRRWRR-S8 | 12 | i, i + 7 Staple |
| 111 | KPE-S5-ILD-S5-HVQRVM | 14 | i, i + 7 Staple |
| 112 | WPE-S5-ILD-S5-HVRRVMR | 15 | i, i + 7 Staple |
| 113 | RRRR-R8-RQRRRR-S5-RR | 14 | i, i + 7 Staple |
| 114 | RRGSRPSGA-R8-RRRRRR-S5 | 17 | i, i + 7 Staple |
| 115 | R8-RRQRRR-S5-RQRRRRR | 15 | i, i + 7 Staple |
| 109 | TRQARRN-R5-RRRWRE-S8-QR | 17 | i, i + 7 Staple |
| 116 | RRRR-R5-RRRRRR-S8 | 12 | i, i + 7 Staple |
| 117 | YGRK-R5-RRQRRR-S8 | 12 | i, i + 7 Staple |
| 118 | S-R8-ELVAEA-S5-NLCTLLENAIQDTVREQ | 25 | i, i + 7 Staple |
| 119 | SEELVAEAH-R8-LCTLLE-S5-AIQDTVREQ | 26 | i, i + 7 Staple |
| 120 | SEELVAEAHNLCT-R8-LENAIQ-S5-TVREQ | 26 | i, i + 7 Staple |

TABLE 2-continued

| Entry | Peptide Sequence | Length | Peptide Type |
|---|---|---|---|
| 121 | RQIKIW-R5-QNRRMK-S8-KK | 16 | i, i + 7 Staple |
| 110 | RRRR-R5-RRRWRR-S8 | 12 | i, i + 7 Staple |
| 118 | S-R8-ELVAEA-S5-NLCTLLENAIQDTVREQ | 26 | i, i + 7 Staple |
| 122 | SE-R8-LVAEAH-S5-LCTLLENAIQDTVREQ | 26 | i, i + 7 Staple |
| 123 | SEELVAEAHNLC-R8-LLENAI-S5-DTVREQ | 26 | i, i + 7 Staple |
| 124 | SEELVAEAHNLCTLLE-R8-AIQDT V-S5-EQ | 26 | i, i + 7 Staple |
| 125 | LSQETF-R8-DLWKLL-S5-EN | 16 | i, i + 7 Staple |
| 126 | ILR-R8-AVSHMK-S5-LRGT | 15 | i, i + 7 Staple |
| 126 | ILR-R8-AVSHMK-S5-LRGT | 15 | i, i + 7 Staple |
| 127 | NEL-R8-RS FRSL-S5-DSI | 14 | i, i + 7 Staple |
| 128 | NEL-R8-RS FRAL-S5-DQI | 14 | i, i + 7 Staple |
| 129 | NEL-R8-RS FFAL-S5-DSI | 14 | i, i + 7 Staple |
| 130 | NEL-R8-RS FFAL-S5-DQI | 14 | i, i + 7 Staple |
| 131 | IL-R8-MA-VSHM-S5-SLRGT | 15 | i, i + 7 Staple |
| 132 | NEL-R8-RS FRAL-S5-DSI | 14 | i, i + 7 Staple |
| 133 | NEL-R8-RS FFSL-S5-DQI | 14 | i, i + 7 Staple |
| 134 | WNEL-R8-RSFRSL-S5-DQI | 15 | i, i + 7 Staple |
| 135 | NQR-R8-LSFFAL-S5-DQI | 14 | i, i + 7 Staple |
| 14 | NQL-R8-RSFFAL-S5-DQI | 14 | i, i + 7 Staple |
| 135 | NQR-R8-LSFFAL-S5-DQI | 14 | i, i + 7 Staple |
| 136 | NQL-R8-LSFFAR-S5-DQI | 14 | i, i + 7 Staple |
| 137 | NKL-R8-RS FFAL-S5-DQI | 14 | i, i + 7 Staple |
| 130 | NEL-R8-RS FFAL-S5-DQI | 14 | i, i + 7 Staple |
| 138 | NELK-R8-SFFALR-S5-QIPELENNEKAP | 24 | i, i + 7 Staple |
| 139 | AHL-R8-LCLEKL-S5-GLV | 14 | i, i + 7 Staple |
| 14 | NQL-R8-RSFFAL-S5-DQI (D-amino acids) | 14 | i, i + 7 Staple |
| 191 | IQD-S5-LAFFSR-R8-LQN (D-amino acids) | 14 | i, i + 7 Staple |
| 140 | NKL-R8-RS-FKAL-S5-KQI | 14 | i, i + 7 Staple |
| 141 | NELK-R8-S-FFALR-S5-QI | 14 | i, i + 7 Staple |
| 142 | NQL-R8-RS-FFAL-S5-DQIPELENNEKAP | 24 | i, i + 7 Staple |
| 14 | NQL-R8-RSFFAL-S5-DQI | 14 | i, i + 7 Staple |
| 192 | AHL-R8-LCLEKL-S5-GLV-(K-(PEG)1- | 15 | i, i + 7 Staple |
| 143 | KV-R8-ILK KAT-S5-YILS | 14 | i, i + 7 Staple |
| 144 | R8-KR RAHA-S5-AERARR | 14 | i, i + 7 Staple |
| 191 | IQD-S5-LAFFSR-R8-LQN (D-amino acids) | 14 | i, i + 7 Staple |
| 14 | NQL-R8-RSFFAL-S5-DQI (D-amino acids) | 14 | i, i + 7 Staple |
| 14 | NQL-R8-RS-FFAL-S5-DQI | 14 | i, i + 7 Staple |
| 14 | NQL-R8-RSFFAL-S5-DQI | 14 | i, i + 7 Staple |
| 145 | EENAKRR-R8-HNALER-S5-RR | 17 | i, i + 7 Staple |

TABLE 2-continued

| Entry | Peptide Sequence | Length | Peptide Type |
|---|---|---|---|
| 193 | NQL-R8-FSRFAL-S5-DQI (D-amino acids) | 14 | i, i + 7 Staple |
| 146 | NQL-R8-LS-S5-DQI | 10 | i, i + 7 Staple |
| 147 | NQL-R8-FS-S5-DQI | 10 | i, i + 7 Staple |
| 148 | TILKASVDYIRKL-R8-REQQRA-S5-EL | 23 | i, i + 7 Staple |
| 149 | FNI-R8-DRI-S5-TLI | 11 | i, i + 7 Staple |
| 150 | RNI-R8-DRI-S5-TRI | 11 | i, i + 7 Staple |
| 151 | KATEYIQYNLRRKN-R8-THQQDI-S5-DL | 24 | i, i + 7 Staple |
| 152 | NEL-R8-RSFFAL-S5-DQIDQIPAAKRVKLD | 26 | i, i + 7 Staple |
| 14 | NQL-R8-RSFFAL-S5-DQI | 14 | i, i + 7 Staple |
| 153 | RNI-R8-DRIKEL-S5-TLI | 14 | i, i + 7 Staple |
| 154 | FNIN-R8-RIKELG-S5-LI | 14 | i, i + 7 Staple |
| 155 | FNI-R8-DRIKEL-S5-TRI | 14 | i, i + 7 Staple |
| 156 | NQL-R8-RSFRAL-S5-DQI | 15 | i, i + 7 Staple |
| 157 | NEL-R8-RSFFAL-S5-DQIDQIPKKKRKV | 24 | i, i + 7 Staple |
| 158 | ENPE-R8-ILDEHV-S5-RVM | 15 | i, i + 7 Staple |
| 164 | S8-RQARRN-B5-RRRWRE-S8-QR | 16 | i, i + 4, i + 11 Stitch Reduced |
| 163 | TRQ-S5-RRN-B5-RRRWRE-S8-QR | 17 | i, i + 4, i + 11 Stitch |
| 159 | TRQ-S5-RRA-B5-RRRWRE-S8-QR | 17 | i, i + 4, i + 11 Stitch |
| 160 | S5-RRN-B5-RRRWRE-S8 | 12 | i, i + 4, i + 11 Stitch |
| 161 | EYIQ-R5-NLRRKNH-S8-HQQDIDDLKRQNALLEQQVRALGG | 37 | i, i + 4, i + 11 Stitch |
| 165 | S8-RQARRQ-B5-RRRWRE-S8-QR | 17 | i, i + 4, i + 11 Stitch Reduced |
| 162 | TRQ-S5-Q-B5-RRRWRE-S8-QR | 15 | i, i + 4, i + 11 Stitch |
| 163 | TRQ-S5-RRN-B5-RRRWRE-S8-QR | 17 | i, i + 4, i + 11 Stitch Reduced |
| 164 | R8-RQARRN-B5-RRRWRE-S8-QR | 17 | i, i + 4, i + 11 Stitch Reduced |
| 165 | R8-RQARRQ-B5-RRRWRE-S8-QR | 17 | i, i + 4, i + 11 Stitch |
| 166 | S5-RRN-B5-RRRWRR-S8 | 12 | i, i + 4, i + 11 Stitch |
| 167 | RRA-B5-RRRWRR-S8 | 11 | i, i + 4, i + 11 Stitch |
| 169 | S5-RRR-B5-RRRRRR-S8 | 12 | i, i + 4, i + 11 Stitch |
| 168 | S5-KIW-B5-QNRRNLK-S8 | 13 | i, i + 4, i + 11 Stitch |
| 169 | S5-RRR-B5-RRRRRR-S8 | 12 | i, i + 4, i + 11 Stitch |
| 170 | S5-GRK-B5-RRQRRR-S8 | 12 | i, i + 4, i + 11 Stitch |
| 171 | S5-RRQ-B5-RRRWRR-S8 | 12 | i, i + 4, i + 11 Stitch |
| 174 | S5-RRR-B5-RRRWRR-S8 | 12 | i, i + 4, i + 11 Stitch |
| 172 | RQ-S5-KIW-B5-QNRRMK-S8-KK | 16 | i, i + 4, i + 11 Stitch |
| 173 | S5-KIW-B5-QNRRAK-S8 | 12 | i, i + 4, i + 11 Stitch |
| 174 | S5-RRR-B5-RRRWRR-S8 | 12 | i, i + 4, i + 11 Stitch |
| 175 | L-S5-ILQ-B5-AVQVIL-S8-LEQQVRER | 21 | i, i + 4, i + 11 Stitch |

TABLE 2-continued

| Entry | Peptide Sequence | Length | Peptide Type |
|---|---|---|---|
| 176 | LLILQQAV-S5-VIL-B5-LEQQVR-S8-R | 21 | i, i + 4, i + 11 Stitch |
| 182 | S5-DFS-B5-YWK-R5-L | 10 | i, i + 4, i + 11 Stitch |
| 177 | LS-S5-ETF-B8-DLWKLL-S8-EN | 16 | i, i + 4, i + 11 Stitch |
| 178 | LSQ-S5-TFS-B8-LWKLLA-S8-N | 16 | i, i + 4, i + 11 Stitch |
| 179 | L-S5-ILQ-B5-AVQ-R5-ILGLEQQVRER | 21 | i, i + 4, i + 11 Stitch |
| 180 | LLILQQAV-S5-VIL-B5-LEQ-R5-VRER | 21 | i, i + 4, i + 11 Stitch |
| 181 | LLIL-S5-QAV-B5-VIL-R5-LEQQVRER | 21 | i, i + 4, i + 11 Stitch |
| 182 | R5-DFS-B5-YVVK-S5-L | 10 | i, i + 4, i + 11 Stitch |
| 183 | LS-S5-ETA-B8-DLWKLL-S8-EN | 16 | i, i + 4, i + 11 Stitch |
| 184 | EDIIRNIA-S5-HLA-B5-VGDWNLD-S8-SI | 23 | i, i + 4, i + 11 Stitch |
| 185 | NIA-S5-HLA-B5-VGDWNLD-S8-SI (isomer 2) | 18 | i, i + 4, i + 11 Stitch |
| 186 | S5-HLA-B5-VGDWNLD-S8 (isomer 1) | 13 | i, i + 4, i + 11 Stitch |
| 187 | NVKRR-R8-HNVLER-S5-RRNEL-R8-RSFFAL-S5-DQI | 29 | i, i + 4, i + 11 Stitch |
| 188 | S5-Y1Q-B5-NLRRKNH-S8-HQQDIDDLLKRQNALLEQQVRALGG | 38 | i, i + 4, i + 11 Stitch |
| 185 | NIA-S5-HLA-B5-VGDWNLD-S8-SI | 18 | i, i + 4, i + 11 Stitch |
| 189 | NIA-S5-HLA-B5-VGDWNLD-S8 | 16 | i, i + 4, i + 11 Stitch |
| 186 | S5-HLA-B5-VGDWNLD-S8 | 13 | i, i + 4, i + 11 Stitch |
| 190 | EYIQYNLR-S5-KNH-B5-HQQDID-S8-LKRQNALLEQQVRALGG | 37 | i, i + 4, i + 11 Stitch |

S5 = a-methyl, a-alkenylglycine with 5 carbon chain
S8 = a-methyl, a-alkenylglycine with 8 carbon chain
B5 = a-methyl, a-alkenylglycine with two 5 carbon chain Alternative CPPs and their method of manufacture are disclosed in Chu et al, 2014 and associated supplementary information, and are incorporated by reference[21].

The exemplified stabilized peptide comprises two or more olefin bearing side chains that are covalently formed, typically by means of a ring-closing metathesis.

The stabilized conformation typically comprises at least one alpha helix. It may however, in the alternative, comprise at least one turn (for example, but not limited to, α, β, γ, δ or π), several turns to form a beta sheet, or a combination of one or more of: an alpha helix, turn, or beta sheet.

The formal charge of a CPP is calculated at physiological pH (about 7.5) and is based on the pKa of amino acid R groups. These values ($pK_x$) are represented in Table 3.

TABLE 3

| Name | 3-Letter Symbol | 1-Letter Symbol | Molecular Weight | Molecular Formula | Residue Formula | Residue Weight ($-H_2O$) | pKa1 | pKb2 | pKx3 | pI4 |
|---|---|---|---|---|---|---|---|---|---|---|
| Alganine | Ala | A | 89.10 | $C_3H_7NO_2$ | $C_3H_5NO$ | 71.08 | 2.34 | 9.69 | — | 6.00 |
| Arginine | Arg | R | 174.20 | $C_6H_{14}N_4O_2$ | $C_6H_{12}N_4O$ | 156.19 | 2.17 | 9.04 | 12.48 | 10.76 |
| Asparagine | Asn | N | 132.12 | $C_4H_8N_2O_3$ | $C_4H_6N_2O_2$ | 114.11 | 2.02 | 8.80 | — | 5.41 |
| Aspartic Acid | Asp | D | 133.11 | $C_4H_7NO_4$ | $C_4H_5NO_3$ | 115.09 | 1.88 | 9.60 | 3.65 | 2.77 |
| Cysteine | Cys | C | 121.16 | $C_3H_7NO_2S$ | $C_3H_5NOS$ | 103.15 | 1.96 | 10.28 | 8.18 | 5.07 |
| Glutamic acid | Glu | E | 147.13 | $C_5H_9NO_4$ | $C_5H_7NO_3$ | 129.12 | 2.19 | 9.67 | 4.25 | 3.22 |
| Glutamine | Gln | Q | 146.15 | $C_5H_{10}N_2O_3$ | $C_5H_8N_2O_2$ | 128.13 | 2.17 | 9.13 | — | 5.65 |
| Glycine | Gly | G | 75.07 | $C_2H_5NO_2$ | $C_2H_3NO$ | 57.05 | 2.34 | 9.60 | — | 5.97 |
| Histidine | His | H | 155.16 | $C_6H_9N_3O_2$ | $C_6H_7N_3O$ | 137.14 | 1.82 | 9.17 | 6.00 | 7.59 |
| Hydroxyproline | Hyp | O | 131.13 | $C_5H_9NO_3$ | $C_5H_7NO_2$ | 113.11 | 1.82 | 9.65 | — | — |

TABLE 3-continued

| Name | 3-Letter Symbol | 1-Letter Symbol | Molecular Weight | Molecular Formula | Residue Formula | Residue Weight (—$H_2O$) | pKa1 | pKb2 | pKx3 | pI4 |
|---|---|---|---|---|---|---|---|---|---|---|
| Isoleucine | Ile | I | 131.18 | $C_6H_{13}NO_2$ | $C_6H_{11}NO$ | 113.16 | 2.36 | 9.60 | — | 6.02 |
| Leucine | Leu | L | 131.18 | $C_6H_{13}NO_2$ | $C_6H_{11}NO$ | 113.16 | 2.36 | 9.60 | — | 5.98 |
| Lysine | Lys | K | 146.19 | $C_6H_{14}N_2O_2$ | $C_6H_{12}N_2O$ | 128.18 | 2.18 | 8.95 | 10.53 | 9.74 |
| Methionine | Met | M | 149.21 | $C_5H_{11}NO_2S$ | $C_5H_{11}NOS$ | 131.20 | 2.28 | 9.21 | — | 5.74 |
| Phenylalanine | Phe | F | 165.19 | $C_9H_{11}NO_2$ | $C_9H_9NO$ | 147.18 | 1.83 | 9.13 | — | 5.48 |
| Proline | Pro | P | 115.13 | $C_5H_9NO_2$ | $C_5H_7NO$ | 97.12 | 1.99 | 10.60 | — | 6.30 |
| Pyroglutamatic | Glp | U | 139.11 | $C_5H_7NO_3$ | $C_5H_5NO_2$ | 121.09 | — | — | — | 5.68 |
| Serine | Ser | S | 105.09 | $C_3H_7NO_3$ | $C_3H_5NO_2$ | 87.08 | 2.21 | 9.15 | — | 5.68 |
| Threonine | Thr | T | 119.12 | $C_4H_9NO_3$ | $C_4H_7NO_2$ | 101.11 | 2.09 | 9.10 | — | 5.60 |
| Tryptophan | Trp | W | 204.23 | $C_{11}H_{12}N_2O_2$ | $C_{11}H_{10}N_2O$ | 186.22 | 2.83 | 9.39 | — | 5.89 |
| Tyrosine | Tyr | Y | 181.19 | $C_9H_{11}NO_3$ | $C_9H_9NO_2$ | 163.18 | 2.20 | 9.11 | 10.07 | 5.66 |
| Valine | Val | V | 117.15 | $C_5H_{11}NO_2$ | $C_5H_9NO$ | 99.13 | 2.32 | 9.62 | — | 5.96 |

1pKa is the negative of the logarithm of the dissociated constant for the-COOH group 2pKb is the negative of the logarithm of the dissociated constant for the-$NH_3^+$ group 3pKx is the negative of the logarithm of the dissociated constant for any other group in the molecule 4pI is the pH at the isoelectric point References: D. R. Lide, Handbook of Chemistry and Physics, 72nd Edition, CRC Press, Boca Raton, FL, 1991.

CPPs typically used to date harbour many positively charged residues. Reducing the amount of positively charged residues within the amino acid sequence, whilst retaining the ability to cross a biological membrane, will be more clinically relevant.

Accordingly, it is possible to reduce the charge on the peptide sequences illustrated in Table 2.

The preferred BAC is an oligonucleotide (ON), more preferably still an anti-sense oligonucleotide (AON). Different anti-sense oligonucleotide chemistries are illustrated in Table 4, with the use of low charge or neutral charged chemistries, such as, phosphorodiamidate morpholino oligonucleotides (PMOs) being preferred.

TABLE 4

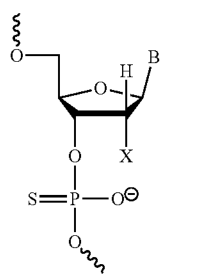

Phosphorothioate (PS)

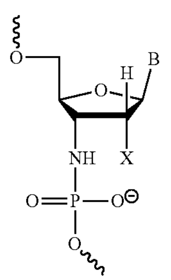

N′3 Phosphoramidite (NP)

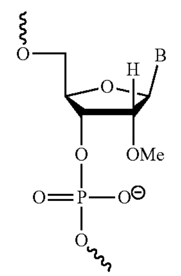

2′-O-Methyl (2′ O-Me)

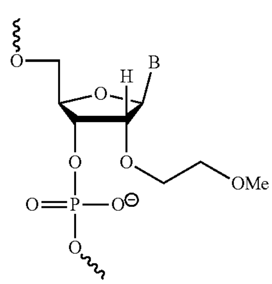

2′-O-Methozyethyl (MOE)

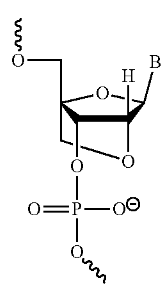

Locked Nucleic Acid (LNA)

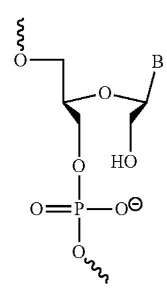

Unlocked Nucleic Acid (UNA)

TABLE 4-continued

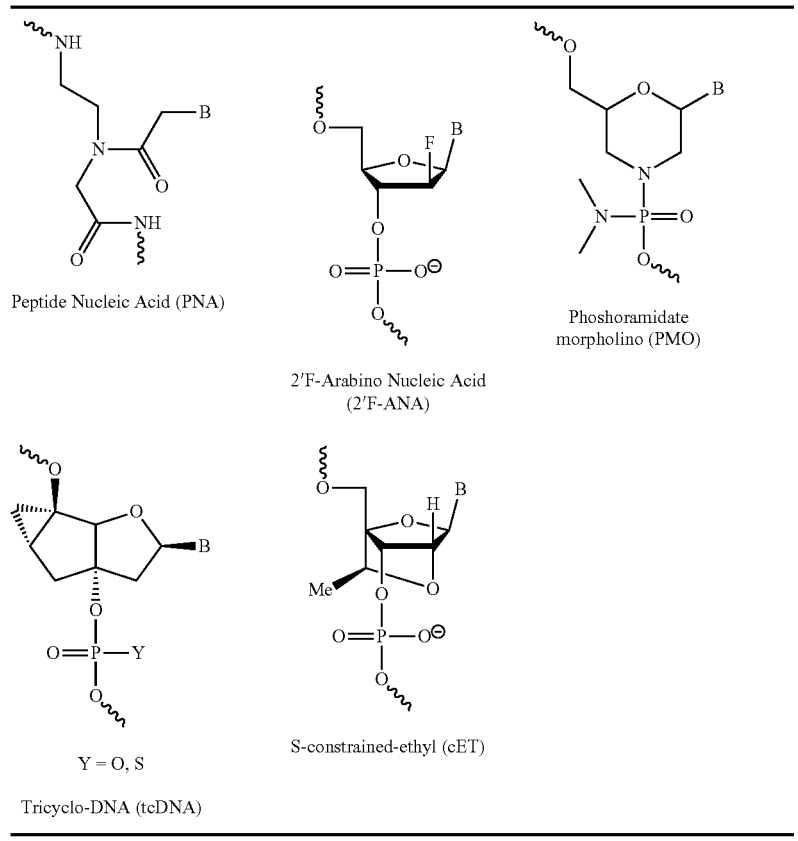

Peptide Nucleic Acid (PNA)

2'F-Arabino Nucleic Acid (2'F-ANA)

Phoshoramidate morpholino (PMO)

Y = O, S

Tricyclo-DNA (tcDNA)

S-constrained-ethyl (cET)

The BAC may target and alter the expression of an endogenous or exogenous gene. Endogenous gene targets include but are not limited to genes associated with neuromuscular disease, metabolic disease, cancer, age-related degenerative diseases, and exogenous gene targets include those of an acquired disease e.g. viral infections.

Whilst the BAC may be linked to the CPP directly the Applicant has found the use of a BFL desirable. Exemplary, non-limiting BFL chemistries are illustrated in Table 5.

TABLE 5

| Entry | Linker (L) | Linker acryonym is present | Z | $Y_3$ |
|---|---|---|---|---|
| 1 | | SMCC | | or not present |
| 2 | | AMAS | | or not present |

TABLE 5-continued

| Entry | Linker (L) | Linker acryonym is present | Z | Y₃ |
|---|---|---|---|---|
| 3 | | BMPS | L–S–CH(NH₂)–C(O)–Y | Z–NH–CH₂CH₂–(O–)ₙ–C(O)– or not present |
| 4 | | GMPS | L–S–CH(NH₂)–C(O)–Y | Z–NH–CH₂CH₂–(O–)ₙ–C(O)– or not present |
| 5 | | DMVS | L–S–CH(NH₂)–C(O)–Y | Z–NH–CH₂CH₂–(O–)ₙ–C(O)– or not present |
| 6 | | EMCS | L–S–CH(NH₂)–C(O)–Y | Z–NH–CH₂CH₂–(O–)ₙ–C(O)– or not present |
| 7 | | LC-SMCC | L–S–CH(NH₂)–C(O)–Y | Z–NH–CH₂CH₂–(O–)ₙ–C(O)– or not present |
| 8 | | SM(PEG)ₙ | L–S–CH(NH₂)–C(O)–Y | Z–NH–CH₂CH₂–(O–)ₙ–C(O)– or not present |
| 9 | | DSG | Not present | Z–NH–CH₂CH₂–(O–)ₙ–C(O)– or not present |
| 10 | | DSCDS | Not present | Z–NH–CH₂CH₂–(O–)ₙ–C(O)– or not present |

TABLE 5-continued

| Entry | Linker (L) | Linker acryonym is present | Z | Y3 |
|---|---|---|---|---|
| 11 |  | HNA | Not present |  or not present |

By way of a footnote to Table 5, the following should be noted:

FIG. 5A highlights general structure of a DCCPM where the following are preferred, but not limited to the following defined atoms or groups.

In a preferred embodiment illustrated in FIG. 5C, where Y1=Nitrogen, Y2=Hydrogen, Y3=spacer such as (PEG)n n=5, but not limited to those identified in Table 5, Z=a sulfur containing moiety e.g. Cysteine and L=BFL such as SMCC Other embodiments may utilize variations over the structure shown in FIG. 5A. For example if another embodiment does not require a thiol for conjugation of the BFL to the CPA as illustrated in FIG. 5D, then Z=Y3 where Y3 is a spacer in Table 5. For a BFL that does not require a sulphur for conjugation of the BAC and CPA e.g. not limited to entries 9-11 in Table 5 Z=a covalent bond between L and Y3

Other embodiments may not require the use of a spacer, a BFL and as such a thiol group for the formation of a DCCPM depicted in FIG. 7 then the following apply. If no spacer is utilized then Y3 can represent a covalent bond between Y1 and the BAC in which case Z and L=Y1 where Y1 is a N terminus of the CPA.

These chemistries may be further expanded and Table 6 exemplifies modifications to amino acids via which functional groups can be introduced to provide desirable properties to the DCCPM. These will include, but are not limited to, an acetyl, a cholesterol, a fatty acid, a polyethylene glycol, a polysaccharide, an aminoglycan, a glycolipid, a polyphenol, a nuclear localising signal, a nuclear export signal, an antibody, and a targeting molecule.

TABLE 6

| Functional group (X) | Reacting Functional Group (X)[1] | Resulting Functional Group |
|---|---|---|
| Aldehyde  | Hydrazine | Hydrazone |
| Thiol | Maleimides | Thioether |
| 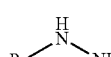 | | |
| Thiol | Thiol | Disulfide |

TABLE 6-continued

| Functional group (X) | Reacting Functional Group (X)[1] | Resulting Functional Group |
|---|---|---|
| 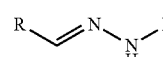 | | |
| Alkyne | Azide | Triazole |
|  | | |
| Amine | Carboxylic acid | Amide |
| Diazirine | Any | Various |
| 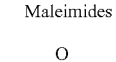 | | |
| Olefin | Olefin | Olefin |
| | | or further reduction |
| 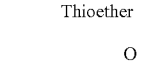 | | |
| Aryl or Olefin R—M | Halide R2—X | R—R2 |

A preferred linker chemistry utilises an amine to sulphydryl cross linker containing N-hydroxysuccinimide esters and malemide reactive groups separated by a cyclohexane spacer namely succinimidyl 4-(N-maleimidomethyl) cyclohexane-1-carboxylate (SMCC) to form a covalent bond between the BFL and the CPP.

A schematic intermediate compound using SMCC as the BFL and the resultant DCCPM is depicted in FIG. 5b.

In a particularly preferred embodiment the linker may incorporate polyethylene glycol in single or multiple units (PEG)$_n$, where n=1 to 10 PEG molecules.

Hereafter, where the CPP comprises the sequence RKF-S5-RLF-S5 (SEQ ID NO: 57) and the BFL is a PEGylated SMCC, the resultant compound is termed CP8M.

Where the CPP comprises the sequence RKF-S5-RLF-S5 (SEQ ID NO: 57) and the BFL is a PEGylated hydrazynal nicotinic acid (HNA), the resultant compound is termed HP8M.

Where the CPP comprises the sequence RKF-S5-RLF-S5 (SEQ ID NO: 57) and the BFL is SMCC, the resultant compound is termed CBM.

Thus a CPA, such as Compound III (FIG. 5b) may be covalently linked to a BFL, if required, preferentially incorporating (PEG)$_n$ where n=1-10.

Covalent linkage to the CPP may be via, for example, but not limited to, a β-ala or any other suitable moiety.

In the preferred embodiment, the (PEG)$_n$ is linked using a sulphur containing molecule e.g. cysteine, to enable covalent coupling as a PEGylated (SMCC). This in turn is covalently linked to a functional group on the BAC, in the preferred embodiment a primary amine, (Compound I), thus generating a DCCPM (Compound V).

According to a second aspect of the invention there is provided a method for facilitating the uptake of a biologically active compound (BAC) into a cell by the conjugation of the biologically active compound, directly or via a bi-functional linker (BFL), to a cell penetrating agent (CPA) which is a stabilized peptide which has a conformation imposed upon it by stapling to form a stapled peptide (StaP) or stitching to form a stitched peptide (StiP), to form a drug carrying cell penetrating molecule (DCCPM) and presenting said DCCPM to said cell in a suitable vehicle.

Where HNA has been incorporated into the terminal end of the CPP, to form a DCCPM in which the BAC is an ON, the ON has been modified to incorporate 4 formyl benzioic acid to facilitate covalent conjugation.

According to a third aspect of the present invention there is provided a DCCPM of the first aspect of the invention for use in the treatment of a disease requiring alteration of the expression of an endogenous or exogenous gene.

The DCCPM may be used in the treatment of a, for example, neuromuscular disease, metabolic disease, cancer, age-related degenerative disease or to treat an acquired viral infection.

In one embodiment the DCCPM is used in the treatment of a muscular dystrophy e.g. Duchenne muscular dystrophy (DMD) although the skilled person will readily appreciate that the invention can be used to target a wide range of genes.

In the case of DMD the DCCPM may comprise an AON targeting exon 51 of the dystrophin gene.

In accordance with a fourth aspect of the present invention there is provided a method of improving the bioavailability of a drug or BAC comprising linking the drug or BAC to a CPP which is a stabilized peptide which has a conformation imposed upon it by stapling to form a stapled peptide (StaP) or stitching to form a stitched peptide (StiP).

In accordance with a fifth aspect of the present invention there is provided a method of introducing a drug or BAC to a site which is refractory to a drug or BAC in its native state comprising linking the drug or BAC to a CPP which is a stabilized peptide which has a conformation imposed upon it by stapling to form a stapled peptide (StaP) or stitching to form a stitched peptide (StiP) and administering it to a subject.

The DCCPMs of the invention can be used to administer the drug or BAC to a target tissue, such as, for example the heart, brain or muscle.

In accordance with a sixth aspect of the present invention there is provided a method of treating a subject to alter the expression of an endogenous or exogenous gene comprising administering a DCCPM of the invention to a subject.

In accordance with a seventh aspect of the present invention there is provided a composition comprising a DCCPM of the invention and one or more pharmaceutically acceptable excipients enabling the composition to be administered orally, parenterally, intravenously or topically.

BRIEF DESCRIPTION OF THE DRAWINGS

Embodiments of the invention are further described hereinafter with reference to the accompanying Drawings, in which:

FIG. 1a is an example of a non-cyclised and an i,i+4 ring closing metathesis (RCM) using Grubb's Gen 1 catalyst to form an StaP CPA;

FIG. 1b is an example of a reduced RCM StaP using conventional reduction chemistry;

FIG. 1c is a schematic showing a selection of different StaP or StiP RCM configurations and their corresponding starting positions;

Figure 1A:
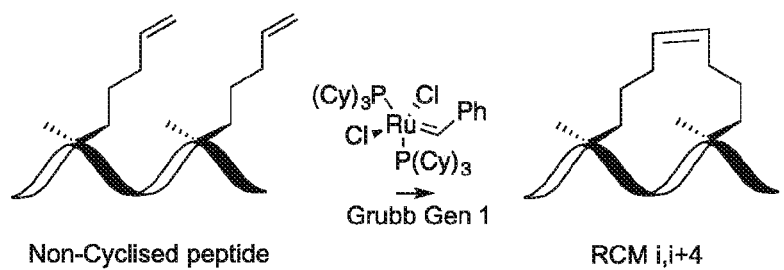
FIG. 1a-c show a general schematic of a CPP which it has been stabilized by means of the incorporation of olefin-bearing α,α-di-substituted amino acids that permit a further chemical modification such that a cross link can be formed. Cross linking of two such non-natural amino acids is termed stapling; cross linking involving more than two non-natural amino acids is termed stitching. This schematic can be referenced against Tables 1 and 2 of this application.
Figure 1B:
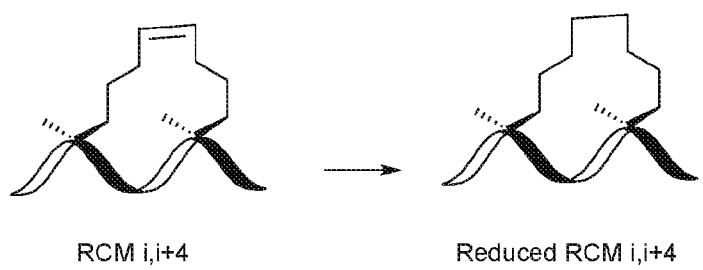
Figure 1C:
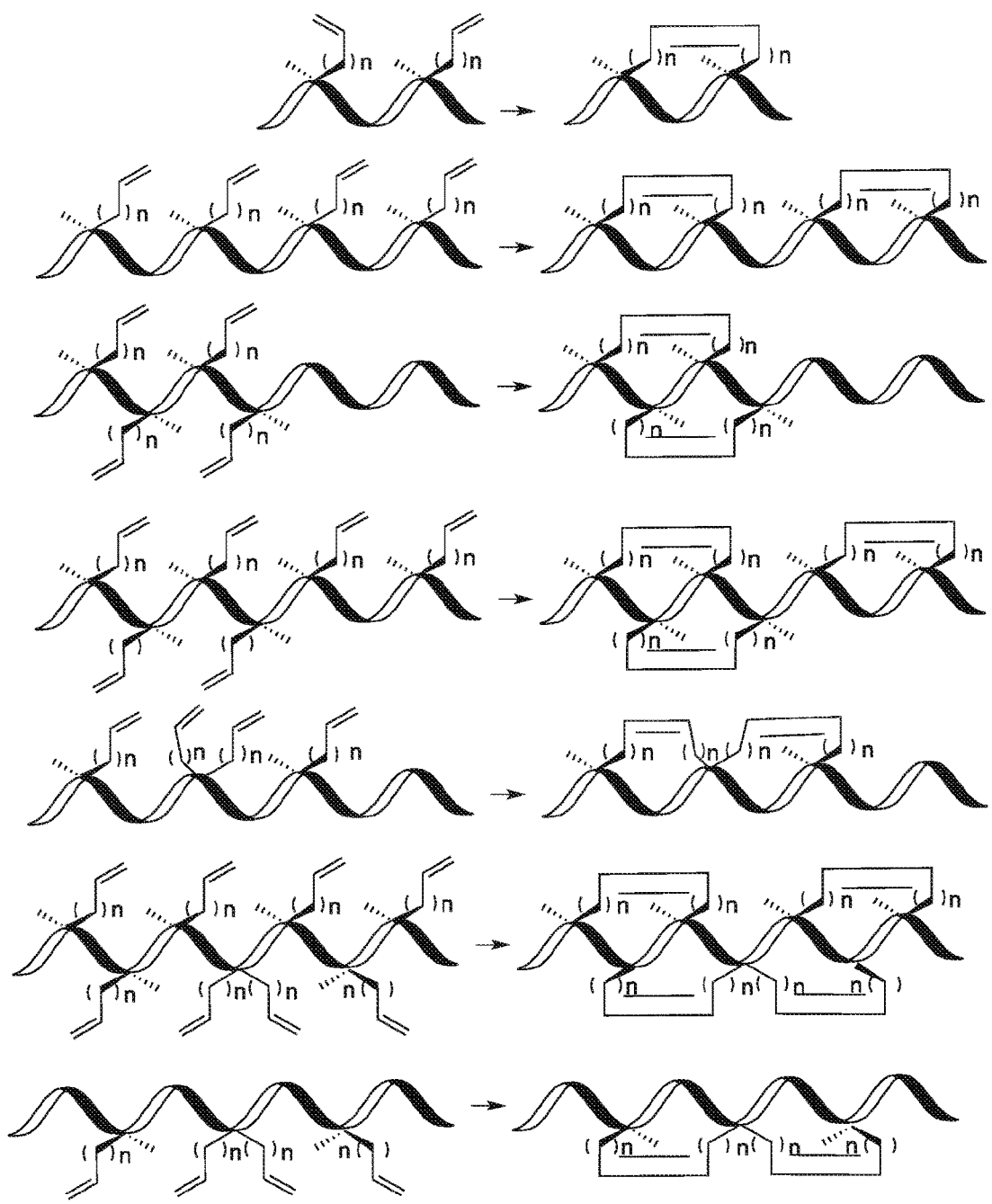
Figure 2:
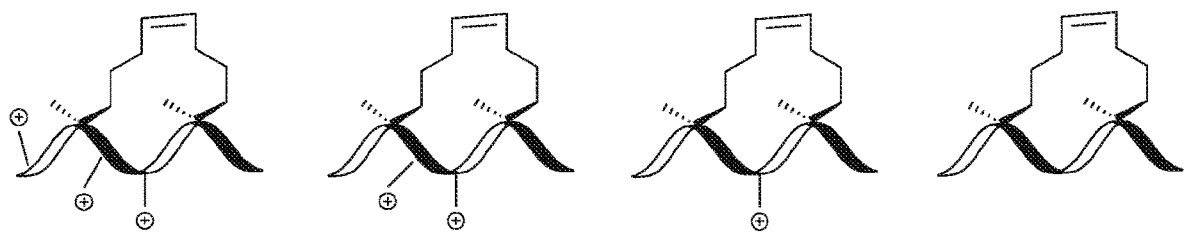
FIG. 2 exemplifies the structures of charge variants: 3+(CP8M-3), 2+(CP8M-2), 1+(CP8M-1) and 0+ (CP8M-0) illustrating relative positions of charge on the StaP, however the positions and charge can be varied in any permutation or combination.
Figure 3:
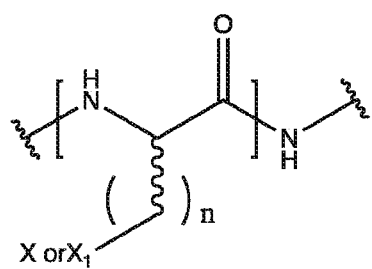
FIG. 3 exemplifies the structure of an amino acid which can be incorporated into StaP or StiPs with varying functional groups as defined in Table 6. The functional groups can then be used for bio-conjugation.
Figure 4A:
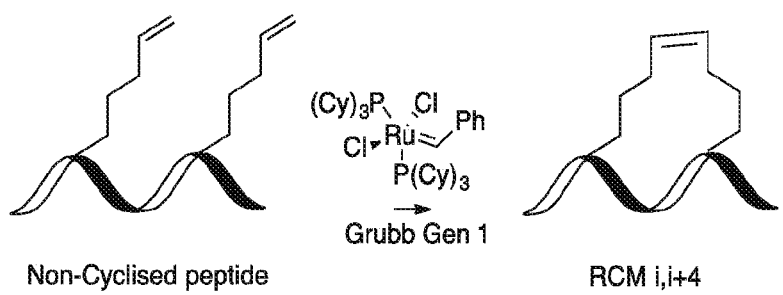
FIG. 4a is a representation of a RCM reaction to form a StaP.
Figure 4B:
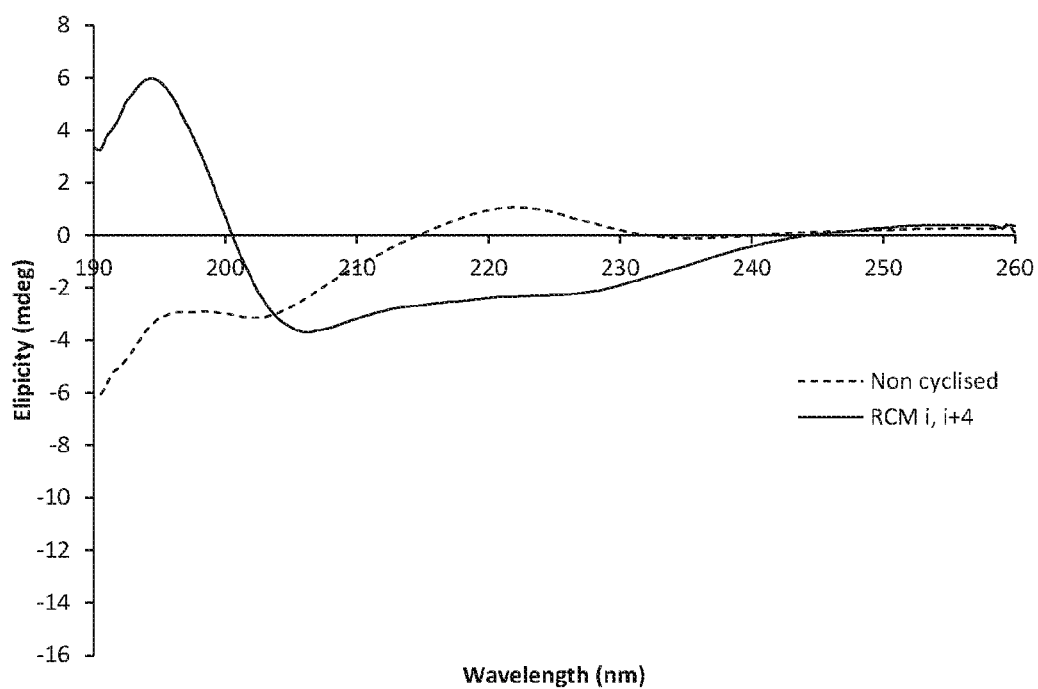
FIG. 4b shows the resulting CD spectrum of the StaP and non-cyclised stating peptide.
Figure 4C:
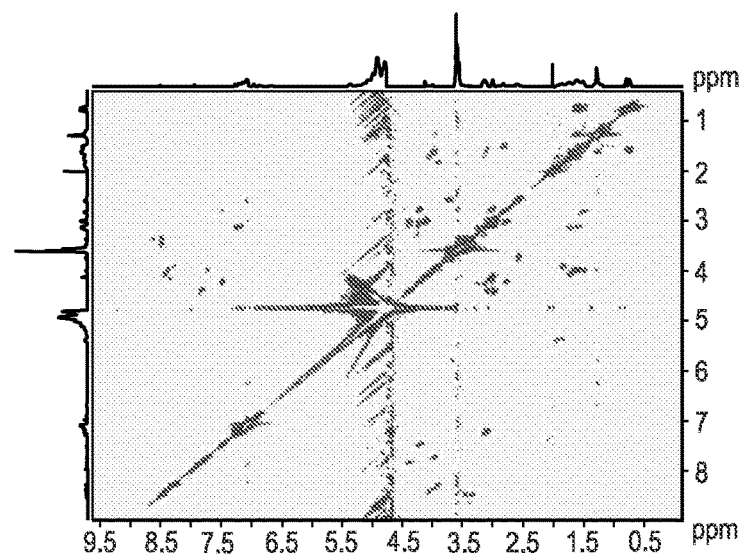
FIG. 4c is a COSY NMR spectra of CP8M.
Figure 4D:
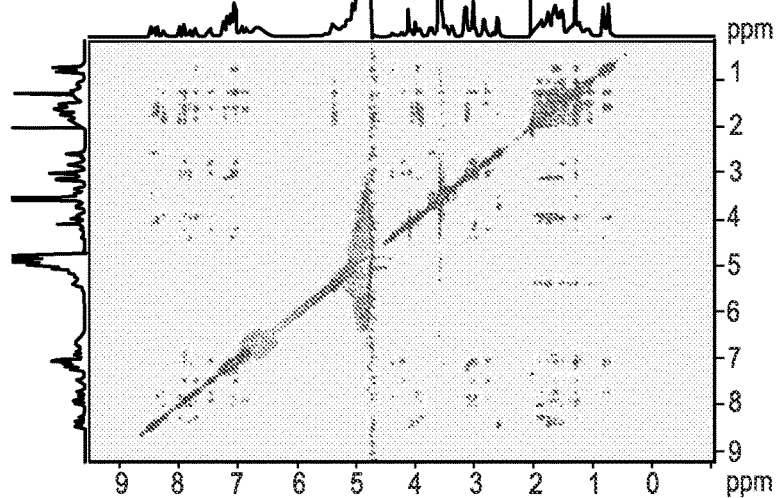
FIG. 4d is a NOESY NMR Spectra of CP8M.
Figure 4E:
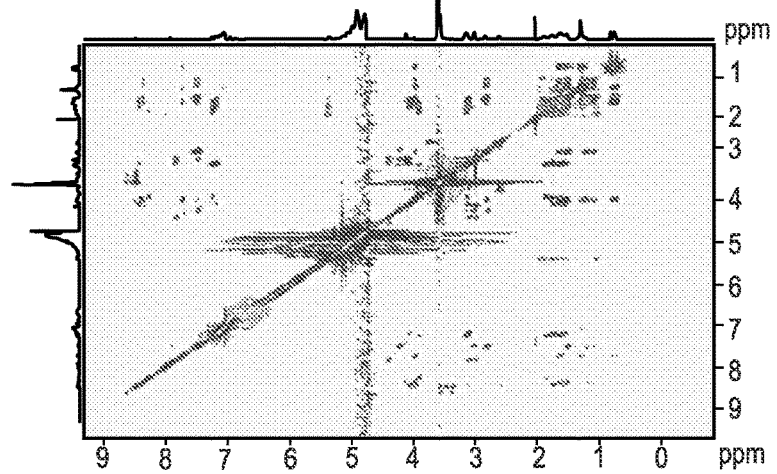
FIG. 4e is a TOCSY NMR spectra of CP8M.
Figure 5A:
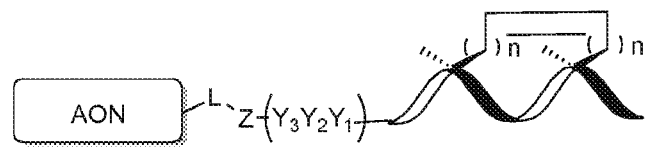
Figure 5B:
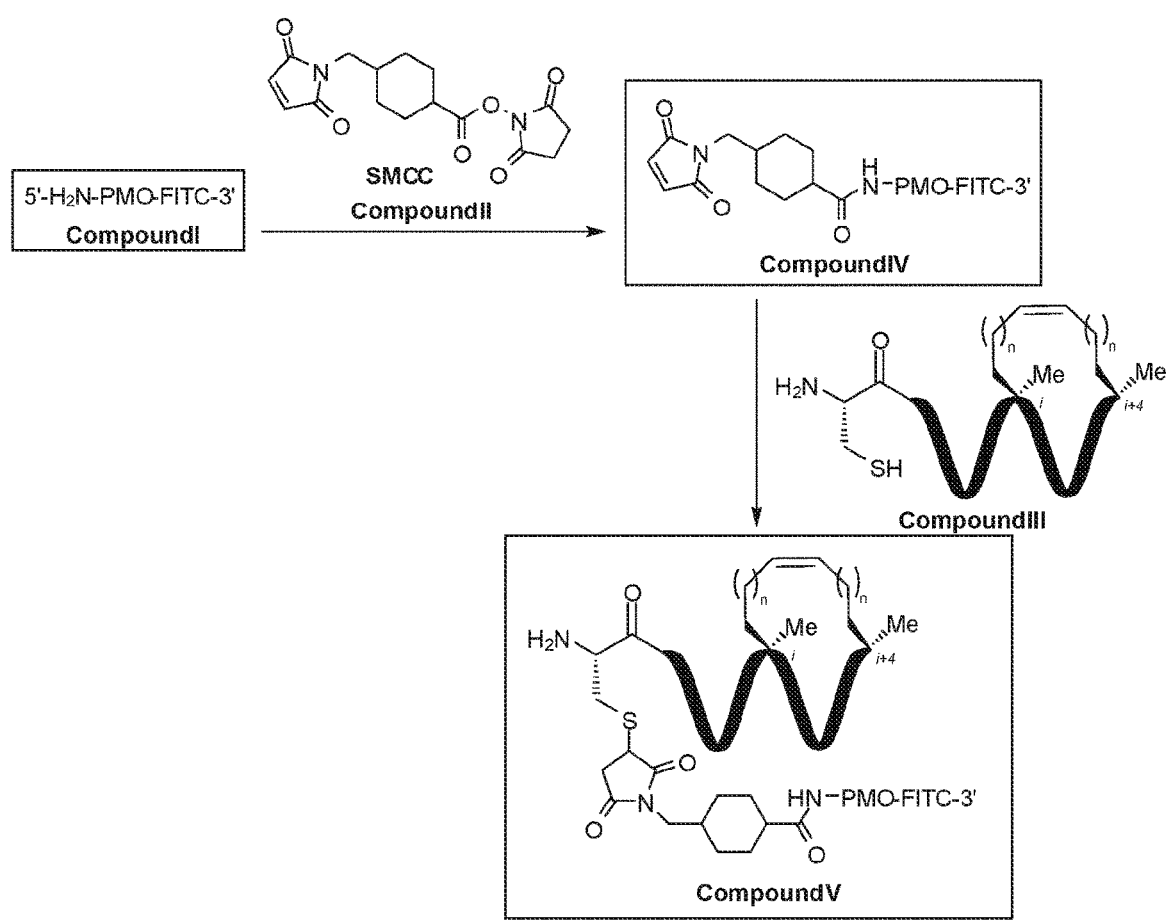
Figure 5C:
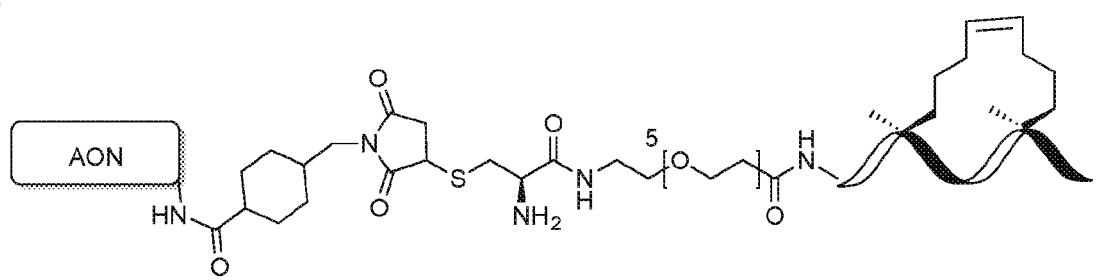
Figure 5D:
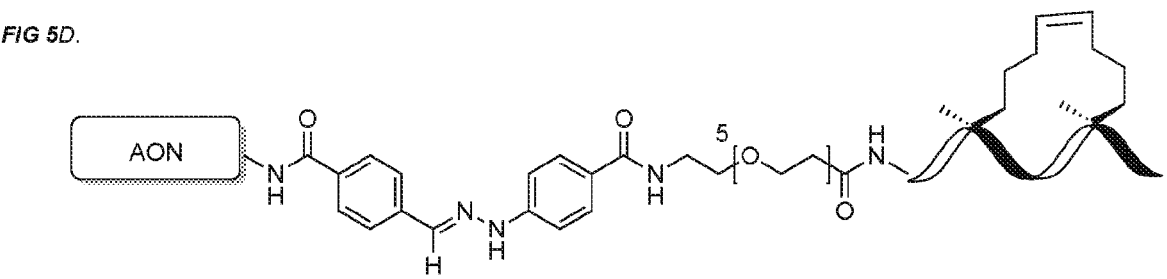
Figure 6:
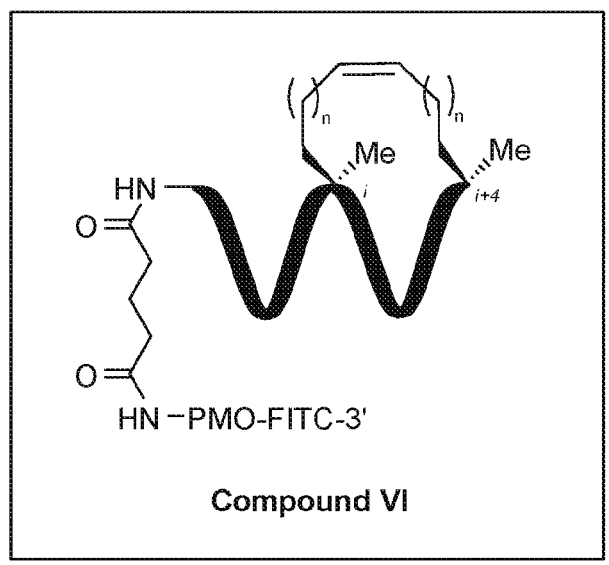
Figure 7:
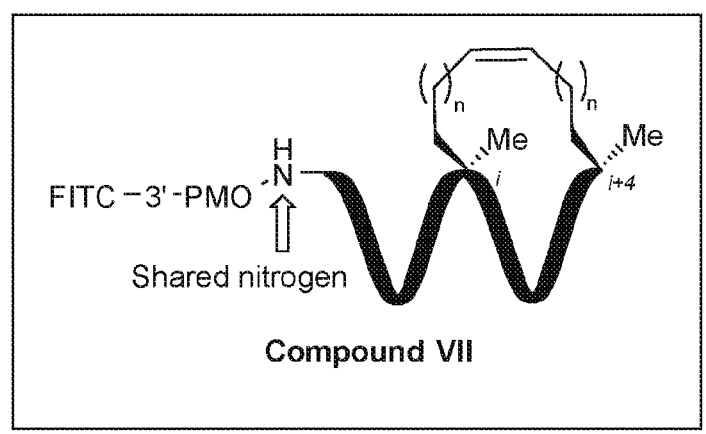
Figure 8A:
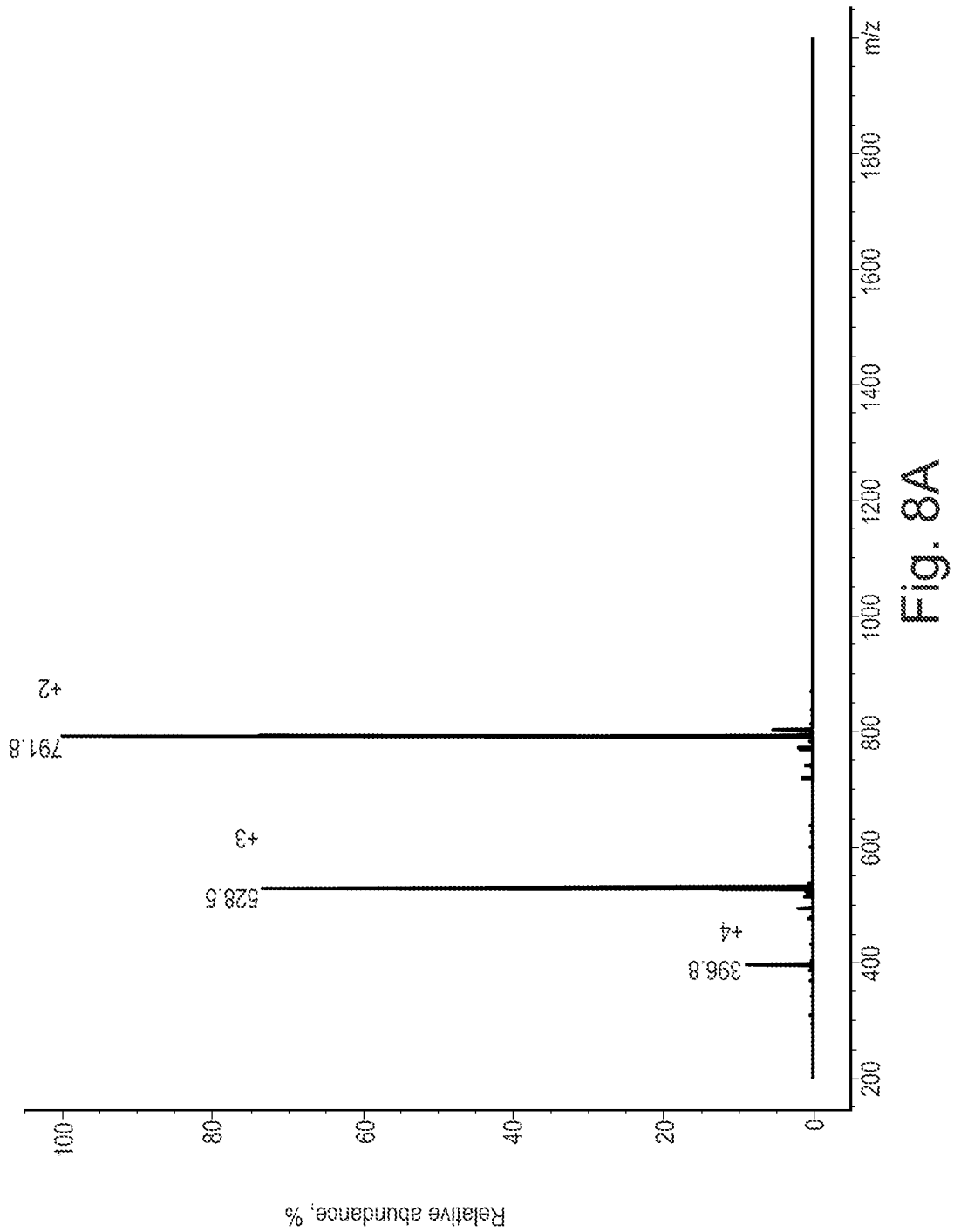
Figure 8B:
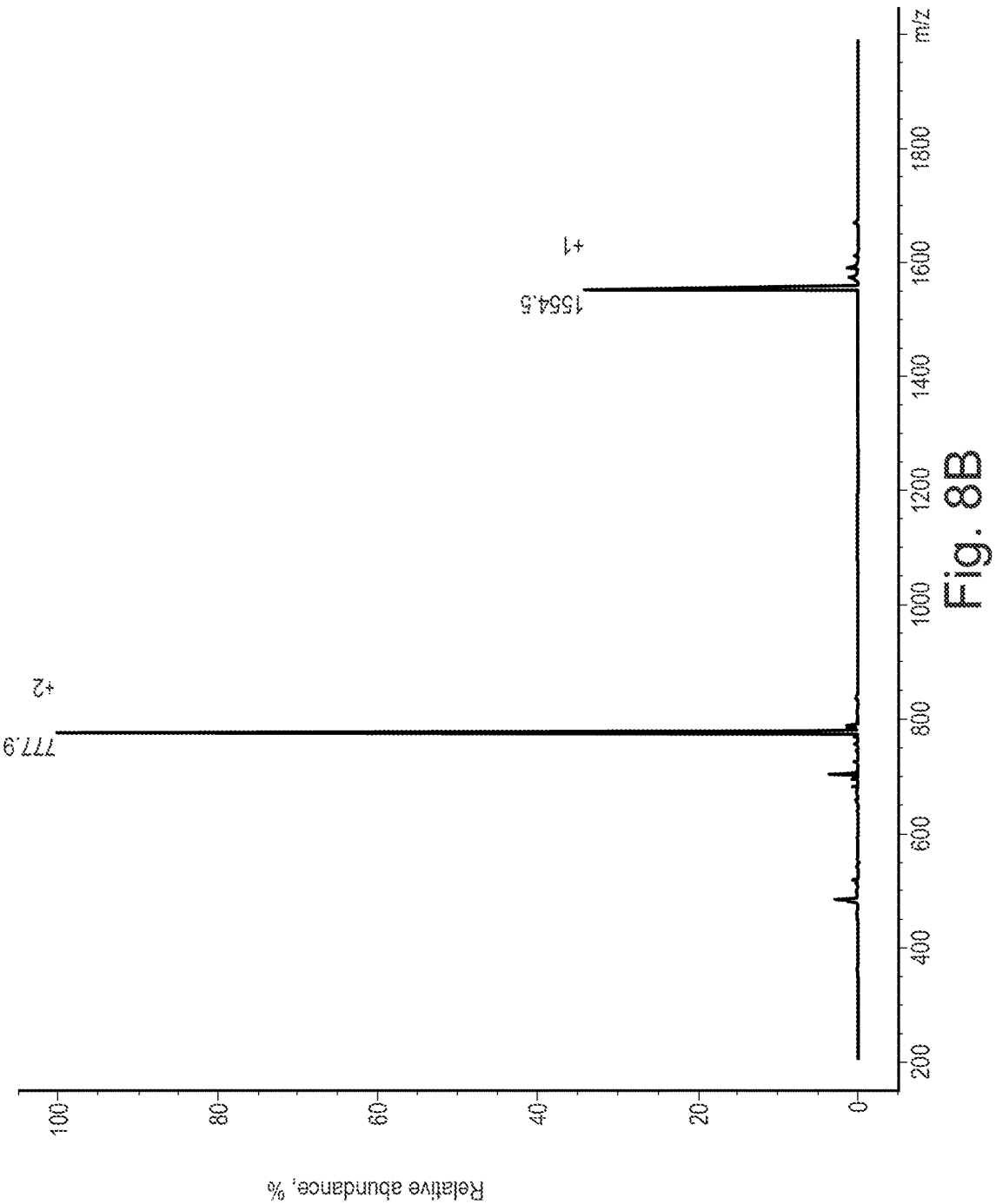
Figure 8C:
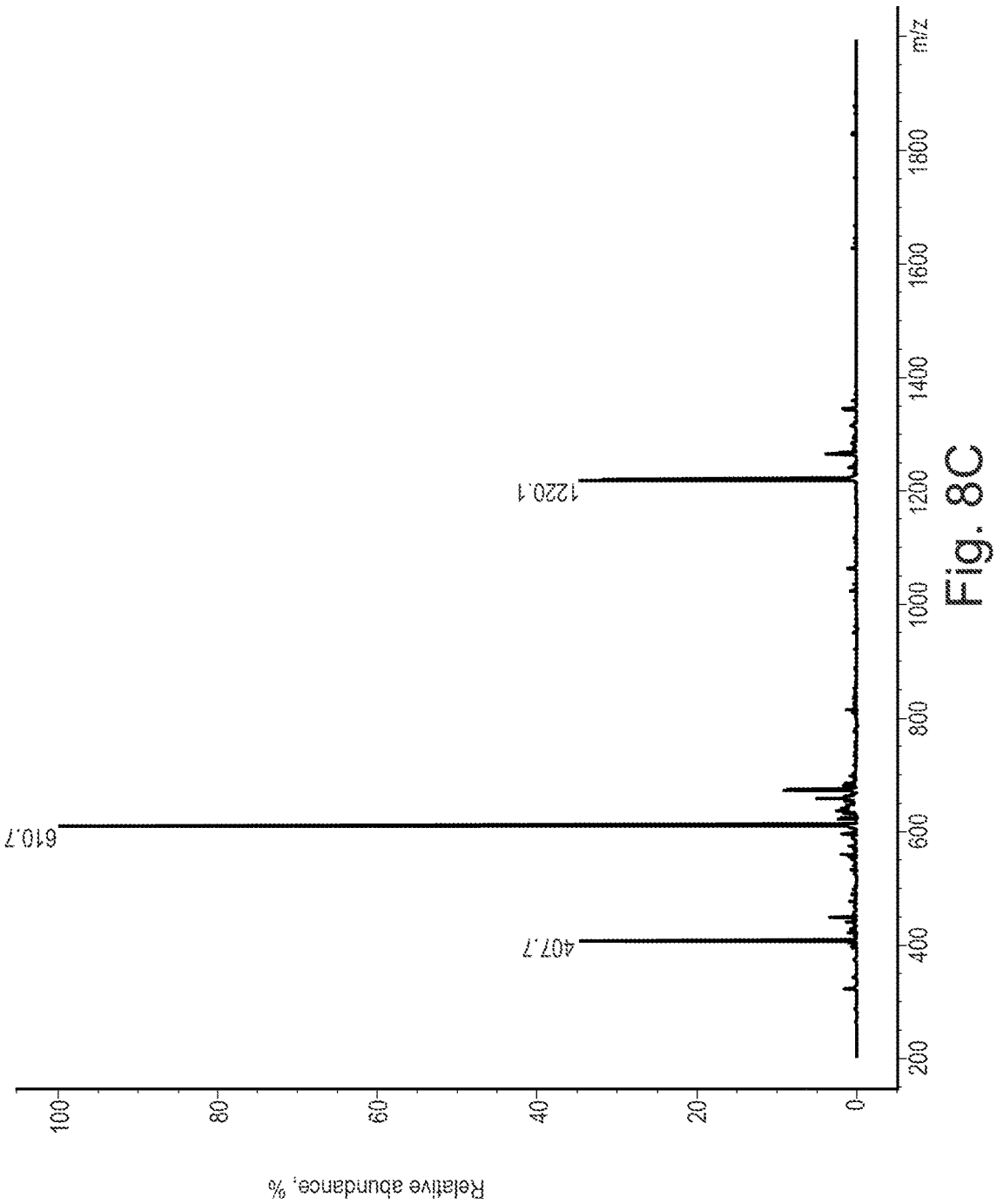
Figure 8D:
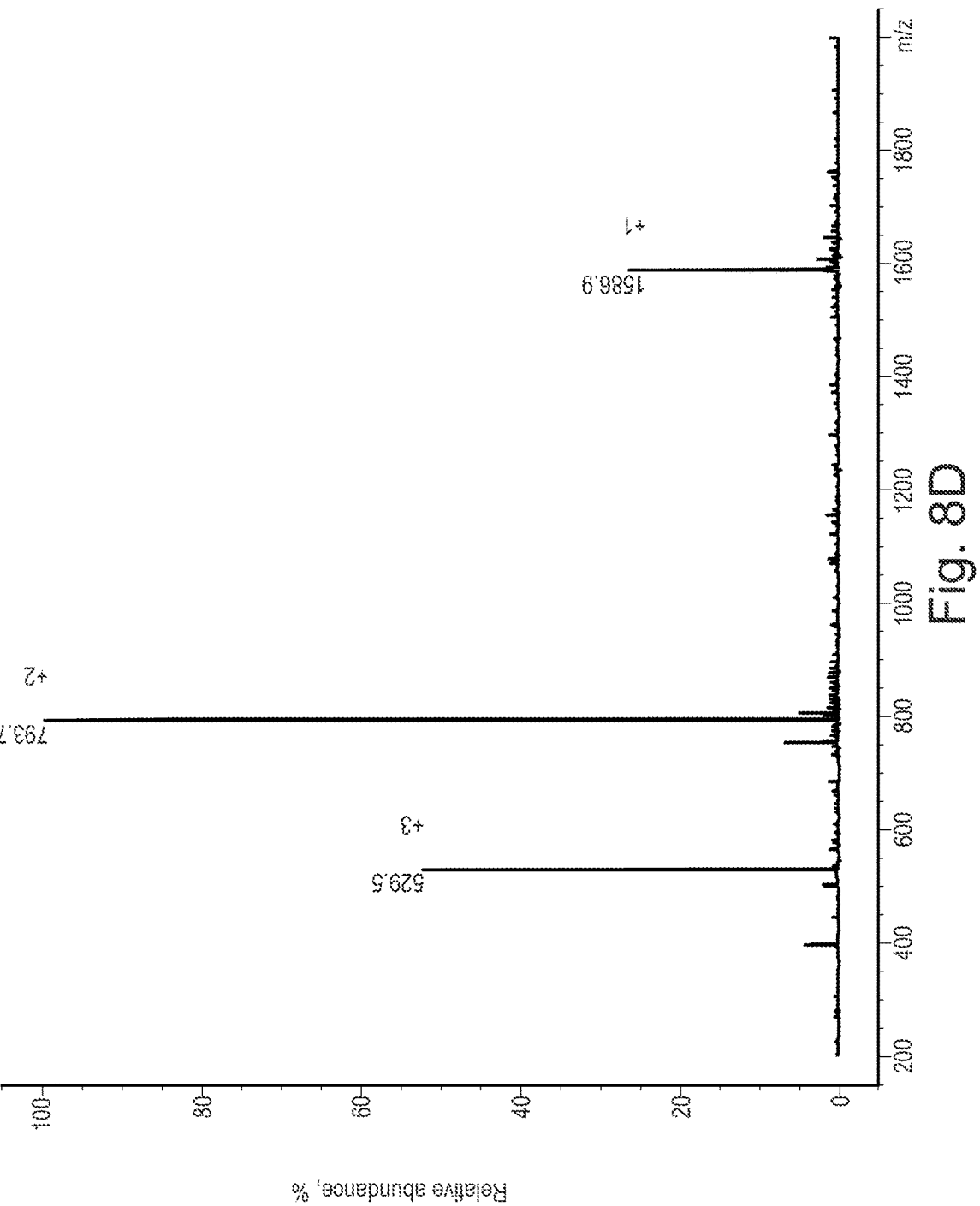
Figure 8E:
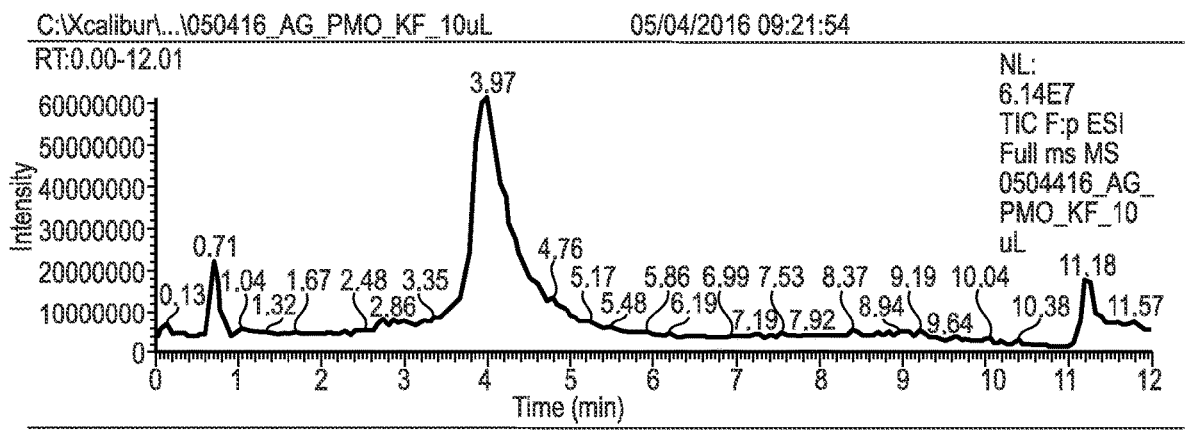
Figure 8E:
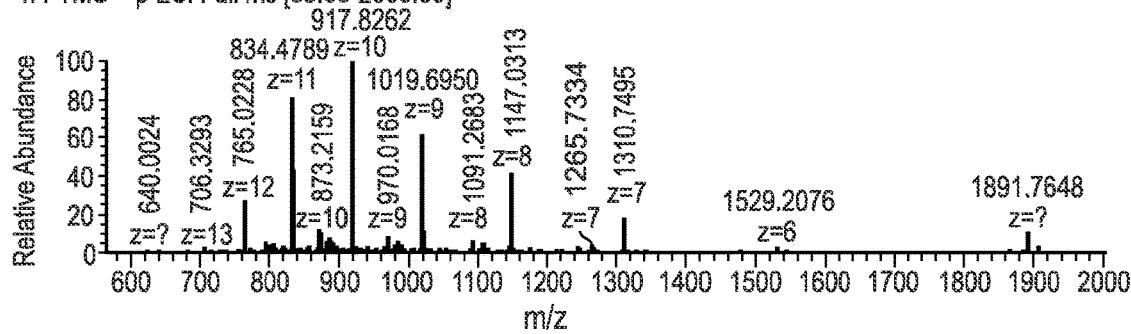
Figure 8E:
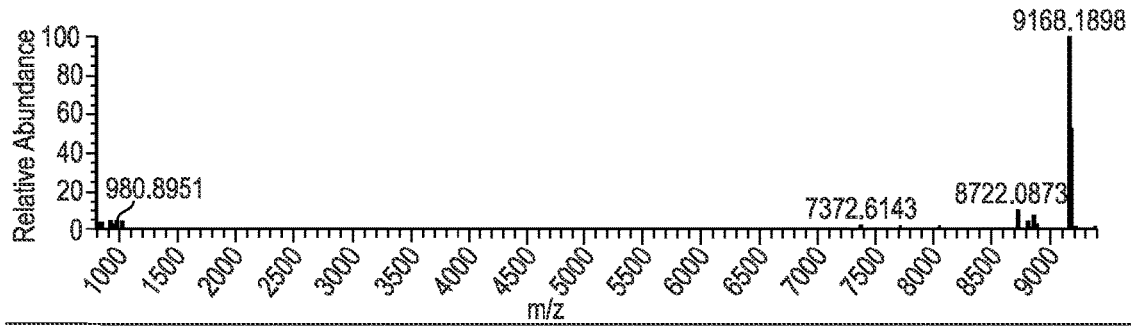
Figure 8E:
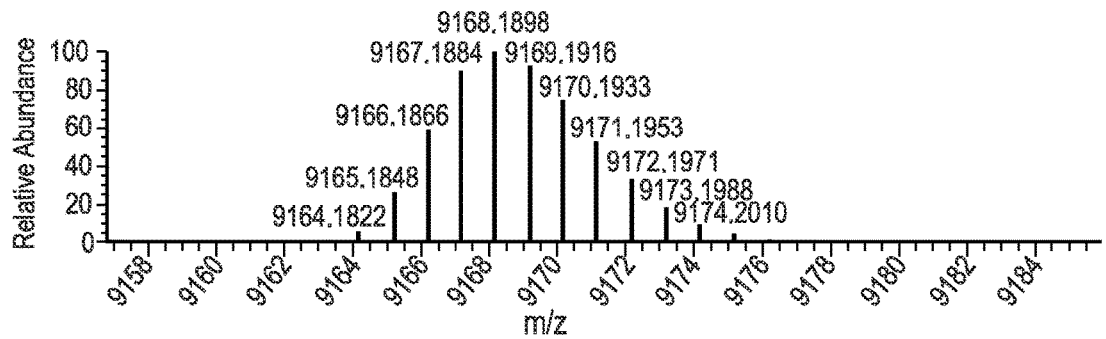
Figure 8F:
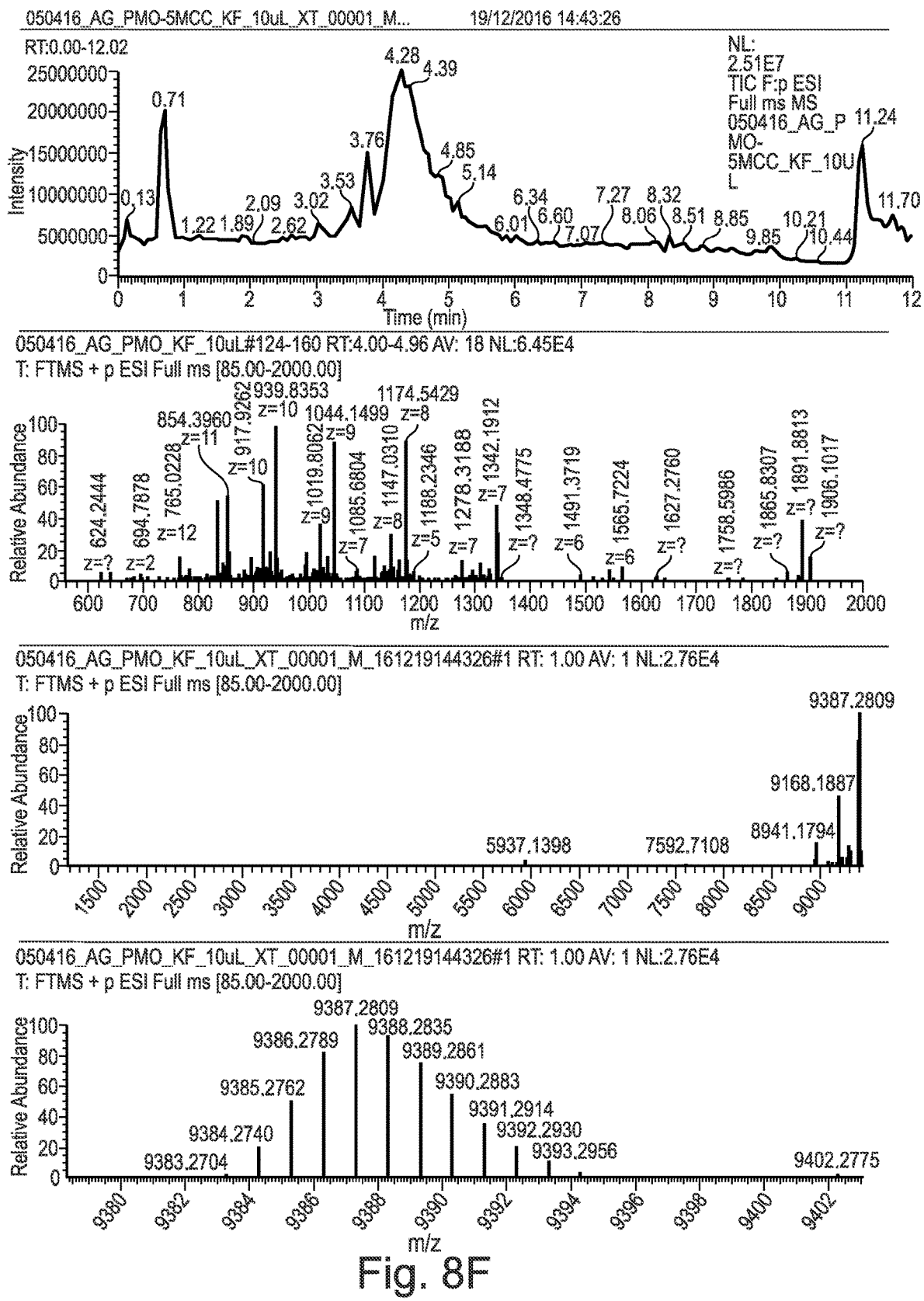
Figure 8G:
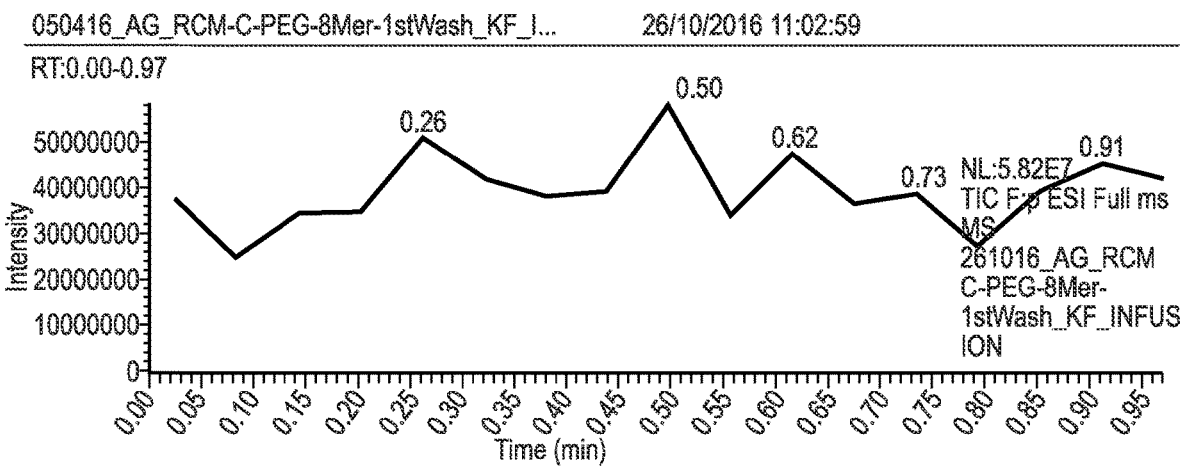
Figure 8G:
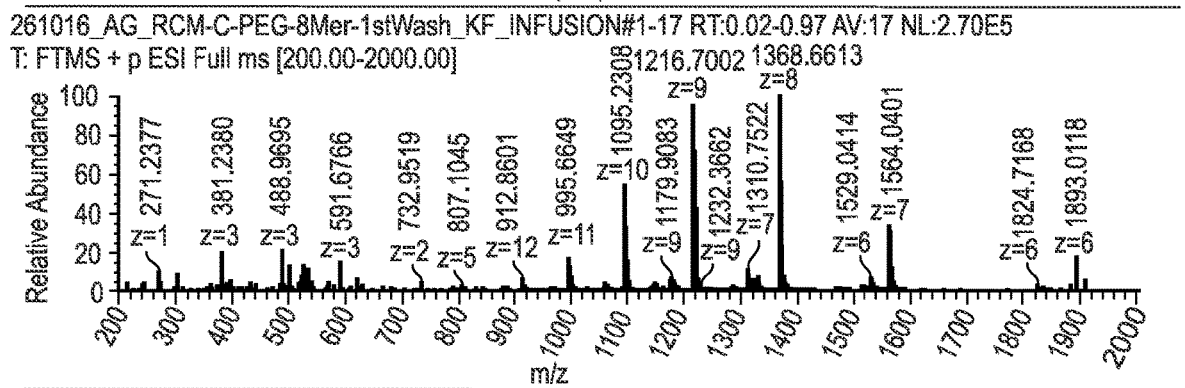
Figure 8G:
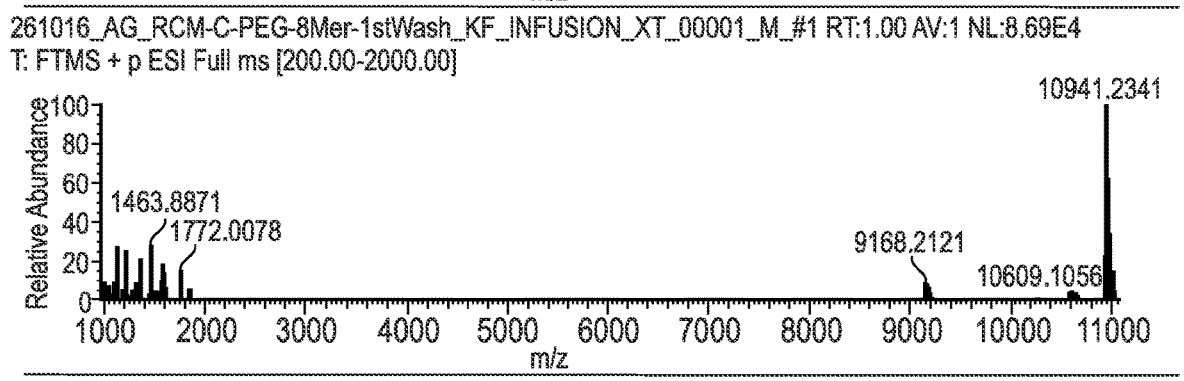
Figure 8G:
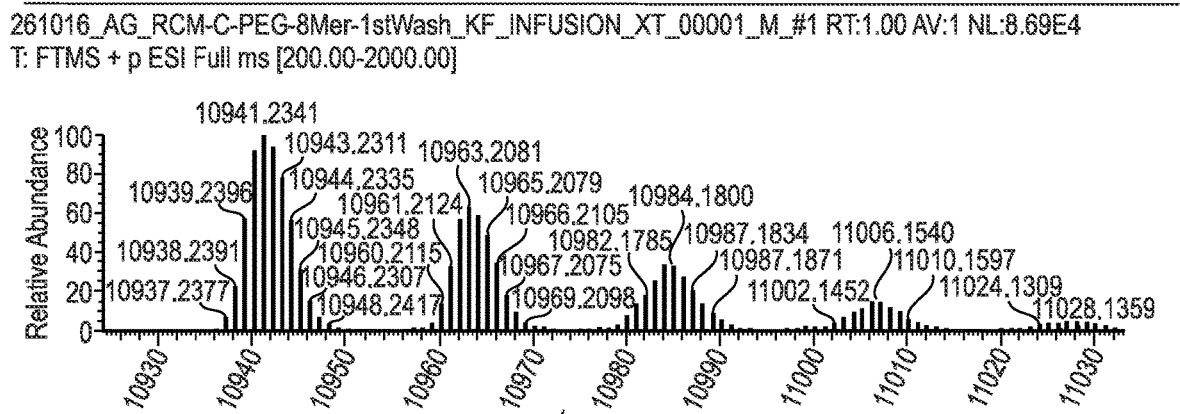
Figure 8H:
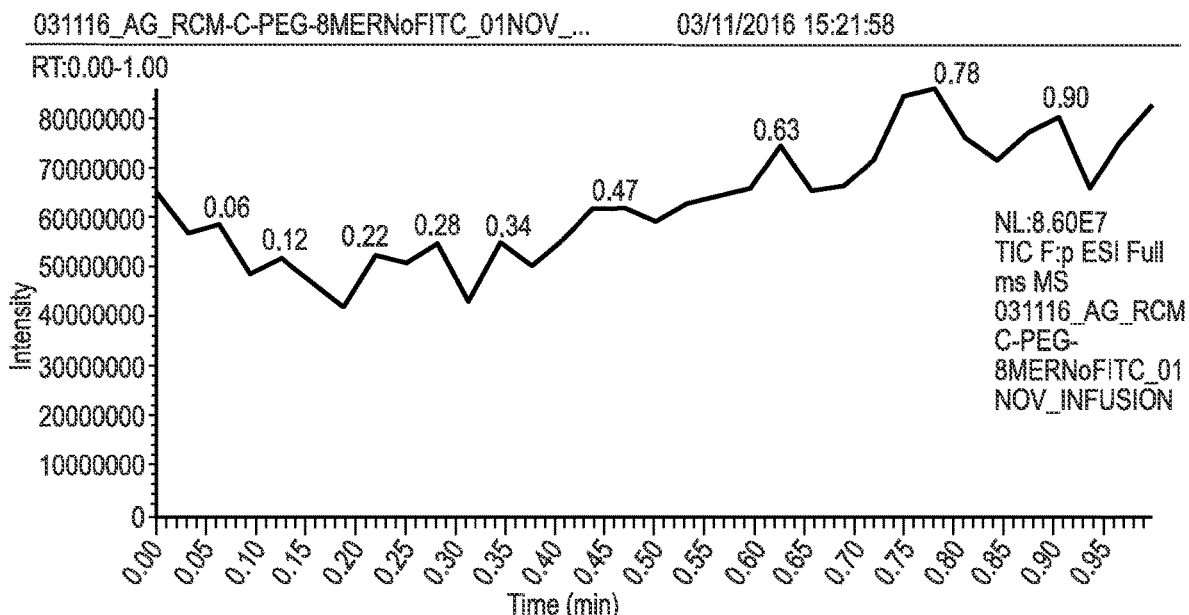
Figure 8H:
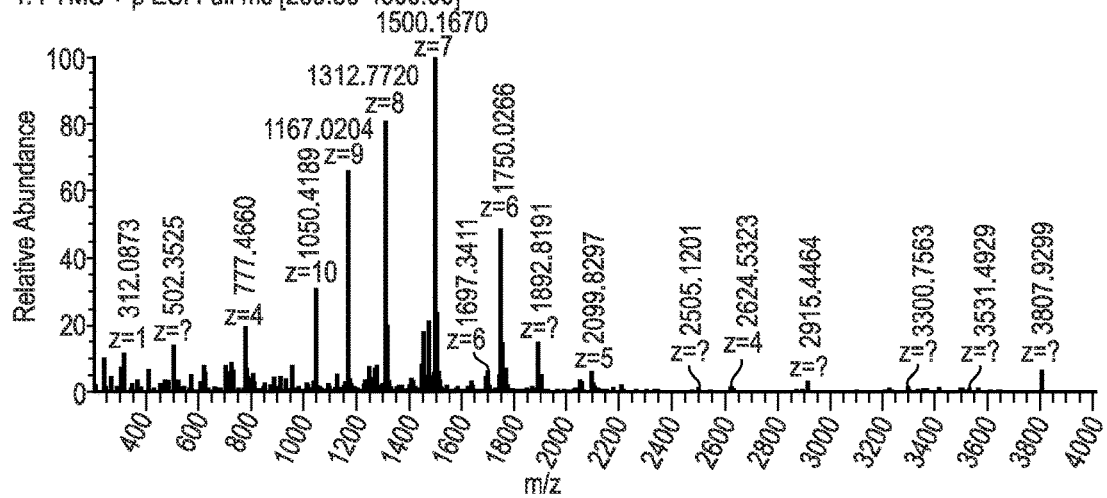
Figure 8H:
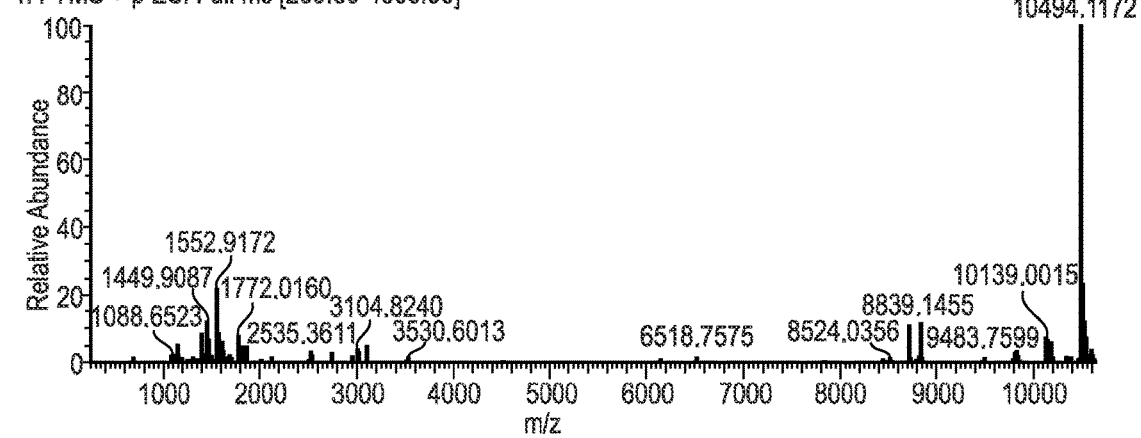
Figure 8I:
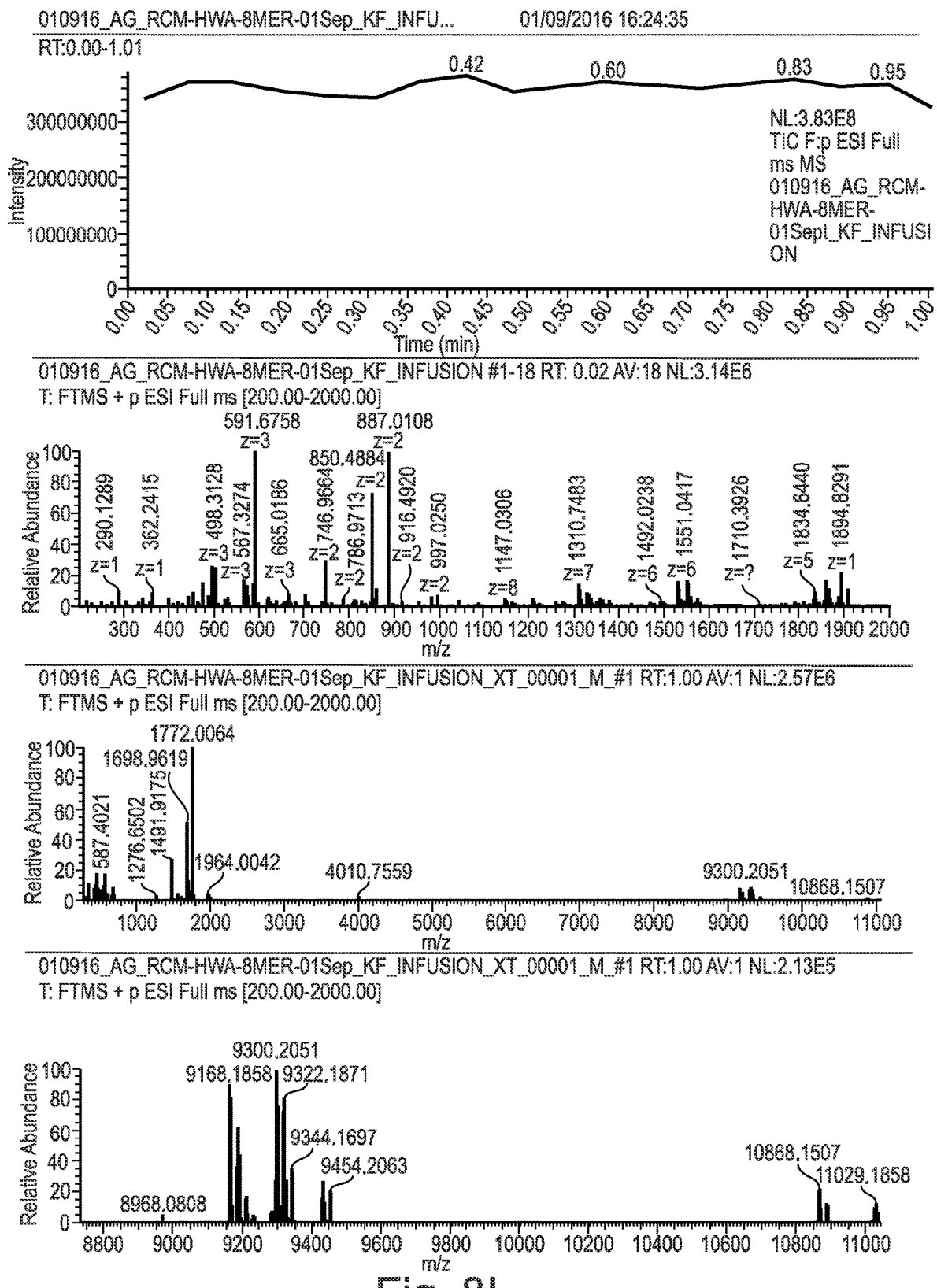
Figure 8J:
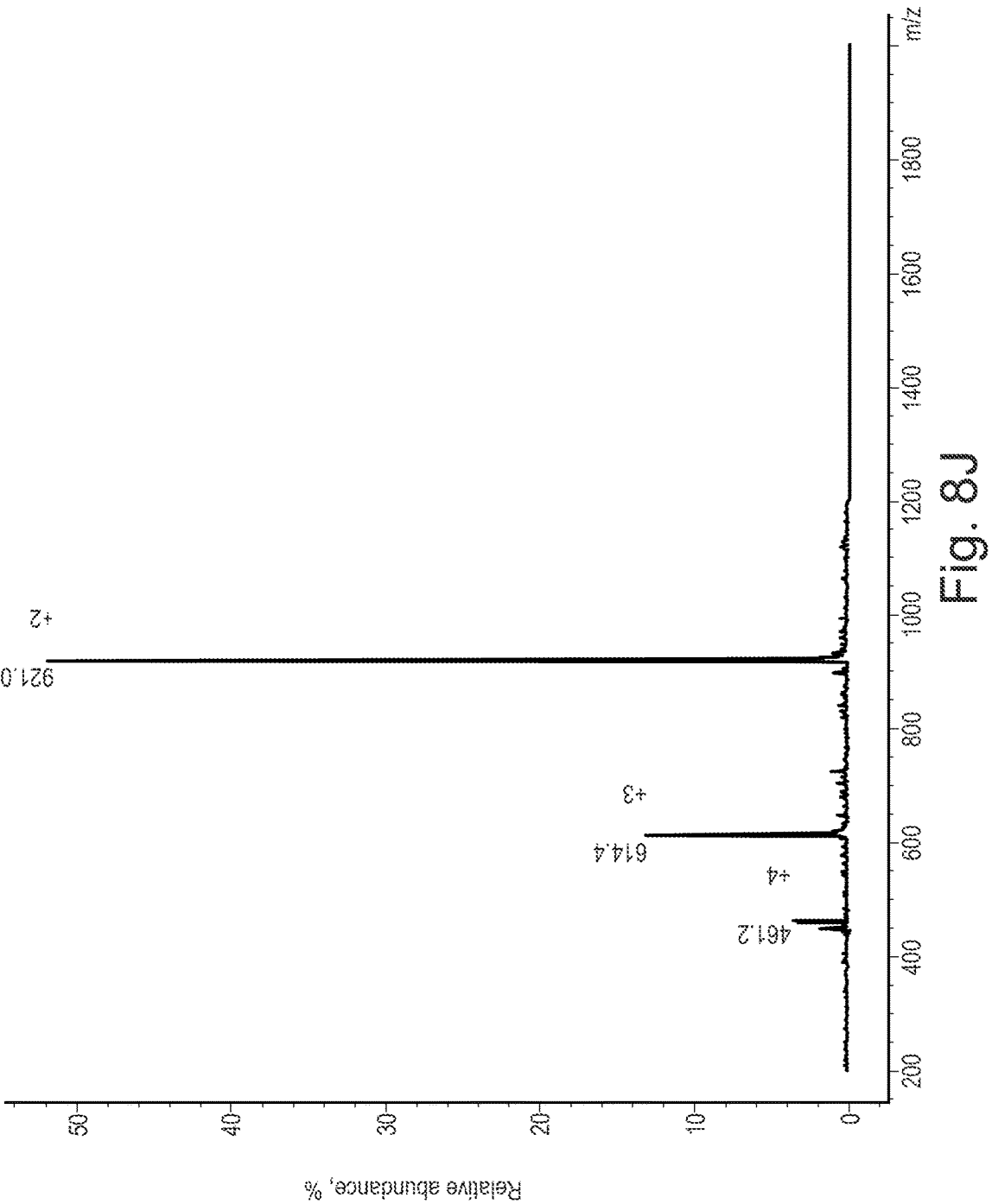
Figure 8K:
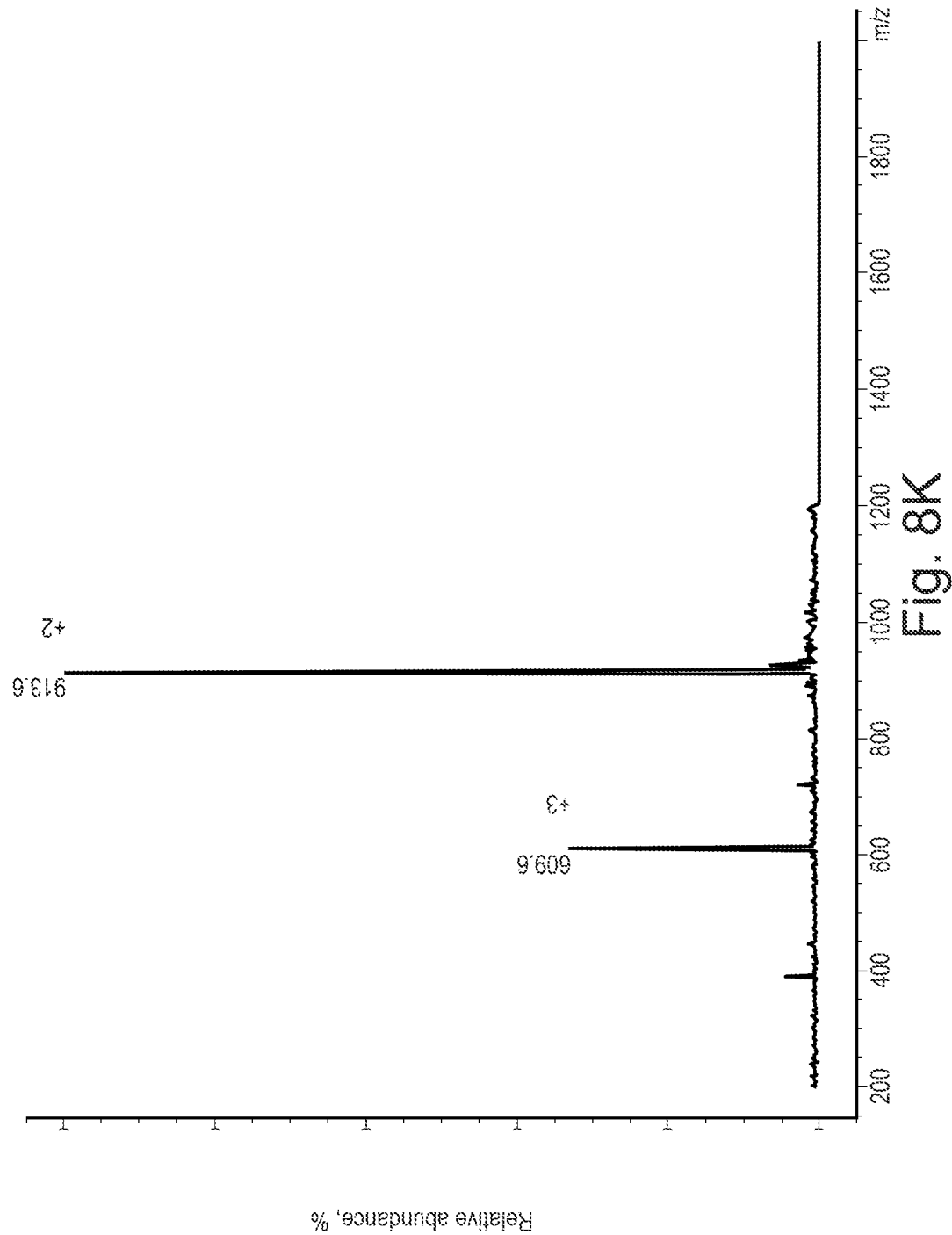
Figure 8L:
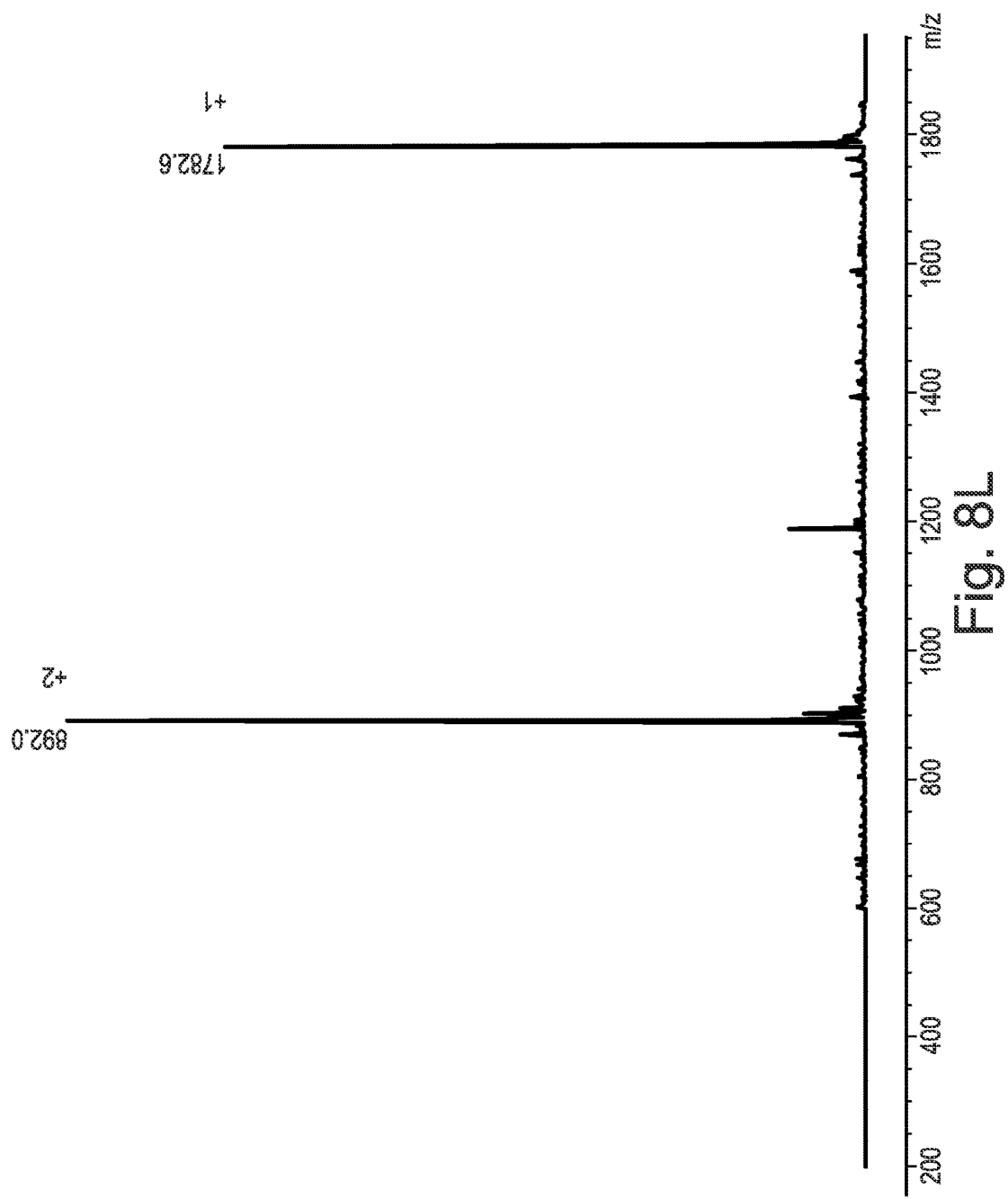
Figure 8M:
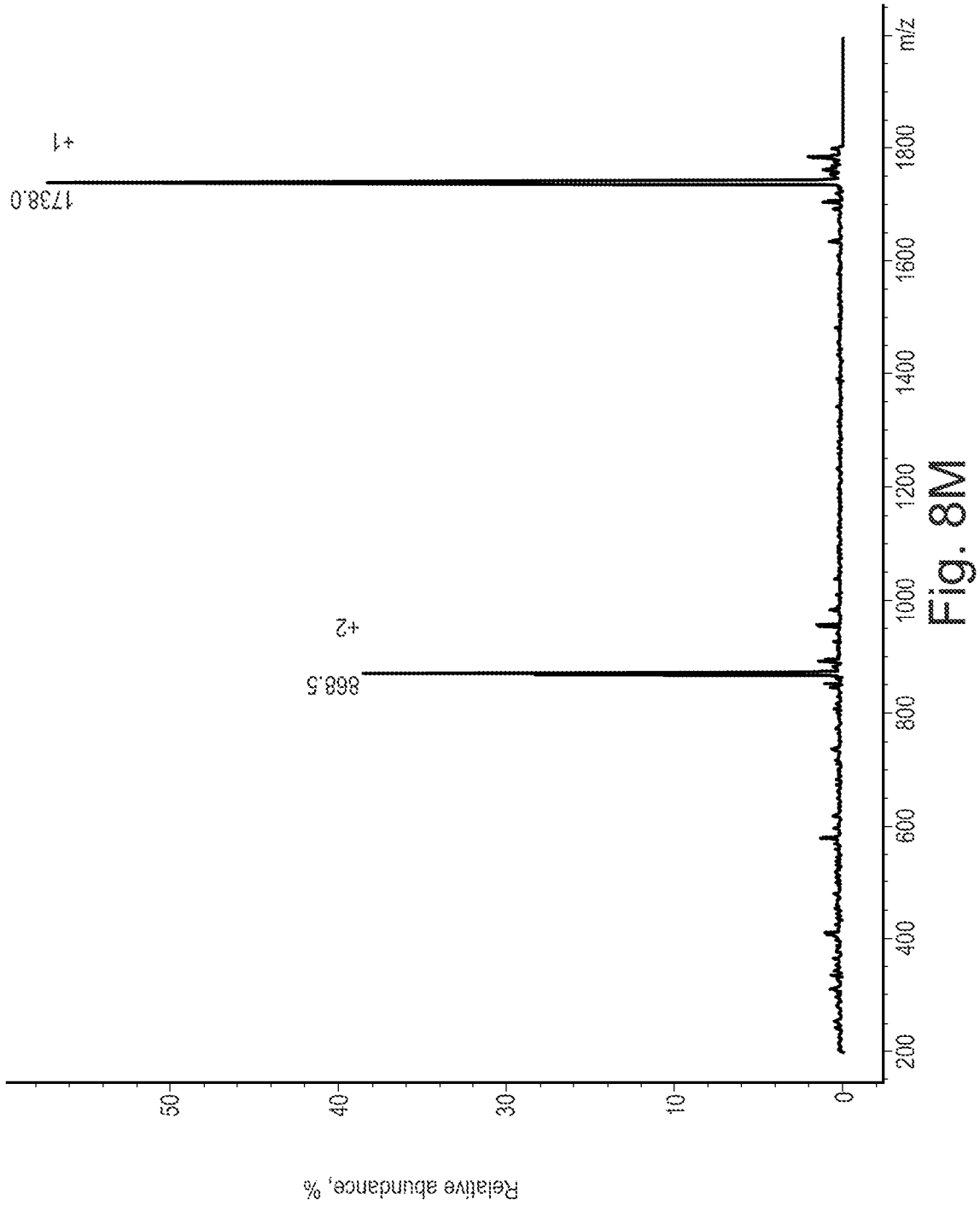
Figure 8N:
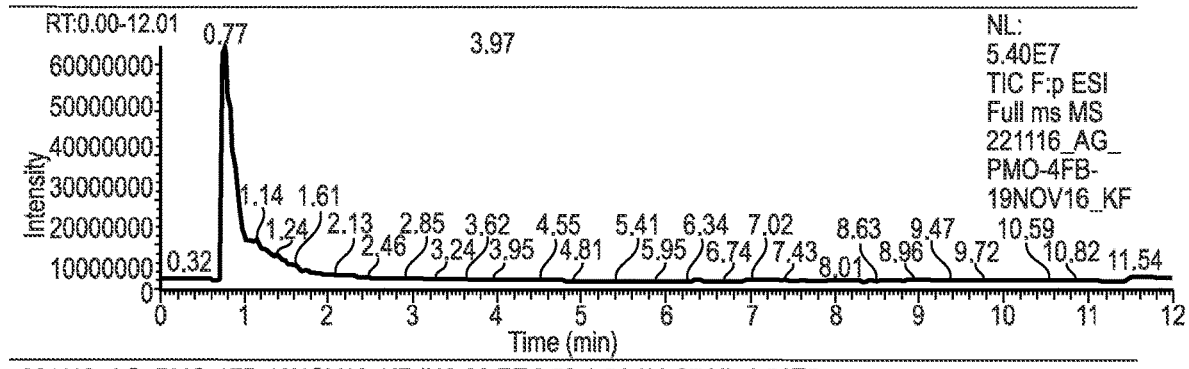
Figure 8N:
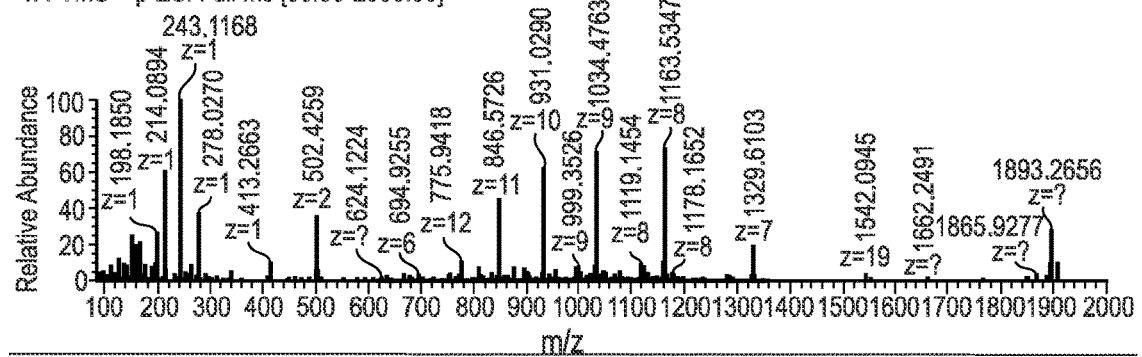
Figure 8N:
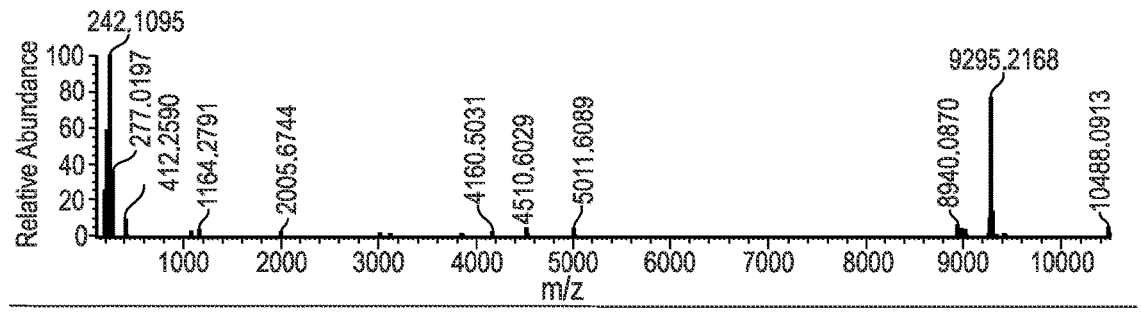
Figure 8N:
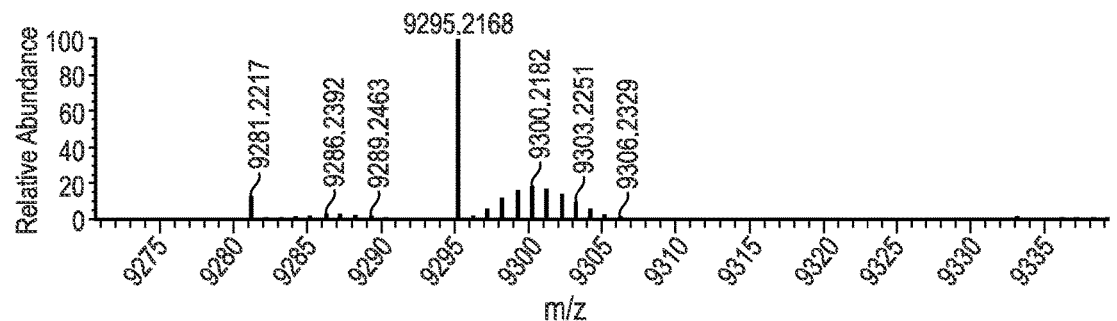
Figure 8O:
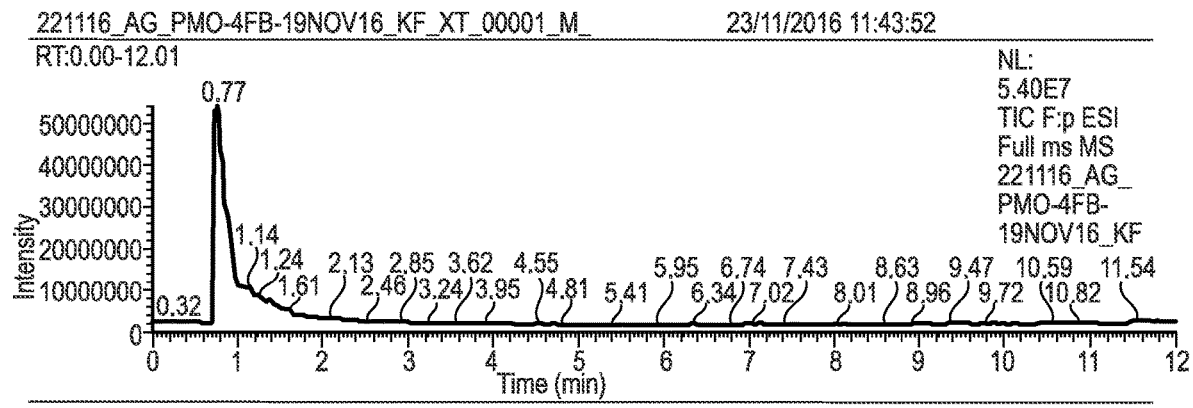
Figure 8O:
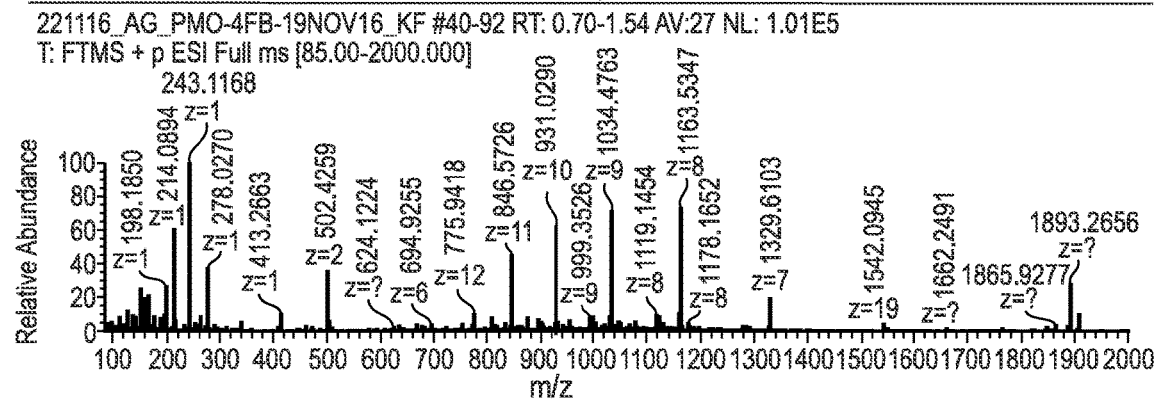
Figure 8O:
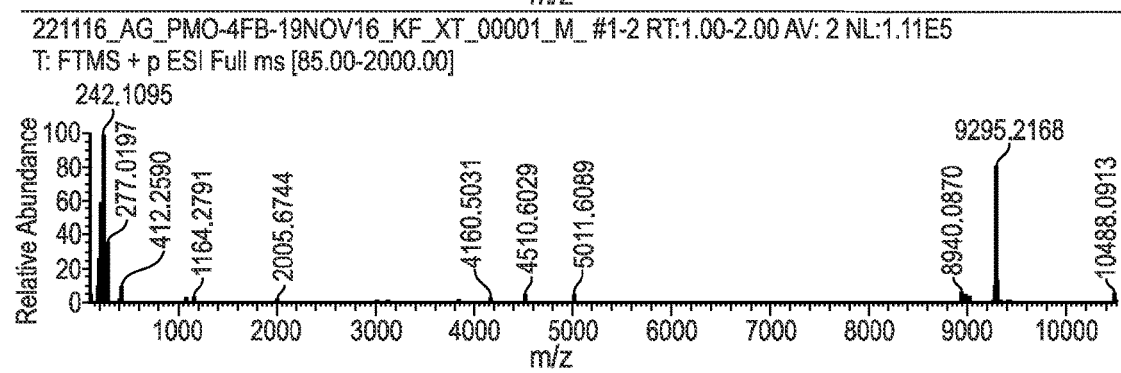
Figure 8O:
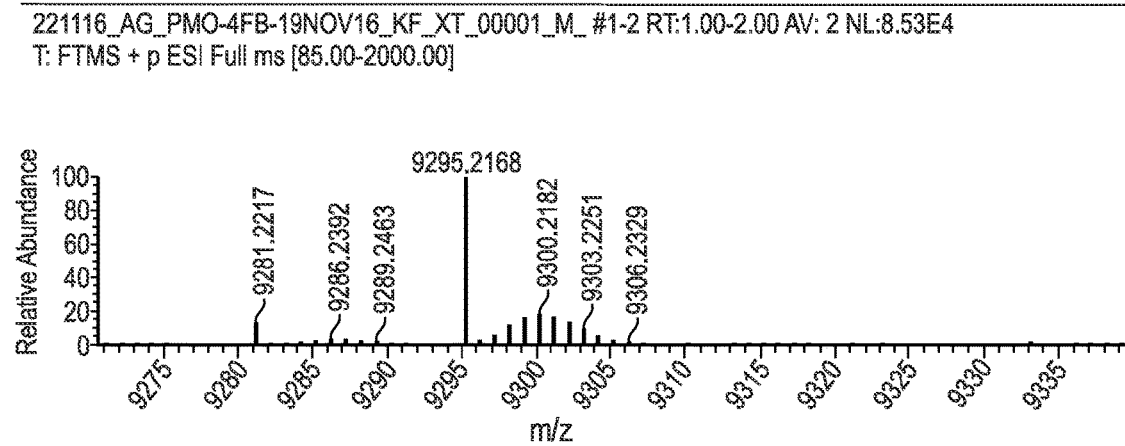

The Spectra were collected at room temperature in H$_2$O spiked with 10% D$_2$O and 10 mM sodium acetate;

FIG. 5a is a schematic diagram of StaP DCCPM depicting variants of linkers and spacers as defined in Table 5;

FIG. 5b is a schematic diagram of DCCPM depicting the synthetic steps for the conjugation of a StaP to a PMO. The PMO is modified to yield a 5' amine group (compound I); the heterobifunctional protein crosslinker Succinimidyl-4-[N-maleimidomethyl] cyclohexane-1-carboxylate (SMCC; compound II) is attached to 5' amine group to yield compound IV; an i,i+4 stapled peptide (compound III) is conjugated to generate the final DCCPM (compound V);

FIG. 5c is a DCCPM of CP8M conjugated to an ON using a SMCC linker (e.g. PMO-CP8M);

FIG. 5d is a DCCPM of HP8M using a HNA linker (PMO-HP8M);

The FITC group here and elsewhere may be any other fluorescent label and is present merely to enable visualization;

FIG. 6 shows a general schematic of a FITC labeled DCCPM in which the n-termini of the FITC labelled PMO (compound I) and the CPA (compound III) are linked via a bi-functional linker disuccinimidyl glutarate (DSG) forming compound VI;

FIG. 7 shows a general schematic diagram of a DCCPM in which a FITC labelled PMO is directly conjugated to a CPA through a shared nitrogen forming compound VII;

FIGS. 8a-o show the liquid chromatography-mass spectrometry conformation of the synthetic steps and the molecular masses of compounds depicted in FIG. 1, FIG. 2 and FIG. 5. All PMOs in this application are fluorescently labelled unless specified otherwise.

Figure 9A:
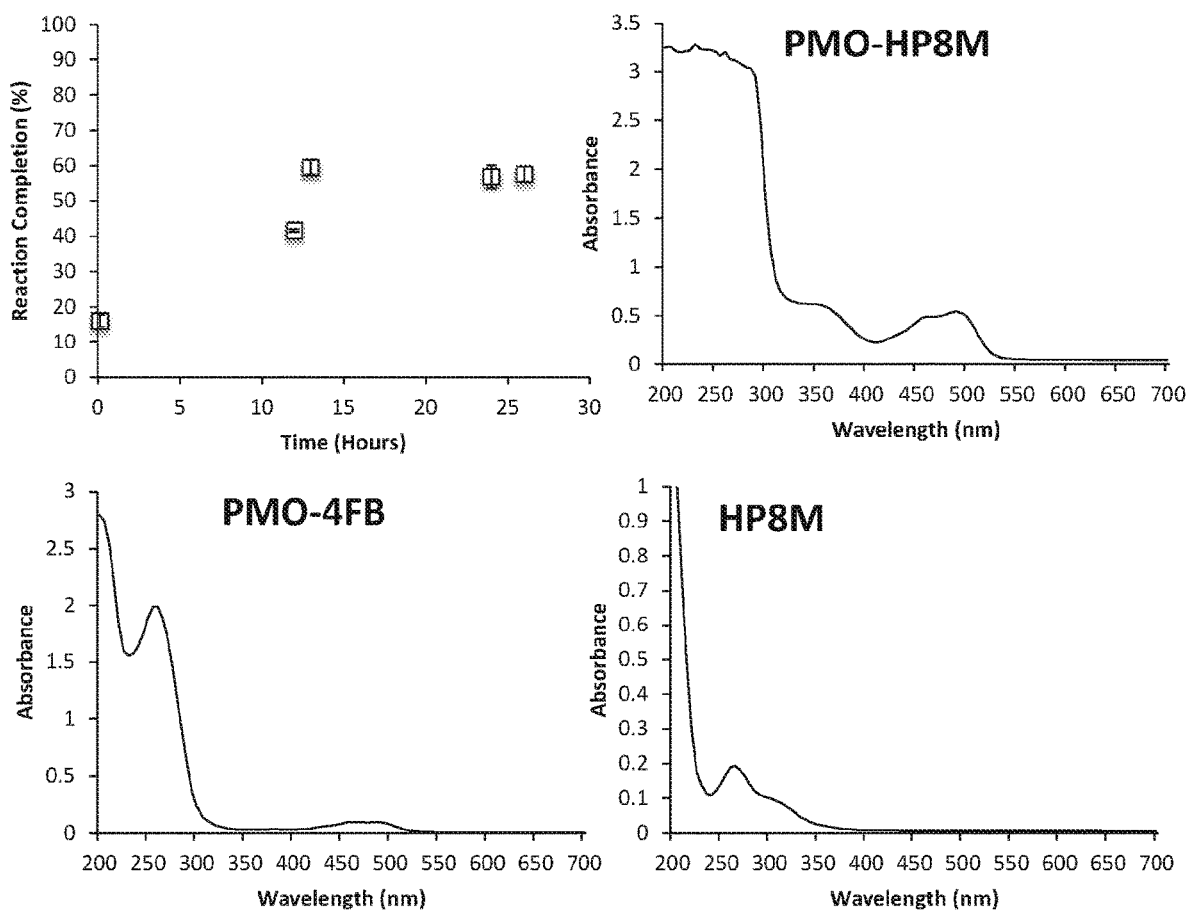
Figure 9B:
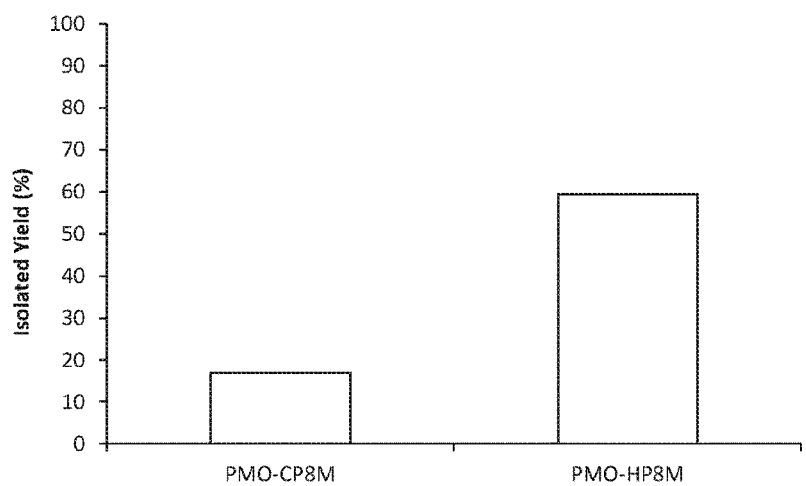

FIG. 8a is a LRMS(API-ES) mass spectra of CP8M-NC. Mass calculated for $C_{76}H_{130}N_{18}O_{16}S^{2+}$ $(M+2H)^{2+}$ 791.5 found 791.8;

FIG. 8b is a LRMS(API-ES) mass spectra of CP8M. Mass calculated for $C_{74}H_{125}N_{18}O_{16}S^{+}$ $(M+H)^{+}$ 1554.9 found 1554.5;

FIG. 8c is a LRMS(API-ES) mass spectra of CBM. Mass calculated for $C_{59}H_{95}N_{16}O_{10}S^{+}$ $(M+H)^{+}$ 1220.5 found 1220.1;

FIG. 8d is a LRMS(API-ES) mass spectra of HP8M. Mass calculated for $C_{77}H_{125}N_{20}O_{16}^{+}$ $(M+H)^{+}$ 1586.9 found 1586.5;

FIG. 8e is a HRMS(LQT-ESI) mass spectra of PMO. Mass calculated for $C_{332}H_{500}N_{153}O_{110}P_{25}$ (M) 9164.1675 found 9164.1882;

FIG. 8f is a HRMS(LQT-ESI) mass spectra of PMO-SMCC. Mass calculated for $C_{344}H_{513}N_{154}O_{113}P_{25}$ (M) 9383.2570 found 9383.2704;

FIG. 8g is a HRMS(LQT-ESI) mass spectra of PMO-CP8M. Mass calculated for $C_{418}H_{638}N_{172}O_{129}P_{25}S^{+}$ $(M+H)^{+}$ 10937.1806 found 10937.2377;

FIG. 8h is a HRMS(LQT-ESI) mass spectra of NF-PMO-CP8M. Mass calculated for $C_{393}H_{619}N_{172}O_{121}P_{255}$ (M) 10490.0372 found 10490.2268;

FIG. 8i is a HRMS(LQT-ESI) mass spectra of PMO-HP8M. Mass calculated for $C_{417}H_{626}N_{173}O_{127}P_{25}$ (M) 10863.1285 found 10863.0716;

FIG. 8j is a LRMS(API-ES) mass spectra of FITC 3+(CP8M-3). Mass calculated $C_{92}H_{132}N_{18}O_{20}S^{2+}$ $(M+2H)^{2+}$ 920.5 found 921.0;

FIG. 8k is a LRMS(API-ES) mass spectra of FITC 2+(CP8M-2). Mass calculated $C_{92}H_{131}N_{17}O_{20}S^{2+}$ $(M+2H)^{2+}$ 913.0 found 913.6;

FIG. 8l is a LRMS(API-ES) mass spectra of FITC 1+(CP8M-1). Mass calculated $C_{92}H_{129}N_{14}O_{20}S^{+}$ $(M+H)^{+}$ 1783.1 found 1782.6;

FIG. 8m is a LRMS(API-ES) mass spectra of FITC+ (CP8M-0). Mass calculated $C_{92}H_{126}N_{11}O_{20}S^{-}$ $(M-H)^{-}$ 1738.1 found 1738.0;

FIG. 8n is a HRMS(LQT-ESI) mass spectra of PMO-4-FB. Mass calculated for $C_{340}H_{503}N_{153}O_{112}P_{25}^{+}$ $(M-H)^{+}$ 9295.1802 found 9295.2168; and FIG. 8o is a HRMS(LQT-ESI) mass spectra of PMO-CP8M-NC. Mass calculated for $C_{420}H_{642}N_{172}O_{129}P_{25}S^{+}$ $(M-H)^{+}$ 10965.2112 found 10965.2162;

FIGS. 9a and 9b demonstrate the comparative conjugation efficiencies of SMCC and HNA linker systems;

FIG. 9a shows the % Conversion of HP8M and PMO-4FB into PMO-HP8M analysed by UV spectroscopy. % Conversion was calculated by $A_{350}$ of the bis-aryl hydrozone bond based on the starting reaction concentration of 705 μM. UV profiles of corresponding starting materials (HP8M and PMO-4FB) and the resulting conjugate (PMO-HP8M); and FIG. 9b shows the % isolated yield of PMO-CP8M and PMO-HP8M.

Figure 10A:
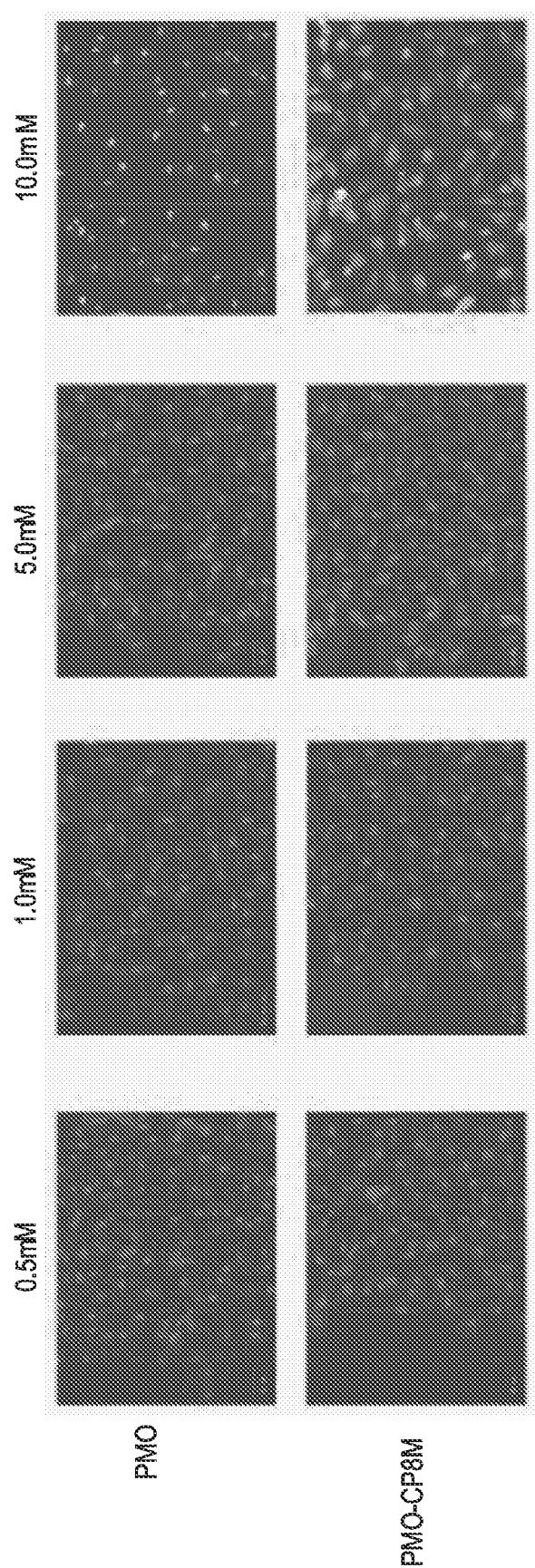

FIG. 10a shows florescence microscopy images demonstrating a dose dependent increase in DCCPM delivery into a human osteosarcoma cell line (U2OS) maintained in culture, without transfection reagent. The biologically active compound was a PMO with a sequence:

```
SEQ ID NO 1:
5'GGCCAAACCTCGGCTTACCTGAAAT3'
```

Figure 10B:
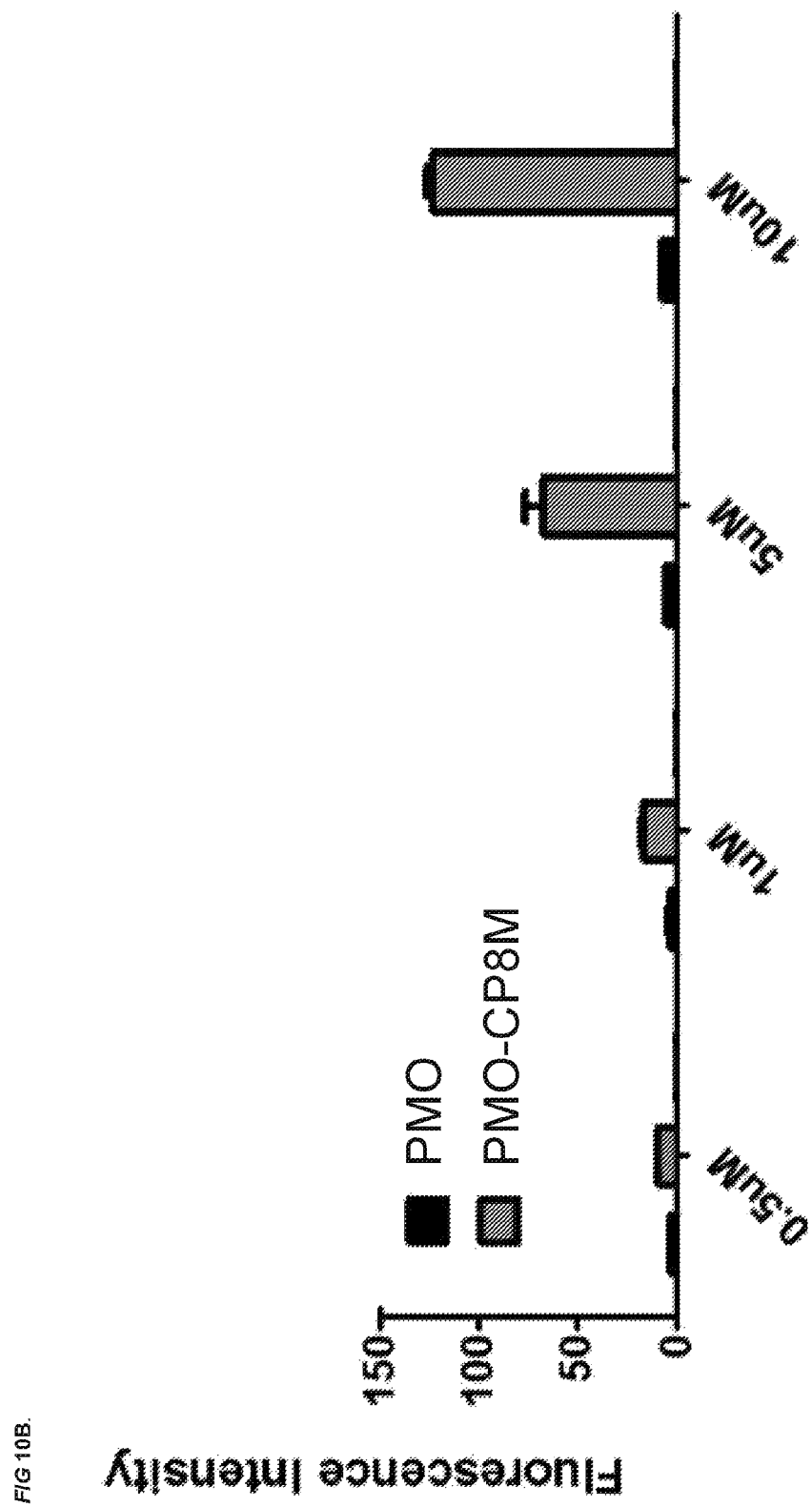
Figure 11:
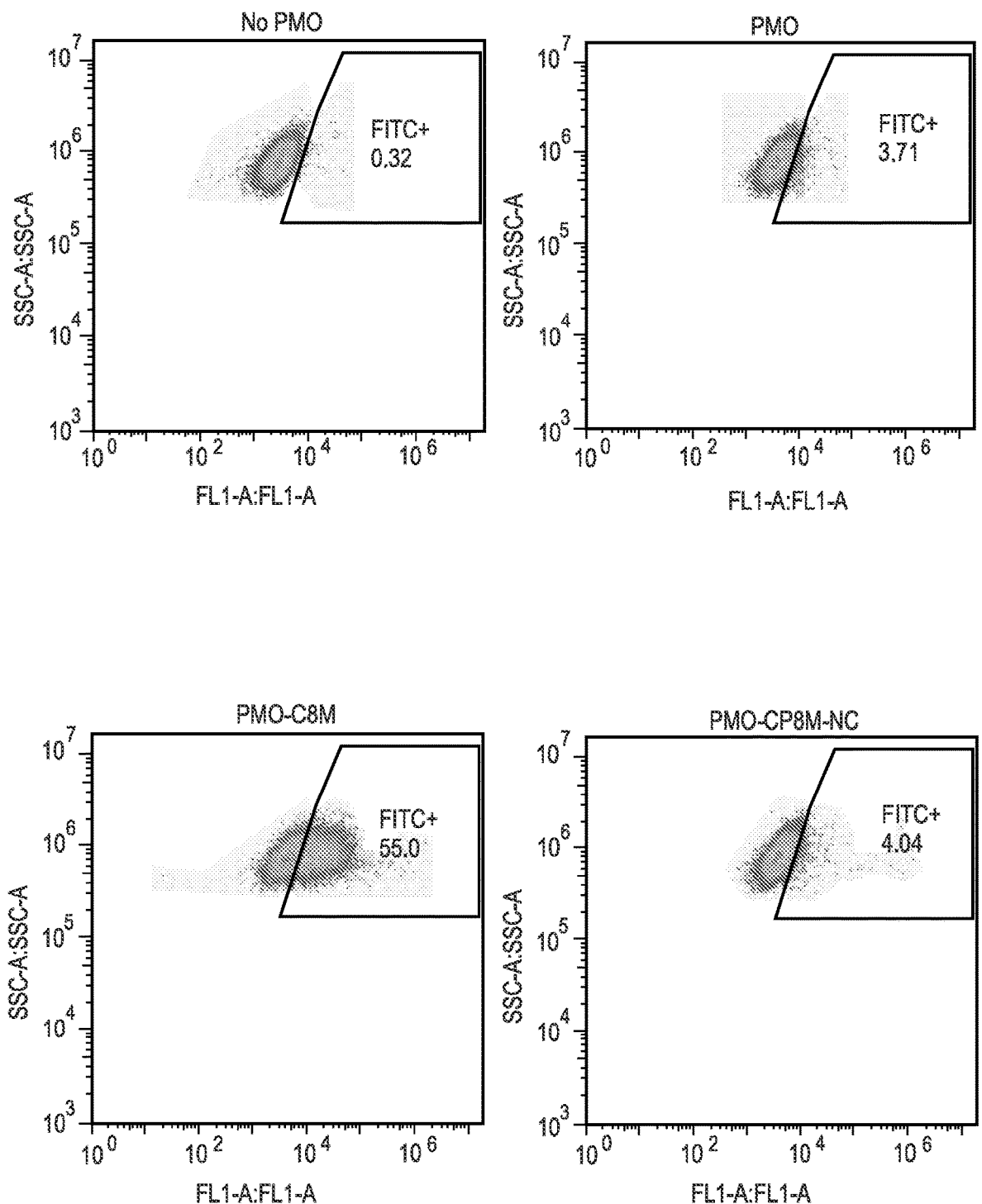

(an antisense reagent targeted to exon 23 of the mouse dystrophin gene, that causes the exclusion of exon 23 during mRNA splicing maturation); the bi-functional linker was a PEGylated SMCC; and the StaP was RKF-S5-RLF-S5 (SEQ ID NO: 57). This configuration of DCCPM is depicted as PMO-CP8M in the subsequent figs; unconjugated PMO acts as a control. All compounds were added to U2OS cells maintained in culture, without transfection reagent for 4 hours;

FIG. 10b is a graphical representation of the delivery of PMO and PMO-CP8M into a human osteosarcoma cell line (U2OS) maintained in culture without transfection reagent;

FIG. 11 is the analysis of PMO uptake into HEK293T cells by flow cytometry. Cells were incubated without PMO or with 1 μM PMO, 1 μM PMO-C8M or 1 μM PMO-CP8M-NC (all fluorescein-labelled) at 37° C. for 4 hours. Fluorescence was measured after washing the cells with PBS.

Figure 12A:
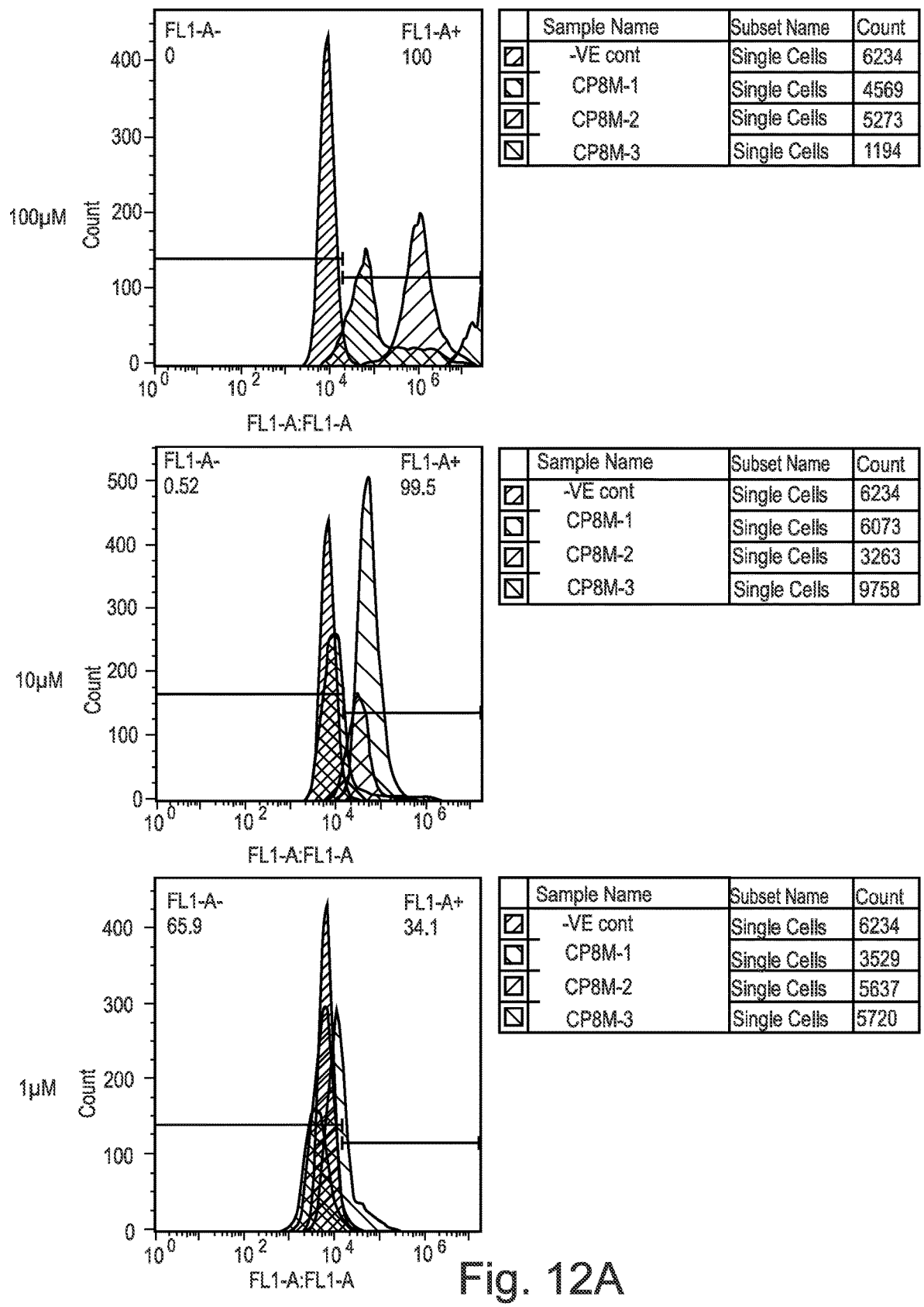
Figure 12B:
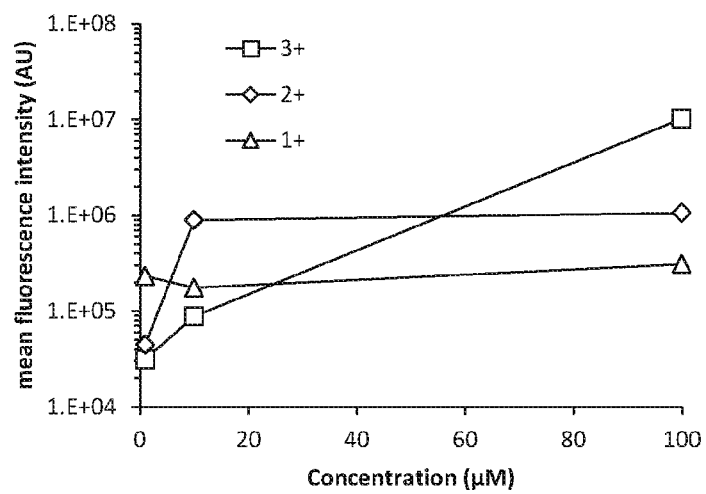
Figure 13:
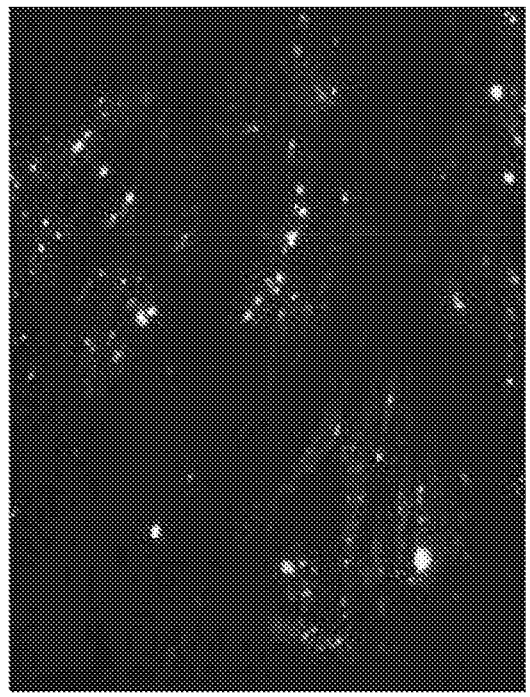
Figure 13:
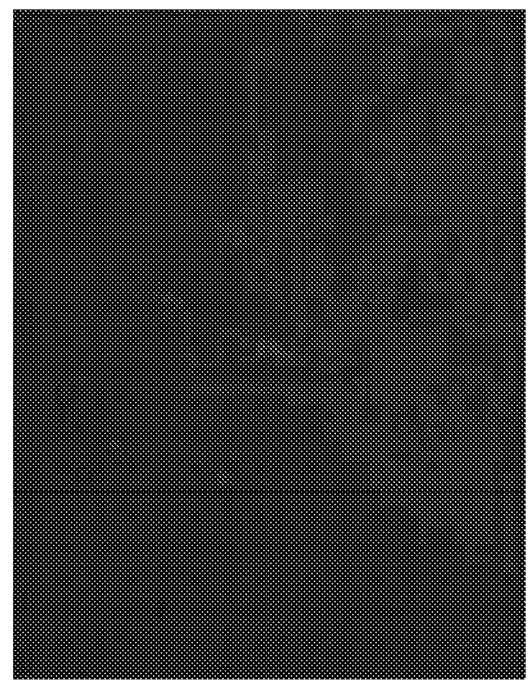

FIG. 12a shows flow cytometry analysis of HEK293T cells treated with FITC+3 (CP8M3), FITC+2 (CP8M-2) and FITC+1 (CP8M-1) without transfection reagent for 4 hours;

FIG. 12b shows flow cytometry analysis of HEK293T cells treated with FITC+3 (CP8M3), FITC+2 (CP8M-2) and FITC+1 (CP8M-1) without transfection reagent for 4 hours. The graph represents mean fluorescent intensity of FL1;

FIG. 13 shows fluorescence microscopy images either 5 μM PMO-CP8M or 5 μM PMO delivery into a mouse cell line that harbours the mdx mutation of the dystrophin gene (H2K mdx) maintained in culture, without transfection reagent, in which the PMO has a fluorescent label.

Figure 14:
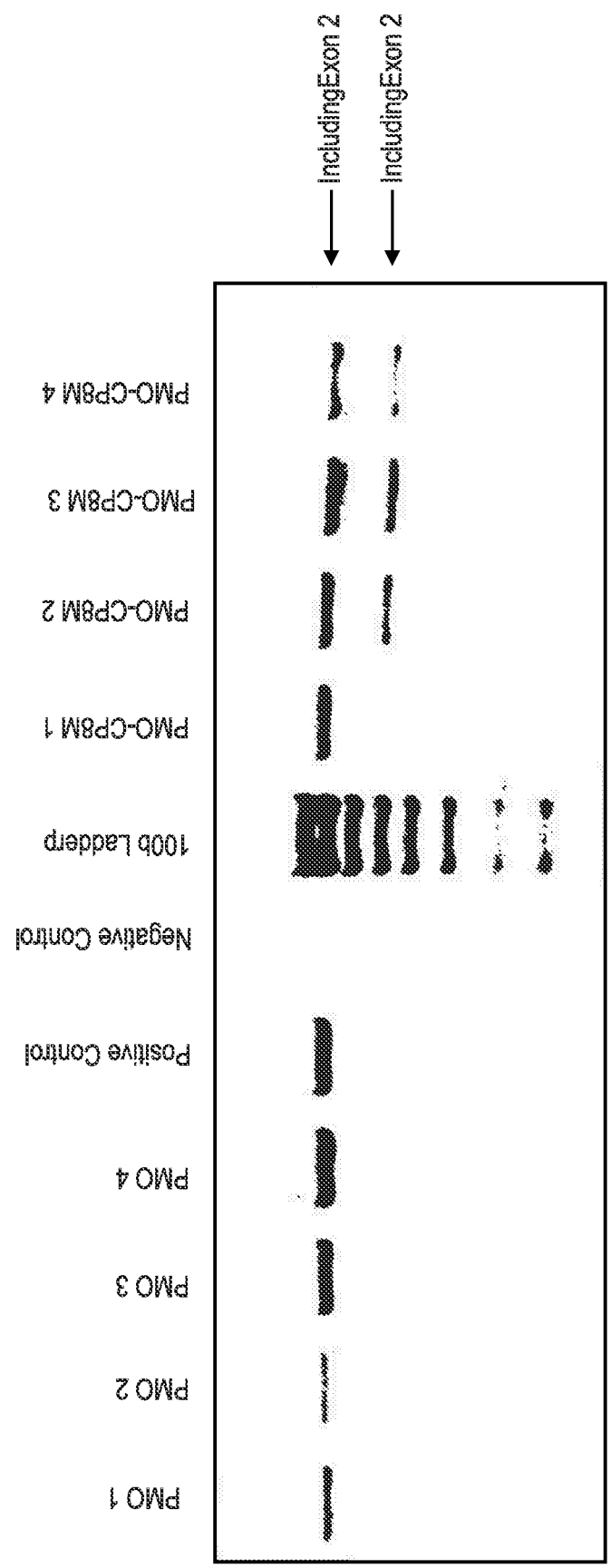
Figure 15:
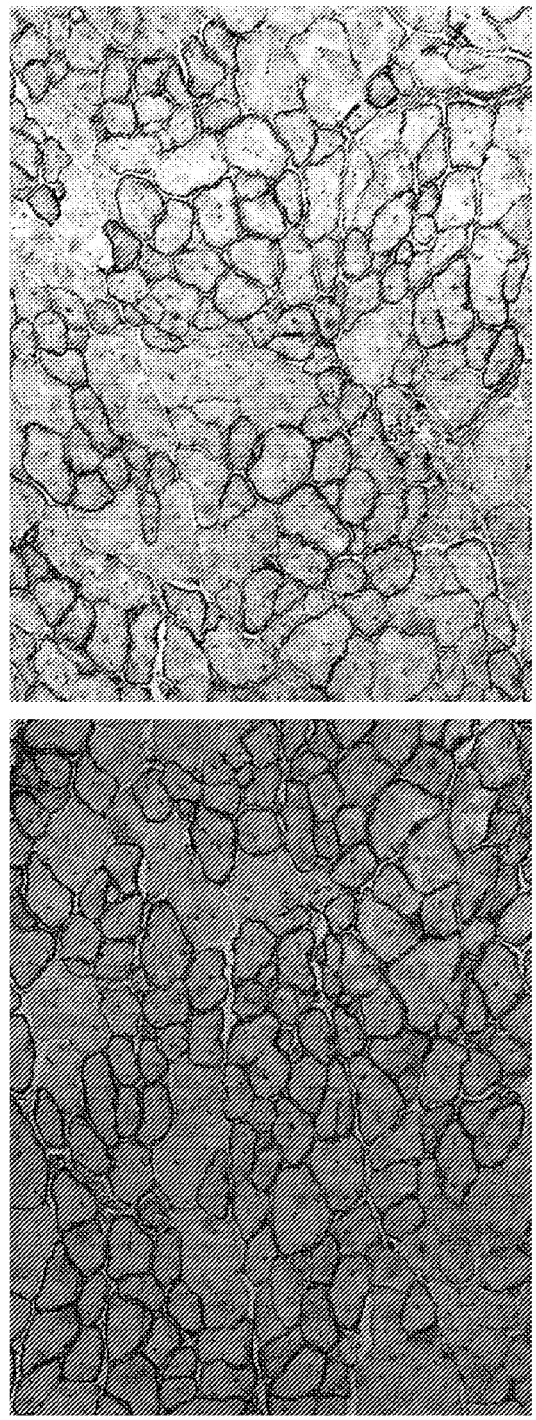
Figure 16:
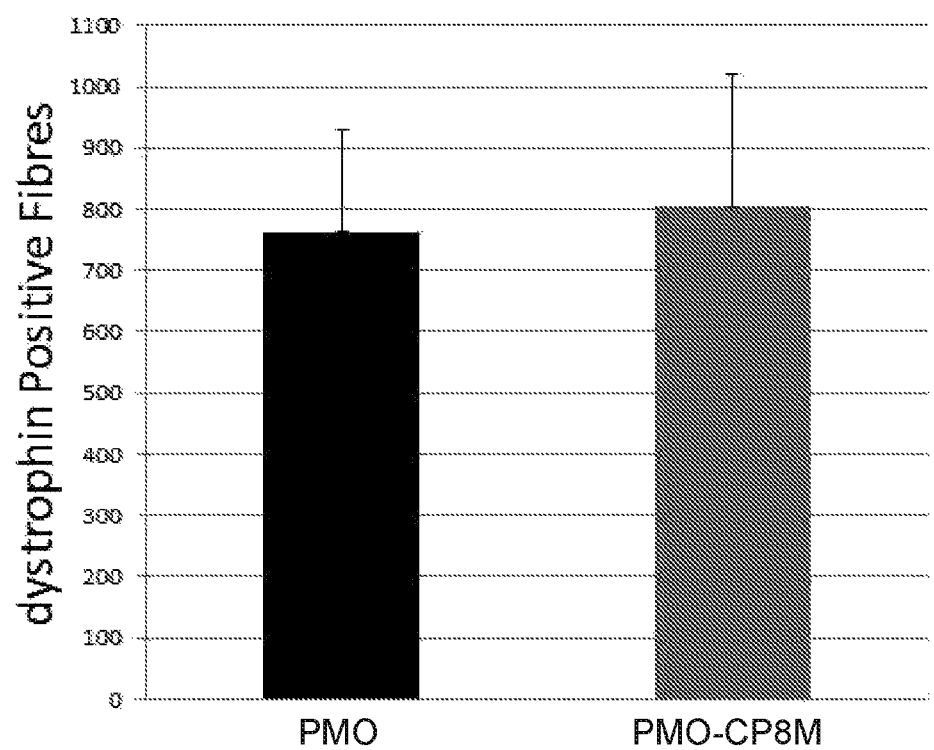
Figure 17A:
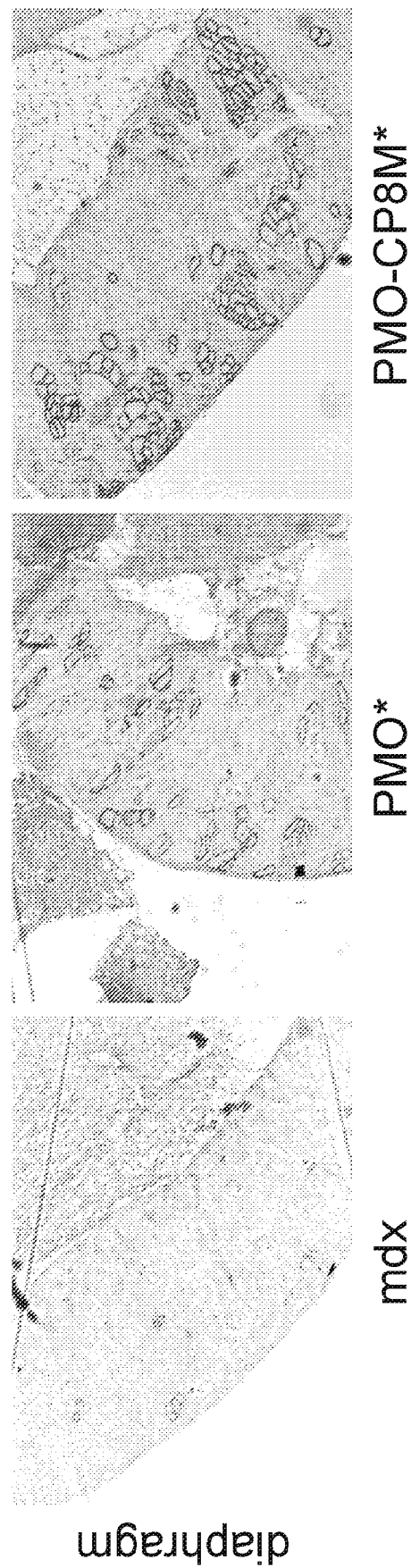
Figure 17B:
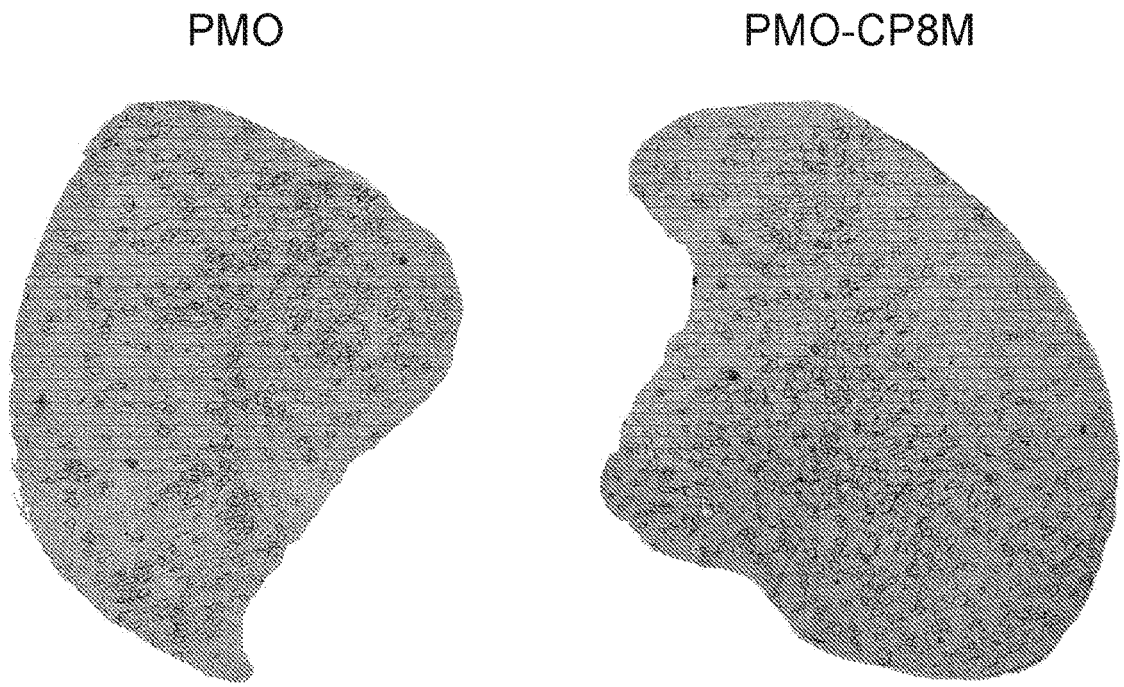
Figure 17C:
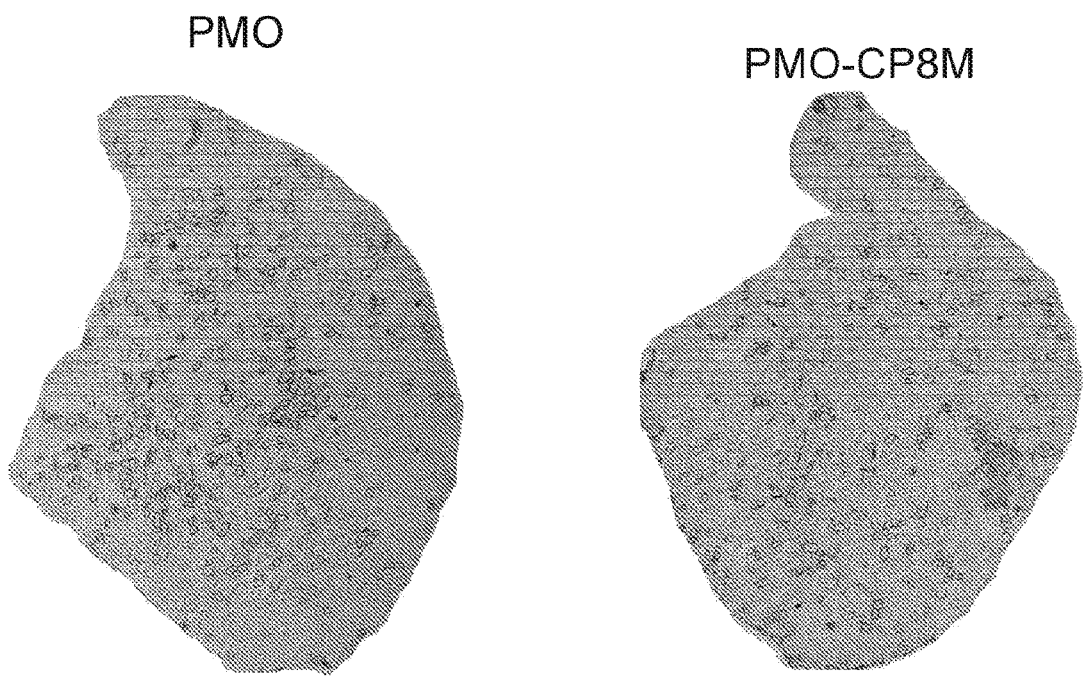
Figure 17D:
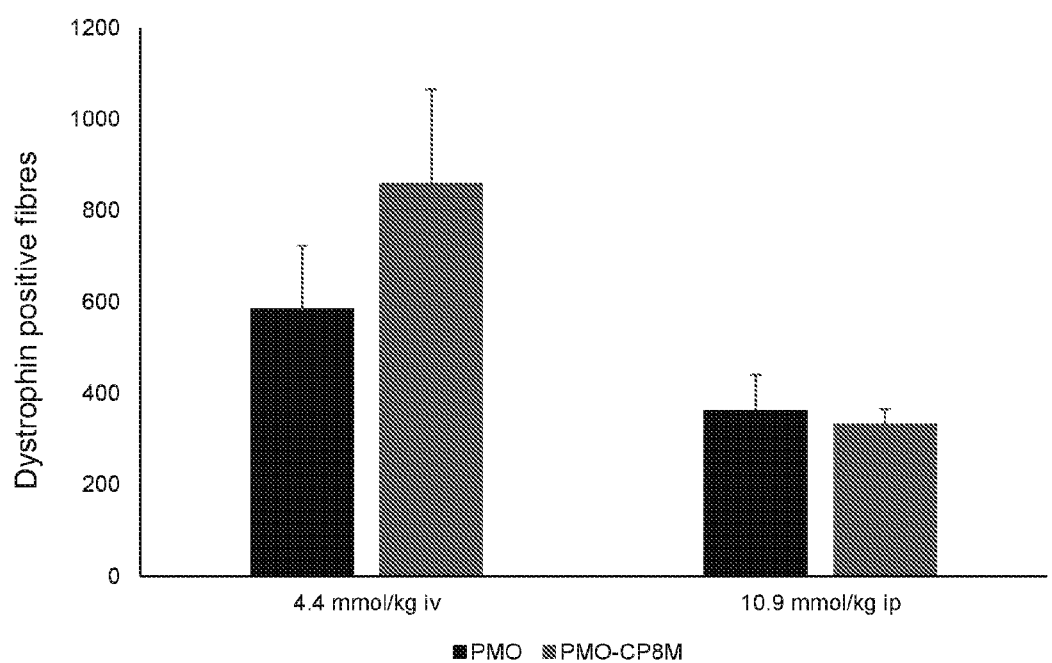
Figure 18A:
Figure 18A:
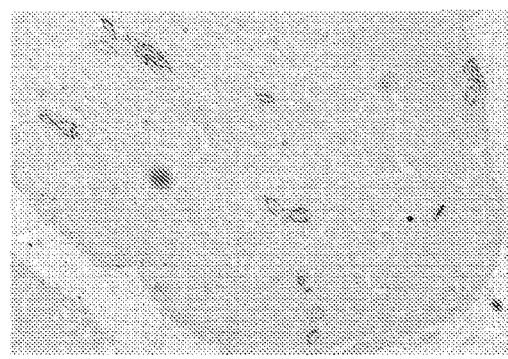
Figure 18B:
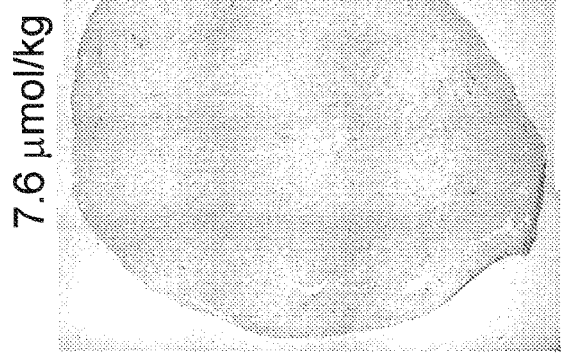
Figure 18B:
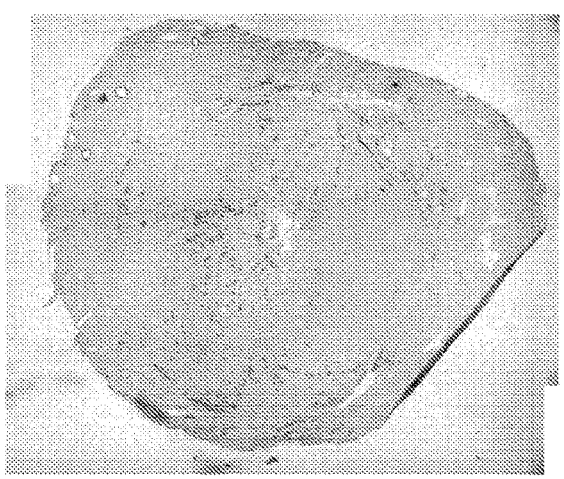
Figure 18C:
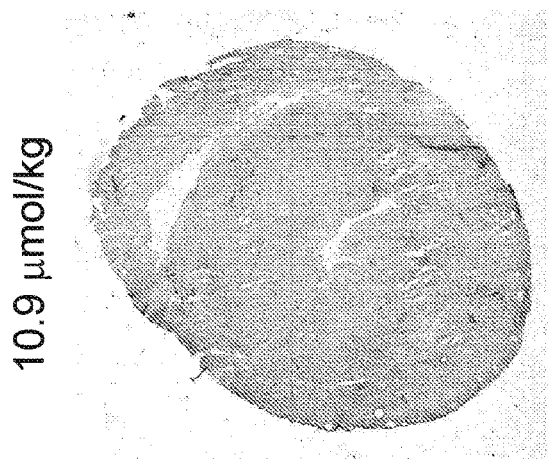
Figure 18C:
Figure 18D:
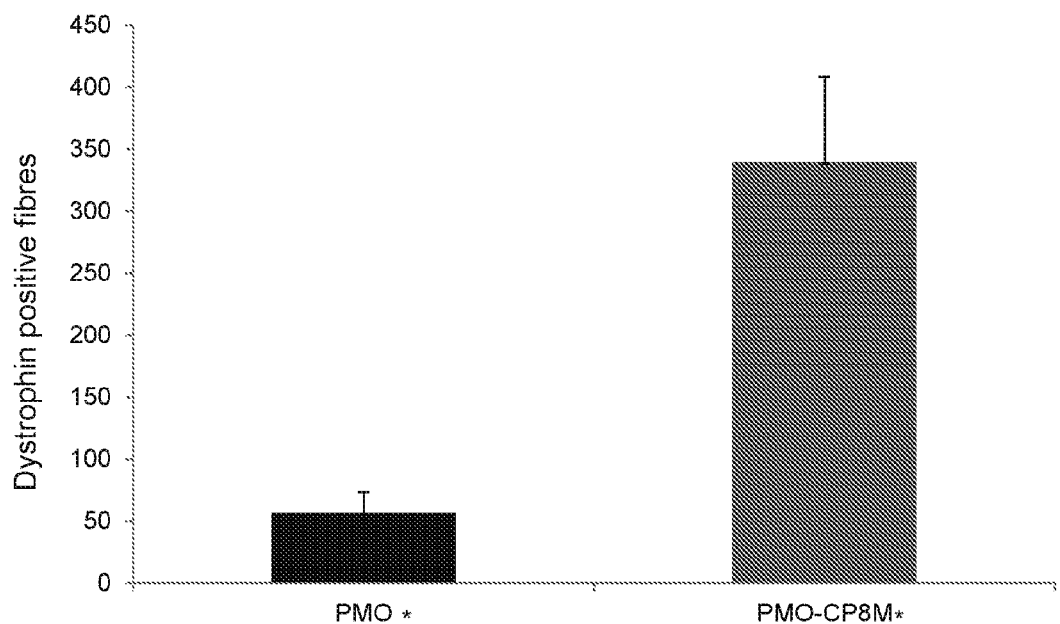
Figure 18E:
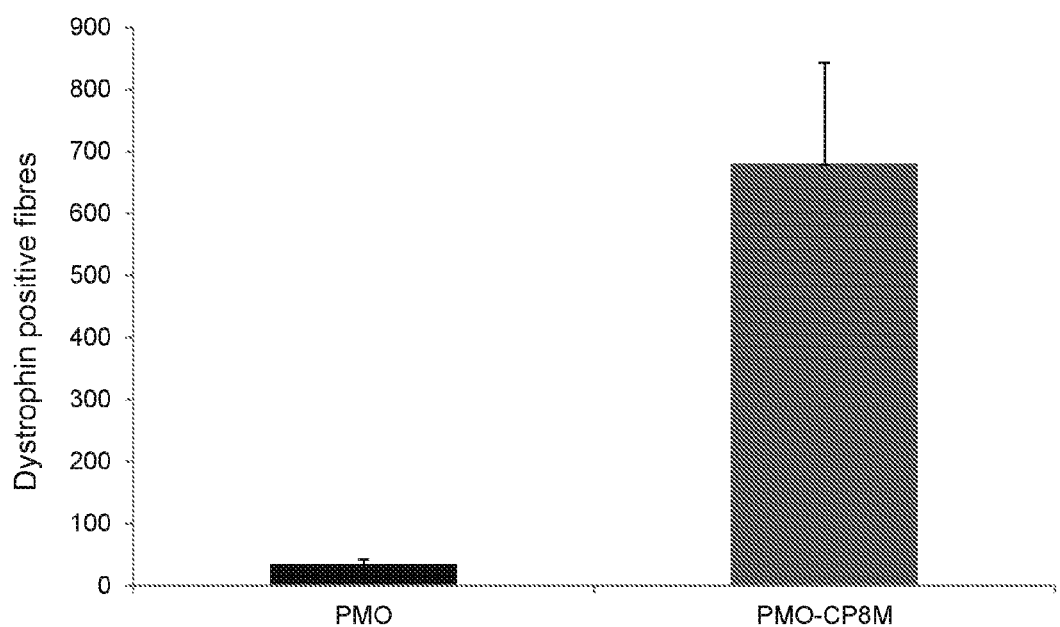
Figure 19:
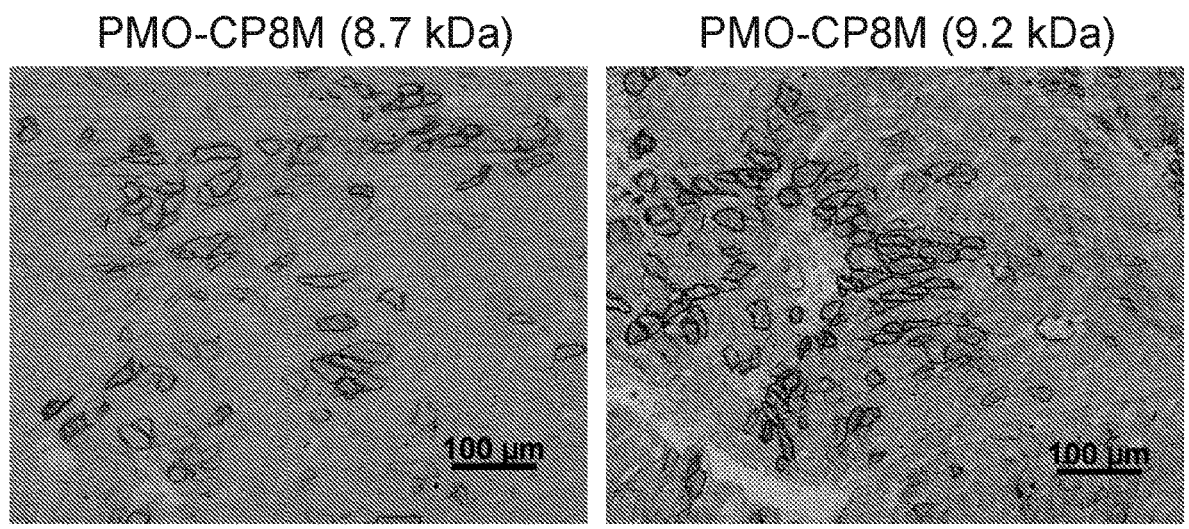
Figure 20:
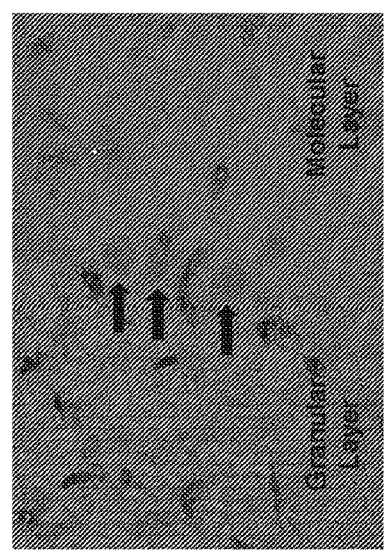
Figure 20:
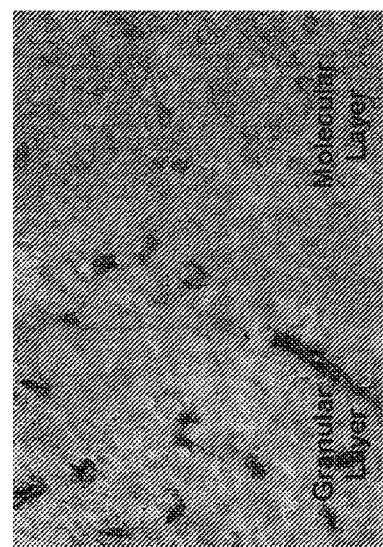
Figure 20:
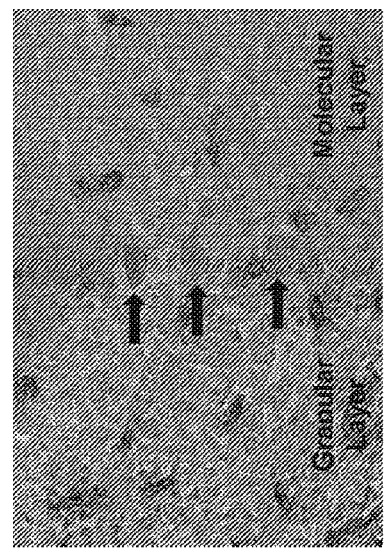
Figure 21:
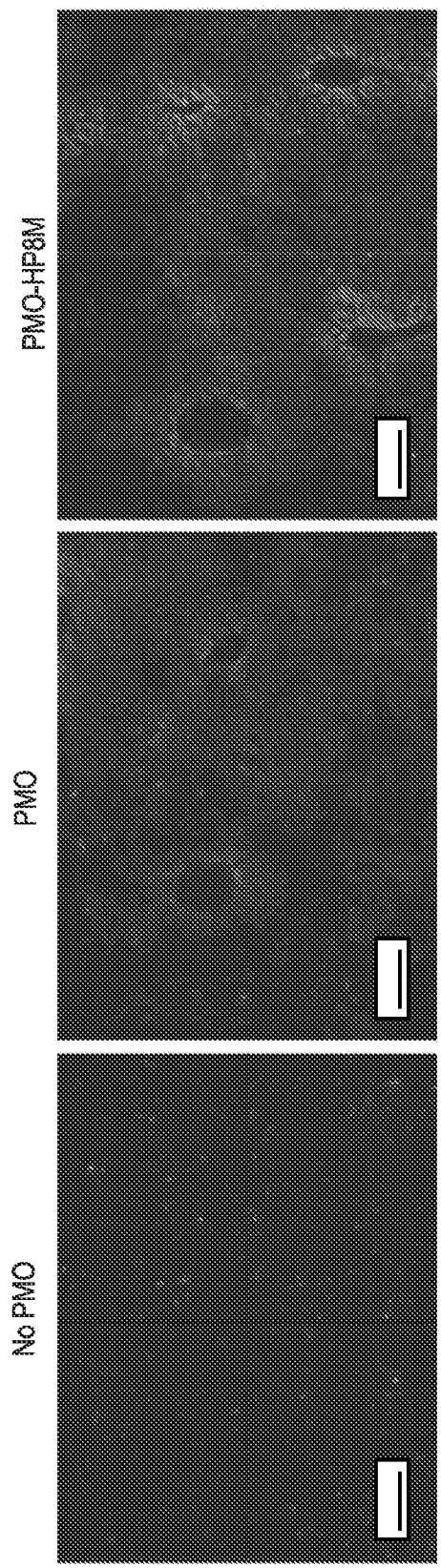

FIG. 14 shows an agarose gel electrophoresis image demonstrating that exon exclusion of the mouse dystrophin exon 23 is restricted to H2K mdx cells that have been transfected with 5 μM PMO-CP8M but not those treated with 5 μM PMO alone, in which the PMOs have a fluorescent label. 24 hours after incubation with PMO-CP8M or PMO, H2K mdx cells were recovered and RNA isolated. The RNA was reversed transcribed and an amplification between exon 20 and 26 of the mouse dystrophin gene, followed by a nested amplification between exon 20 and 26 was performed to yield a full length product of 901 bp fragment if exon 23 is present or 688 bp fragment if exon 23 is excluded;

FIG. 15 shows immuno-cytochemical staining for dystrophin from Tibialis anterior muscles of mdx mice following a single intramuscular injection of either 2.2 nmol PMO-CP8M or 2.2 nmol PMO into the Tibialis anterior muscle (dose in respect of molarity of PMO). Muscles were recovered 7 day post administration;

FIG. 16 shows a graphical representation of the number of skeletal muscle fibre being positive for an immuno-cytochemical staining for dystrophin from Tibialis anterior muscles of mdx mice injected with either 2.2 nmol PMO-CP8M or 2.2 nmol PMO. All dose are given in respect of the molarity of PMO;

FIGS. 17 *a-d* show immuno-cytochemical staining for dystrophin from skeletal muscles of mdx mice:

FIG. 17*a* is from the diaphragm following a single intraperitoneal injection of 1 μmol/kg PMO-CP8M or 1 μmol/kg PMO [* denotes non fluorescent labelled PMO]. Muscles were recovered 7 days post administration;

FIG. 17*b* is following multiple intravenous injections—total 4.4 μmol/kg PMO-CP8M or 4.4 μmol/kg PMO;

FIG. 17*c* is following multiple intraperitoneal injections—total 10.9 μmol/kg PMO-CP8M or 10.9 μmol/kg PMO; and FIG. 17*d* is a graphical representation of the number of skeletal muscle fibre being positive for an immuno-cytochemical staining for dystrophin following intraperitoneal administration. All dose are given in respect of the molarity of PMO [* denotes non fluorescent labelled PMO]. Muscles were recovered 14 days post administration;

FIGS. 18*a-c* show immuno-cytochemical staining for dystrophin from heart muscles;

FIG. 18*a* is of mdx mice following a single intraperitoneal injection of 1 μmol/kg PMO-CP8M or 1 μmol/kg PMO. Muscles were recovered 7 days post administration;

FIG. 18*b* is following multiple intraperitoneal injections—total 7.6 μmol/kg PMO-CP8M or 7.6 μmol/kg PMO. Muscles were recovered 14 days post administration;

FIG. 18*c* is following multiple intraperitoneal injections—total 10.9 μmol/kg PMO-CP8M or 10.9 μmol/kg PMO;

FIG. 18*d* is a graphical representation of the number of cardiac muscle fibre being positive for an immuno-cytochemical staining for dystrophin following a multiple intraperitoneal injections—total 7.6 μmol/kg PMO-CP8M or 7.6 μmol/kg PMO; and FIG. 18*e* is a graphical representation of the number of cardiac muscle fibre being positive for an immuno-cytochemical staining for dystrophin following multiple intraperitoneal injections—total 10.9 μmol/kg PMO-CP8M or 10.9 μmol/kg PMO. All dose are given in respect of the molarity of PMO [* denotes non fluorescent labelled PMO]. Hearts were recovered 14 days post administration;

FIG. 19 shows immuno-cytochemical staining for dystrophin from heart muscles of mdx mice following intraperitoneal injections of PMO-CP8M with a total cargo size of 8.7 KDa and PMO-CP8M with total cargo size of 9.2 KDa. Hearts were recovered 14 days post administration;

FIG. 20 shows immuno-cytochemical staining for dystrophin from the cerebellum of mdx mice following a single intraperitoneal injection of 1 μmol/kg PMO-CP8M or 1 μmol/kg PMO. All dose are given in respect of the molarity of PMO [* denotes non fluorescent labelled PMO]. Cerebella were recovered 7 days post administration; and FIG. 21 demonstrates in vivo liver cell uptake of fluorescein-labelled PMO after intravenous administration of PMO or PMO-HP8M to mdx mice (single intravenous injection, 1 μmol/kg, analysed 2 weeks post-injection). Un-injected mdx mice were used as a negative control.

DETAILED DESCRIPTION

The invention is illustrated with reference to a single example which proves the benefit of the claimed invention.

An exemplary drug carrying cell penetrating molecule (DCCPM) was produced with a FITC label in order to demonstrate cellular uptake (Example 1).

The exemplary DCCPM comprises:
i) a biologically active compound (BAC)—(see Table 4 for non-limiting examples);
ii) a cell penetrating agent (CPA) which is a stabilized peptide (See Table 2 for non-limiting examples); and
iii) a bi-functional linker (BFL) (see Table 5 for non-limiting examples).

The three components forming the DCCPM are described in more detail below, although as illustrated in FIG. 5, the BAC and CPA can be linked directly (FIG. 6).

1. The Biologically Active Compound.

The biologically active compound is any compound that can exert a biological effect within a biological cell. Preferably, though not essentially, the BAC is one which will impact on the expression of one or more endogenous or exogenous genes. Examples include nucleic acids, DNAzymes, ribozymes, aptamers and pharmaceuticals. Preferred biologically active compounds for use in the present invention include electrically neutral oligonucleotides (charge −1 to +1 at physiological pH—about 7.5) such as polynucleic acids (PNAs) or PMOs or their modified derivatives that might impart a small electric charge (either positive or negative).

The biologically active compound may be used as a steric blocking compound to suppress or enhance: i) RNA splicing; ii) protein translation or iii) other nucleic acid:nucleic acid or nucleic acid:protein interactions, altering the gene expression of endogenous or exogenous (pathogen derived) genes.

The hybridisation of ON's to specific RNA sequence motifs prevents correct assembly of the spliceosome, so that it is unable to recognise the target exon(s) in the pre-mRNA and hence excludes these exon in the mature gene transcript. Exclusion of an in-frame exon can lead to a truncated yet functional gene product; exclusion of an out of frame exon results in a frame-shift of the transcript, potentially leading to a premature stop codon and a reduction in the target gene expression level.

Additionally, ON's can be designed to target 5' translation initiation start sites of endogenous or viral gene transcript(s) to prevent binding of the translational machinery. Using ASO to suppress viral translation is a well-established technology and has progressed into clinical trials for viral haemorrhagic fevers such as Marburg and Ebola.

Also, ON can be designed to target 3' untranslated region of an endogenous transcript that alters the stability of the transcript. Such targets include, and are not limited to, poly adenylation and/or cleavage sites of the transcript.

Also, ON can be designed to form aptamers such that the secondary and tertiary structures can bind proteins or other cellular targets thus impacting on specific gene expression levels.

Non-limiting exemplary ON chemistries are illustrated in Table 4.

In the non-limiting example illustrated, the target is exon 51 of the dystrophin gene and comprises the sequence:

```
SEQ ID NO 2:
5'CUCCAACAUCAAGGAAGAUGGCAUUUCUAG3'
```

2. The Cell Penetrating Agent (CPA) which is a Stabilized Peptide

The cell penetrating agents of the invention are stabilized peptides.

The peptides may be stabilized by stapling, to form a stapled peptide (StaP), or by stitching to form a stitched peptide (StiP)

All-hydrocarbon staples and stitches may confer a property, e.g. an α-helical structure, protease resistance, cellular penetrance, and biological activity.

Non-limiting examples of stapled and stitched peptide sequences are illustrated in Table 2 and include peptide sequences including S5, S8 and B5 (as defined in Table 2).

Stabilisation of e.g. the α-helical structure can be achieved by, for example, a ring-closing metathesis and may be catalysed by a variety of ruthenium catalysts including Grubbs generations 1 and 2 and Grubbs-Hoyveda generations 1 and 2.

All the peptide components (amino acids, unnatural amino acids, unstapled/unstitched, partially stapled/stitched and stapled/stitched peptides) may exist in specific geometric or stereoisomeric forms. All compounds include cis- and trans-isomers, (R)- and (S)-enantiomers, diastereoisomers and racemic mixtures thereof.

Preferred isomer/enantiomers will be enriched to give a greater proportion of one particular isomer or enantiomer. Embodiments thereof may be made of greater than 90%, 95%, 98% or 99%, by weight, of a preferred isomer/enantiomer.

Non-limiting examples of unnatural amino acids used in stabilising a peptide structure are illustrated in Table 1.

In one embodiment the applicant employs α,α-disubstituted unnatural amino acids bearing all-hydrocarbon tethers (e.g. α-methyl, α-pentenyl glycine).

For single turn stapling, one embodiment could employ a (S)-pentenylalanine (S5) at, e.g. i, i+4 positions, and in another embodiment, for double turn stapling, a combination of either R-octenylalanine/S-pentenylalanine (R8/S5) or S-octenylalanine/R-pentenylalanine (S8/R5) at e.g. i, i+7 positions can be used. The same pairings can be used to install more than one staple within a given peptide template. S5 can be substituted at i, B5 at position i+4 positions, and S8 can be been substituted at i, i+4, i+11 positions to generate stitched peptides. The S5 configured amino acid and its enantiomer R5, or S8 configured amino acid and its enantiomer R8, differ only in the opposite stereochemical configuration of the staple they bear.

Based upon the inclusion of a single or a double turn staple, peptides may comprise of one or more of the sequences in Table 2. Based upon the specific peptides shown in Table 2, a person skilled in the art can easily envisage peptides with 3, 4, 5 or more turn stabilising staples.

The hydrocarbon bridge may be composed of a double hydrocarbon bond or a single hydrocarbon bond.

In one embodiment the cell penetrating agent has a stitch or staple peptide comprising the sequence RFK-S5-RLF-S5 (SEQ ID NO: 57).

In another embodiment the peptide is a branched stapled peptide. The branched stapled peptide comprises of 2 or more chains of peptides. Branched peptides may be formed using any method know to the art; in one embodiment a lysine residue is used to branch two peptide chains.

Functional derivatives of disclosed peptide sequences could be used. Functional derivatives may have representative fragments or homologues or peptides that include insertions to the original peptide. Typical derivative would have 70%, 80%, 90% or more of the original peptide sequence and may have up to 200% of the number of amino acids of the original peptide. The derivatives would be used to enhance the delivery of a biologically active compound.

Peptide sequence can include modified amino acids to include functional groups that permit the addition of other moieties. Non-limiting examples of such moieties include an acetyl, a cholesterol, a fatty acid, a polyethylene glycol, a polysaccharide, an aminoglycan, a glycolipid, a polyphenol, a nuclear localising signal, a nuclear export signal, an antibody and a targeting molecule.

3. Bi-Functional Linker

A bi-functional linker may be used to link the BAC to the CPA.

Preferred linkers will link between, for example, an amine group on the BAC and a sulfhydryl (thiol) group (usually a cysteine residue) on the CPA terminus. Examples of substrates to achieve this include, but are not limited to, SMCC (succinimidyl 4-(N-maleimidomethyl)cyclohexane-1-carboxylate), AMAS (N-α-maleimidoacet-oxysuccinimide ester, BMPS (N-β-maleimidopropyl-oxysuccinimide ester), GMBS (N-γ-aleimidobutyryl-oxysuccinimide ester), DMVS (N-δ-maleimidovaleryl-oxysuccinimide ester, EMCS (N-ε-malemidocaproyl-oxysuccinimide ester), and LC-SMCC (Succinimidyl 4-(N-maleimidomethyl)cyclohexane-1-carboxy-(6-amidocaproate) as exemplified in Table 5.

Another preferred linker system is hydrazynal nicotinic acid (HNA), however if the BAC is a PMO, the PMO is modified to incorporate 4 formyl benzioic acid.

Other linkers such as DSG (disuccinimidyl gluterate) and DSCDS (disuccinimidyl-cyclohexl-1,4-diester) will include the ability to link the 5'-amino group of the BAC to the N-terminus of the CPA (Table 5, entries 8 and 9).

Linkers may include other elements that confer a desirable property on the DCCPM e.g. spacer between ON and CPA or an element that will enhance solubility, for example a PEGylated element as illustrated in FIGS. 5c and 5d. Non-limiting examples are shown in Table 5.

The biologically active compound is covalently attached to the chimeric cell delivery peptide. Again, this can be done using any method known in the art. Preferably, the cell delivery peptide is attached to the biologically active compound by means of a disulphide bridge or a thiol maleimide linker e.g. SMCC; the attachment may be by means of an amide linker or an oxime linker or a thioether linker.

EXAMPLE 1: (PROOF OF PRINCIPLE)

DCCPM to Enhance RNA Steric Blocking in Treating Duchenne Muscular Dystrophy (DMD).

Introduction

Duchenne muscular dystrophy (DMD) is the most common inherited lethal childhood disease in the world, with a worldwide incidence of approximately 1 in 4000 live births[33]. This severe muscle-wasting disorder is caused in the majority of families by gene mutations leading to disruption of the reading frame and premature truncation of the protein dystrophin[34,35].

RNA splicing suppression of the DMD transcript has particular promise. The hybridisation of ASOs to specific RNA sequence motifs prevents correct assembly of the spliceosome, so that it is unable to recognise the target exon(s) in the pre-mRNA and hence excludes them in the mature gene transcript. ASO-mediated RNA splicing suppression resulting in the re-expression of a truncated, yet functional dystrophin protein has been demonstrated in vitro and in the pre-clinical mdx mouse model[29,36-41], which led to clinical development programs[8,13].

Although intravenously administered PMOs have demonstrated a dose-dependent increase in dystrophin re-expression with some functional benefit[13,42], skeletal muscle dystrophin restoration is still very variable between patients after many multiple administrations. Importantly, many other target tissues (e.g. brain and heart) remain refractory to PMO transfection even when repeat administration or high dose strategies are employed[27-29].

To date unmodified CPA conjugation improves PMO bio-distribution and serum stability[30-32], however toxicity is still a major roadblock for pipeline development[19].

Applicant hypothesised that a CPA based upon a stabilized e.g. StaP (or StiP) conjugated to a PMO known to cause RNA splicing suppression of the DMD transcript, would lead to a greater level of dystrophin restoration and re-expression of dystrophin in tissues refractory to naked PMO without the potential for CPA related toxicity.

Materials and Methods

Nuclear Magnetic Resonance (NMR) Analysis of StaP $^1$H NMR spectra was recorded using a Bruker Avance III 500 (500 MHz) spectrometer. Samples were dissolved in $H_2O$ with 10% $D_2O$ and 10 mM sodium acetate.

NOESY spectra were recorded with a 12626.263 Hz sweep width, 4096 complex points (DQD acquisition mode) in the direct dimension and 1024 indirect points (States-TPPI acquisition mode). A NOESY mixing time of 250 ms was used to provide cross peaks with high signal to noise while largely avoiding spin diffusion. A pre-saturation pulse on water and a 3-9-19 pulse sequence with 20% Z-gradients (4,5) aided solvent suppression. TOCSY spectra were recorded with the same spectral width and resolution as the NOESY with a homonuclear Hartman-Hahn transfer using the MLEV17 sequence for an 80 ms mixing time (6). Two power levels were used for excitation (3 dB) and spinlock (12.2 dB). Water suppression was achieved as with the NOESY.

High Resolution Mass Spectroscopy

High-resolution mass spectra were recorded on a Thermo scientific LQT Orbitrap XL under electron spray ionization conditions (ESI) or where indicated under Atomospheric Pressure Ionisation (API) condition.

Circular Dichroism (CD) Spectroscopy

CD analysis was performed on an Applied Photophysics Chirascan Circular Dichroism spectrometer. Samples were dissolved in $D_2O$ at 0.125 W/W % and data acquired in triplicate at room temperature and subsequently averaged and smoothed using built in qCD software. Graphs were plotted by subtracting a blank $D_2O$ spectrum from the acquired data to provided blank correction.

Synthesis of PMO-CP8M and NF-PMO-CP8M

PMO (22.2 mg, 2.1 µM) was dissolved in PBS (400 µL, 1×) and incubated at room temp after the addition of SMCC linker (6 mg, 18 µM, 9× excess) dissolved in MeCN 100 µL. After 45 mins the mixture was desalted using sephadex g25 hydrated in a PBS 1× and was also used as the eluent. RCM-C-PEG-8Mer (3 mg, 2.5 µM) was mixed immobilised TCEP (750 µL) for 1 h. The SMCC modified PMO was then desalted into PBS/MeCN (500 µL 4:1) and immediately the peptide was eluted from the immobilised TCEP and stirred at room temp for 3 hours before purification on a Waters HLB column.

The solution was loaded onto 4 HLB columns, and washed with milliQ water to remove any salts then 20% MeCN in water and finally PMO-CP8M was removed with 50% MeCN in water. The MeCN content was reduced by rotary evaporation and the conjugate subsequently freeze dried to yield the final lipholysed compound.

Synthesis of PMO-HP8M

Modification of PMO to PMO-4FB.

4-FB (250 mg, 1.5 mM) was dissolved in DMF with COMU (1.2 g, 2.6 mM) and NHS (230 mg, 2.0 mM) and stirred for a few mins. Nb, 4-FB did not fully dissolve until DIEA was added. DIEA (0.54 mL 3.0 mM) was then added upon which the reaction mixture changed from colourless to pale yellow/orange. The reaction mixture was stirred for 1 h and monitored by TLC using 5% MeOH in DCM. The mixture was separated over DCM to remove DMF then purified by flash chromatography using DMC to elute the top spot staining positive with 2,4 DNP. Product was collected as an off white solid 112 mg (30%).

PMO (30.4 mg, 3 µM) was added to a solution of 4-FB and dissolved in Carbonate buffer:MeCN (50% MeCN) and NHS activated 4-FB (10 mg, 32 µM) was added and stirred overnight. The mixture was then desalted using sephadex G25 superfine with water:MeCN as an eluent. MeCN was removed by rotary evaporation and the remaining eluent was then freeze dried. Freeze dried product yielded 24 mg 83% yield.

Conjugation of PMO-4FB to HP8M

HP8M was dissolved in milliq ultra pure water (100 µL) to give a solution of 12 mg/mL. Aldehyde modified PMO (7 mg, 0.76 µM) was dissolved in water/MeCN (300 µL, 1:1) and desalted using sephadex G25 superfine and water/MeCN (1:1) as the eluent. The collected fraction was then diluted to 1 mL total volume in water:MeCN mix (1:1) and PMO content was analysed by UV/vis and found to be 6.5 mg/mL or 705 µM. HNA peptide and Analine (10 mM final conc) was then added and UV/vis monitored for evidence of $A_{354}$ and used to calculate the conjugation of PMO to peptide.

PMO and Peptide Synthesis

PMO were synthesised with a 5' amine group and 3' fluorescein isothiocyanate (FITC) label and purified >90% by Genetool LLC (Philomath, Oreg. USA). All peptides were synthesized following an established protocol using standard Fmoc-peptide chemistry on Rink amide MBHA resin. The coupling reactions were performed by the addition of a mixture of 10 equivalents of the amino acids, 9.9 equivalents of HCTU and 20 equivalents of DIPEA in NMP (equivalents relative to initial loading of Rink amide MBHA resin). The reactions were allowed to proceed for at least one hour. Coupling of non-natural amino acids (R/S5, R/S8 or B5) was performed with 4 equivalents of the amino acid, 3.9 equivalents of HCTU and 10 equivalents of DIPEA in NMP for two hours. The ring closing metathesis reaction of the olefin-containing non-natural amino acids was facilitated with Grubbs I catalyst (benzylidene-bis(tricyclohexylphosphine)-dichlororuthenium) dissolved to approximately 10 mg/mL in 1,2-dichloroethane (DCE) for two hours under nitrogen bubbling. Subsequently, excess catalyst was washed from the resin with DCE and then coupled with an N-terminal FITC. Upon completion, peptides were simultaneously cleaved from the resin and de-protected using a cleavage cocktail containing 95% TFA, 2.5% TIS and 2.5% water. Crude peptides were dissolved in 50% acetonitrile/water, passed through a 0.2 µm syringe filter, and purified by reverse phase HPLC using a C-18 column (Agilent, Palo Alto, Calif.). Compound identification and purity was assessed using coupled LC/MS (Agilent, Palo Alto, Calif.). Purified fractions were pooled and evaporated to remove acetonitrile and trace TFA by Speedvac and then lyophilized to dryness. A non-ring closed peptide was also produced as a control.

Cell Culture and Transfection

U2OS cells (Human osteosarcoma) were cultured in high glucose DMEM supplemented with 10% foetal calf serum (Sigma, UK) at 37° C. under an 8% CO2/92% air atmosphere.

$H_2K$ mdx mouse myoblasts were cultured at 33° C. under a 8% $CO_2$/92% air atmosphere in high-glucose DMEM supplemented with 20% foetal calf serum, 0.5% chicken embryo extract (PAA laboratories Ltd, Yeovil, UK), and 20 units/ml γ-interferon (Roche applied science, Penzberg, Germany). Cells were then treated with trypsin and plated at $8 \times 10^4/cm^2$ in 24-well plates coated with 0.1 mg/ml ECM gel (Sigma). $H_2K$ mdx cells were transfected 24 h after seeding with treatment in a final volume of 0.2 ml of normal growth media. Following 4 hours of transfection, the PMO or PMO-SAP was removed and replaced with DMEM supplemented with 5% horse serum. Fluorescence and RNA extraction was performed 48 hours post transfection.

HEK293T cells (Human embryonic kidney) were cultured in high glucose DMEM supplemented with 10% foetal calf serum (Sigma, UK) at 37° C. under an 8% $CO_2$/92% air atmosphere.

U2OS cells were incubated with PMO or PMO-CP8M at increasing concentration (0.5 µM, 1.0 µM, 5.0 µM and 10 µM) with any facilitation transfection reagent; $H_2K$ mdx mouse myoblasts were incubated with PMO or PMO-CP8M at 5.0 µM: HEK293T cells were incubated with CP8M (1.0 µM, 10 µM and 100 µM) and PMO, PMO-CP8M-NC, PMO-C8M at 1.0 µM. Levels of fluorescence was quantified at 494 nm to determine relative entry of respective compounds by microscopic or flow cytometry methodologies.

RNA Extraction and Nested RT-PCR Analysis

Total RNA was isolated from $H_2K$ mdx mouse myoblasts cells (RNeasy, Qiagen, UK). The RNA was reversed transcribed (nanoscript2, Primer Design UK) and an amplification between exons 20 and 26, followed by a nested amplification between exon 20 and 26 was performed to yield a full length product of 901 bp or 688 bp if the mouse dystrophin exon 23 was excluded. Products loaded in a 1% agarose gel (buffered with tris acetate 40 mM and 1 mM ethylenediaminetetraacetic acid).

Animals mdx mice, with access to chow and water ad libitum, were used in all experiments. All experiments were carried out in the Animal unit, School of Biological Science, University of Reading, Reading, UK according to procedures authorized by the UK Home Office. Mice were killed by $CO_2$ inhalation or cervical dislocation at desired time points, and muscles and other tissues were snap-frozen in liquid nitrogen-cooled isopentane and stored at −80° C.

Administration of PMO or PMO-CP8M

Intramuscular administrations: Tibialis anterior muscles of mdx mice were injected with either 2.2 nmol PMO or 2.2 nmol PMO-CP8M under isoflurane anaesthesia. Systemic administration: mdx mice were subject to a single or repeated intraperitoneal injections of PMO or PMO-CP8M (or non-fluorescently labelled variants) at doses ranging from 1 µmol/kg to 10.9 µmol/kg total delivery; alternatively, mdx mice were subject to single or repeated intravascular injections of PMO or PMO-CP8M ranging from 1 µmol/kg to 4.4 µmol/kg total. A series of tissues were recovered at the end of the experiment that included skeletal muscle, heart, brain and liver.

Histology and Immuno-Cytochemistry

For skeletal muscle, heart and brain, 10 µM cryosections were cut and dystrophin protein was detected using rabbit polyclonal antibody to dystrophin (ab15277; Abcam, Cambridge, UK). Routine haematoxylin and eosin staining was used to assess general pathology and morphology. For liver, 10 µM cryosections were dried and embedded in fluorescence-compatible mounting medium (Dako), and general fluorescence was assessed microscopically at 494 nm.

Flow Cytometry

Uptake of fluorescently-labelled PMO was determined by flow cytometry using an Accuri C6 flow cytometer. PMO-transfected cells were released with trypsin, washed in PBS and kept on ice before analysis. Cell fluorescence in single live cells was determined using FlowJo software after appropriate gating. Untreated cells were used to establish gating settings for the determination of the % fluorescein-positive cells.

Statistical Analysis

All data are reported as mean values ±SEM. Statistical differences between treatment groups and control groups were evaluated by SigmaStat (Systat Software, UK) and student's t test was applied. Significance was accepted for p-values<0.05.

Results

Circular dichroism and the nuclear magnetic resonance data confirmed that the ordered structure of the peptides was as expected and that the stapled peptides adopted an α-helical structure (FIG. 4).

The conjugation of PMO-SMCC with a CPP to form PMO-CP8M has consistently yielded an efficiency of 10%. Surprisingly, adopting a conjugation based upon a PMO modified to incorporate 4 formyl benzioic acid and hydrazynal nicotinic acid (HNA) incorporated into the terminal end of the CPP, increased the efficiency of conjugation to yield PMO-HP8M at 59% (FIG. 9).

PMO was conjugated to the bi-functional linker (a PEGylated SMCC) and a CPP (RKF-S5-RLF-S5 (SEQ ID NO: 57)) as confirmed by mass spectrometry (FIG. 7). Subsequently PMO and PMO-CP8M were transfected into a standard cell line (U2OS) to determine if the CP8M conferred enhanced cell entry to the cell. Naked PMO were refractory to cell entry, giving only a background fluorescence signal, compared to a dose dependent increase in fluorescence with PMO-CP8M (FIGS. 10a and 10b). The lack of signal above background does not allow statistical analyses of the comparative increase in fluorescence, but clearly demonstrated that without the CP8M conjugation, PMO did not enter the cell.

Transfection experiments conducted in the HEK293T human embryonic kidney cells again demonstrated that PMO was refractory to cell entry. Importantly, a non-ring closed variant of CP8M (termed CP8M-NC) also did not result in significant cell entry above that of PMO alone. However a ring closed variant that contains the core sequence RKF-S5-RLF-S5 (SEQ ID NO: 57) demonstrated that when conjugated to a fluorescently labelled PMO (to form PMO-C8M), that the PMO was now efficiently taken into cells (FIG. 11). This confirms that the shape imposed upon the peptide sequence, following a ring closing metathesis, is important to facilitate cellular entry of a DCCPM in which the BAC is an ON, more specifically a PMO.

The formal charge of CP8M is +3 at physiological pH. We also provide data demonstrating that reducing the formal charge within this sequence still leads to a surprising and significant cellular entry of CP8M variants with formal charges of +2 (CP8M-2) and +1 (CP8M-1) (FIGS. 12a and 12b), particularly at lower concentrations. The reduction in charge leads to solubility issues which account for the failure of a dose dependent increase, unlike that observed with CP8M. Alternative excipients or manipulations of the peptide as highlighted in Table 5 and Table 6 are likely to overcome these solubility issues.

When transfection experiments were conducted in the $H_2K$ mdx mouse myoblasts cells, it confirmed the finding that PMO are refractory to muscle cell entry, which was overcome with the conjugation of CP8M (FIG. 13) and that the CP8M mediated delivery of PMO resulted in the steric blockade of RNA editing of the dystrophin transcript, such that exon 23 was excluded from the transcript (FIG. 14). Again, the lack of exon exclusion from the PMO only samples precludes comparative statistical analyses; but highlights that exon exclusion, resultant from entry of a PMO, only occurs when the PMO is conjugated to CP8M.

In order to determine if CP8M hindered the biological activity of the PMO, direct intramuscular administrations (2.2 nmol) were conducted into the Tibialis anterior muscle of mdx female mice, with muscle recovered 7 days post-administration. The percentage of dystrophin re-expression was equivocal between the PMO-CP8M (805.75) and the naked PMO (762.25) with no statistical significant difference (n=4, p=0.863; FIG. 15 and FIG. 16). Thus it was determined that CP8M does not confer any steric hindrance to the biological activity of the PMO.

Systemic administrations of PMO-CP8M and PMO were conducted in mdx mice to determine if the CP8M moiety enhanced cell entry into skeletal muscle. Varying suboptimal amounts (totally 1 μmol/kg, 4.4 μmol/kg, 10.9 μmol/kg) were administered by either intraperitoneal or intravenous injections, and diaphragm and/or Tibialis anterior (TA) muscle recovered 7 days post-administration. After a single intraperitoneal administration of 1 μmol/kg the diaphragm muscle gave more dystrophin positive fibres after PMO-CP8M treatment compared to the PMO control group (FIG. 17a, n=1). In tibialis anterior muscles, intravenous (4.4 μmol/kg; n=3) data was equivocal between groups (FIG. 17b and FIG. 17d, p=0.201), as was the intraperitoneal (10.9 μmol/kg; n=4) data (FIG. 17c and FIG. 17d, p=0.886).

(4.4 μmol/kg; n=3) data was equivocal between group (FIG. 17b and FIG. 17d, p=0.201), as was the intraperitoneal (10.9 μmol/kg; n=4) data (FIG. 17c and FIG. 17d, p=0.886).

Systemic intraperitoneal administrations of PMO-CP8M and PMO were conducted in mdx mice to determine if CP8M enhanced cell entry (FIGS. 18-21). A series of tissues was recovered and frozen 1 or 2 weeks post-administration (skeletal muscle, heart, brain and liver).

A single low dose of PMO or PMO-CP8M (1 μmol/kg) was administered (n=1 per group) and tissues recovered 7 days post-administration. Dystrophin-positive heart muscle fibres were detected after PMO-CPM8, but not PMO administration (FIG. 18a).

In addition, we carried out repeated intraperitoneal administrations into mdx mice. Intraperitoneal injections of PMO-CP8M (without fluorescent label) totaling 7.6 μmol/kg over 4 days (n=4 per group) lead to a significant increase in dystrophin-positive heart muscle fibres 2 weeks post-administration compared to injection of an equimolar amount of PMO (340±69 vs 57±17 fibres, p<0.01; FIGS. 18b & 18d).

Furthermore, Applicant carried out intraperitoneal administration of PMO or PMO-CP8M, totalling 10.9 μmol/kg over 2 days (n=4 per group). Again, administration of PMO-CP8M lead to a significantly higher number of dystrophin-positive heart muscle fibres compared to administration of PMO (680±163 vs 33±8 fibres, p<0.05; FIGS. 18c & 18e).

PMO-peptide conjugates of both 8.7 kDa and 9.2 kDa were successfully delivered to heart muscle fibres as evidenced by the induction of dystrophin re-expression in the hearts of mdx mice (FIG. 19, n=4).

A single low dose (1 μmol/kg) intravenous administration of PMO-CP8M, but not PMO (both without fluorescent label), led to recovery of dystrophin expression in the Purkinje cells of mdx mouse cerebellum (FIG. 20; n=1 per group). No dystrophin expression was observed in the PMO control.

A single low dose (1 μmol/kg) intravenous administration of PMO-HP8M led to increased hepatocyte fluorescence in the vicinity of blood vessels two weeks post-administration compared to administration of PMO (FIG. 21; n=1 per group), implying increased uptake of PMO-HP8M in hepatocytes.

Conclusion

From the data generated it can be seen that the conjugation of a CPA, stabilized by stapling, to a BAC (in the form of a PMO), via a BFL, facilitates entry of the PMO into a cell. The StaP CPA facilitated PMO entry in both in vitro and in vivo assay systems.

Applicant's data presents evidence that modified linker systems based on HNA and 4 formyl benzioic acid improve the efficiency of conjugation between a BAC and CPA.

Surprisingly, variants of CPA in which the formal charge is reduced demonstrate enhanced cell entry at lower concentrations. This will have important sequelae with respect to improving the toxicological profile of CPA, more specifically a CPP.

The in vivo model of RNA splicing suppression demonstrated that the biological action of an α-helical peptide conjugated PMO is equivalent to naked PMO following intramuscular administration, thus determining that no steric hindrance is exerted upon the PMO when coupled to an α-helical peptide moiety.

The data demonstrates the fact that in the in vivo model of RNA splicing suppression the stabilized CPA may enhance cell entry into skeletal muscle, particularly at lower doses. However PMO are known to enter skeletal muscle without a CPP conjugation.

Surprisingly, and very significantly, it has been demonstrated that tissues refractory to naked PMO transfection re-express dystrophin protein in both the heart and brain (purkinje cell) compartments when the PMO is conjugated with a StaP.

Applicant further provides evidence that the CPP can facilitate the entry of cargoes of different size and mass far beyond that stated in the current state of the art.

The repertoire of human and animal diseases that can be addressed is now expanded and enhanced due to the increased pharmacodynamics of the PMOs when conjugated with a stabilised peptide. Neuromuscular disease, metabolic disease, cancer, age-related degenerative diseases and acquired viral infection can all be targeted.

REFERENCES

1 Iversen, P. L. et al. Discovery and early development of AVI-7537 and AVI-7288 for the treatment of Ebola virus and Marburg virus infections. *Viruses* 4, 2806-2830, doi: 10.3390/v4112806 (2012).

2 Heald, A. E. et al. Safety and pharmacokinetic profiles of phosphorodiamidate morpholino oligomers with activity against ebola virus and marburg virus: results of two single-ascending-dose studies. *Antimicrob Agents Chemother* 58, 6639-6647, doi:10.1128/aac.03442-14 (2014).

3 Warren, T. K. et al. Advanced antisense therapies for postexposure protection against lethal filovirus infections. *Nat Med* 16, 991-994, doi:10.1038/nm.2202 (2010).

4 Campbell, J. M., Bacon, T. A. & Wickstrom, E. Oligodeoxynucleoside phosphorothioate stability in subcellular extracts, culture media, sera and cerebrospinal fluid. *Journal of biochemical and biophysical methods* 20, 259-267 (1990).

5 Agrawal, S., Mayrand, S. H., Zamecnik, P. C. & Pederson, T. Site-specific excision from RNA by RNase H and mixed-phosphate-backbone oligodeoxynucleotides. *Proc Natl Acad Sci USA* 87, 1401-1405 (1990).

6 Tereshko, V. et al. Correlating structure and stability of DNA duplexes with incorporated 2'-O-modified RNA analogues. *Biochemistry* 37, 10626-10634, doi:10.1021/bi980392a (1998).

7 Shibahara, S. et al. Inhibition of human immunodeficiency virus (HIV-1) replication by synthetic oligo-RNA derivatives. *Nucleic Acids Res* 17, 239-252 (1989).

8 Goemans N, C. C., Kraus J E, et al. Drisapersen efficacy and safety in Duchenne muscular dystrophy: results of a phase III, randomized, double-blind, placebo-controlled trial (study DMD114044). *World Muscle Society Congress; Asilomar*, CA, USA; Oct. 1-5, 2013 (2103).

9 Goemans, N. M. et al. Long-Term Efficacy, Safety, and Pharmacokinetics of Drisapersen in Duchenne Muscular Dystrophy: Results from an Open-Label Extension Study. *PLoS One* 11, e0161955, doi:10.1371/journal.pone.0161955 (2016).

10 Dirin, M. & Winkler, J. Influence of diverse chemical modifications on the ADME characteristics and toxicology of antisense oligonucleotides. *Expert Opin Biol Ther* 13, 875-888, doi:10.1517/14712598.2013.774366 (2013).

11 Sazani, P. et al. Repeat-dose toxicology evaluation in cynomolgus monkeys of AVI-4658, a phosphorodiamidate morpholino oligomer (PMO) drug for the treatment of duchenne muscular dystrophy. *Int J Toxicol* 30, 313-321, doi:10.1177/1091581811403505 (2011).

12 Sazani, P., Weller, D. L. & Shrewsbury, S. B. Safety pharmacology and genotoxicity evaluation of AVI-4658. *Int J Toxicol* 29, 143-156, doi:10.1177/1091581809359206 (2010).

13 Mendell, J. R. et al. Eteplirsen for the treatment of Duchenne muscular dystrophy. *Ann Neurol* 74, 637-647, doi:10.1002/ana.23982 (2013).

14 Heemskerk, H. A. et al. In vivo comparison of 2'-O-methyl phosphorothioate and morpholino antisense oligonucleotides for Duchenne muscular dystrophy exon skipping. *J Gene Med* 11, 257-266, doi:10.1002/jgm.1288 [doi] (2009).

15 Kreutz, M. et al. Antibody-antigen-adjuvant conjugates enable co-delivery of antigen and adjuvant to dendritic cells in cis but only have partial targeting specificity. *PLoS One* 7, e40208, doi:10.1371/journal.pone.0040208 (2012).

16 Derossi, D., Joliot, A. H., Chassaing, G. & Prochiantz, A. The third helix of the Antennapedia homeodomain translocates through biological membranes. *J Biol Chem* 269, 10444-10450 (1994).

17 Gautam, A. et al. CPPsite: a curated database of cell penetrating peptides. *Database: the journal of biological databases and curation* 2012, bas015, doi:10.1093/database/bas015 (2012).

18 Hirose, H. et al. Transient focal membrane deformation induced by arginine-rich peptides leads to their direct penetration into cells. *Mol Ther* 20, 984-993, doi:10.1038/mt.2011.313 (2012).

19 Moulton, H. M. & Moulton, J. D. Morpholinos and their peptide conjugates: therapeutic promise and challenge for Duchenne muscular dystrophy. *Biochim Biophys Acta* 1798, 2296-2303, doi:10.1016/j.bbamem.2010.02.012 (2010).

20 Tunnemann, G. et al. Live-cell analysis of cell penetration ability and toxicity of oligo-arginines. *J Pept Sci* 14, 469-476, doi:10.1002/psc.968 (2008).

21 Chu, Q. et al. Towards understanding cell penetration by stapled peptides. *MedChemComm* 6, 111-119, doi:10.1039/C4MD00131A (2015).

22 Hilinski, G. J. et al. Stitched α-Helical Peptides via Bis Ring-Closing Metathesis. *Journal of the American Chemical Society* 136, 12314-12322, doi:10.1021/ja505141j (2014).

23 Lehto, T. et al. Cellular trafficking determines the exon skipping activity of Pip6a-PMO in mdx skeletal and cardiac muscle cells. *Nucleic Acids Res* 42, 3207-3217, doi:10.1093/nar/gkt1220 (2014).

24 Nakase, I. et al. Interaction of arginine-rich peptides with membrane-associated proteoglycans is crucial for induction of actin organization and macropinocytosis. *Biochemistry* 46, 492-501, doi:10.1021/bi0612824 (2007).

25 Chang, Y. S. et al. Stapled alpha-helical peptide drug development: a potent dual inhibitor of MDM2 and MDMX for p53-dependent cancer therapy. *Proc Natl Acad Sci U S A* 110, E3445-3454, doi:10.1073/pnas.1303002110 (2013).

26 Vitiello, L. et al. In vivo delivery of naked antisense oligos in aged mdx mice: analysis of dystrophin restoration in skeletal and cardiac muscle. *Neuromuscul Disord* 18, 597-605, doi:50960-8966(08)00141-7 [pii]10.1016/j.nmd.2008.05.011 [doi] (2008).

27 Jearawiriyapaisarn, N., Moulton, H. M., Sazani, P., Kole, R. & Willis, M. S. Long-term improvement in mdx cardiomyopathy after therapy with peptide-conjugated morpholino oligomers. *Cardiovasc Res* 85, 444-453, doi: cvp335 [pii]10.1093/cvr/cvp335 [doi] (2010).

28 Wu, B. et al. One-year treatment of morpholino antisense oligomer improves skeletal and cardiac muscle functions in dystrophic mdx mice. *Mol Ther* 19, 576-583, doi:10.1038/mt.2010.288 (2011).

29 Wu, B. et al. Effective rescue of dystrophin improves cardiac function in dystrophin-deficient mice by a modified morpholino oligomer. *Proc Natl Acad Sci USA* 105, 14814-14819, doi:0805676105 [pii]10.1073/pnas.0805676105 [doi] (2008).

30 Jearawiriyapaisarn, N. et al. Sustained dystrophin expression induced by peptide-conjugated morpholino oligomers in the muscles of mdx mice. *Mol Ther* 16, 1624-1629, doi:mt2008120 [pii]10.1038/mt.2008.120 [doi] (2008).

31 Betts, C. et al. Pip6-PMO, A New Generation of Peptide-oligonucleotide Conjugates With Improved Cardiac Exon Skipping Activity for DMD Treatment. *Molecular therapy. Nucleic acids* 1, e38, doi:10.1038/mtna.2012.30 (2012).

32 Ivanova, G. D. et al. Improved cell-penetrating peptide-PNA conjugates for splicing redirection in HeLa cells and exon skipping in mdx mouse muscle. *Nucleic Acids Res* 36, 6418-6428 (2008).

33 Mendell, J. R. et al. Evidence-based path to newborn screening for Duchenne muscular dystrophy. *Ann Neurol* 71, 304-313, doi:10.1002/ana.23528 (2012).

34 Hoffman, E. P., Brown, R. H., Jr. & Kunkel, L. M. Dystrophin: the protein product of the Duchenne muscular dystrophy locus. *Cell* 51, 919-928. (1987).

35 Monaco, A. P., Bertelson, C. J., Liechti-Gallati, S., Moser, H. & Kunkel, L. M. An explanation for the phenotypic differences between patients bearing partial deletions of the DMD locus. *Genomics* 2, 90-95 (1988).

36 Aartsma-Rus, A. et al. Therapeutic antisense-induced exon skipping in cultured muscle cells from six different DMD patients. *Hum Mol Genet* 12, 907-914 (2003).

37 Alter, J. et al. Systemic delivery of morpholino oligonucleotide restores dystrophin expression bodywide and improves dystrophic pathology. *Nat Med* 12, 175-177 (2006).

38 Kinali, M. et al. Local restoration of dystrophin expression with the morpholino oligomer AVI-4658 in Duchenne muscular dystrophy: a single-blind, placebo-controlled, dose-escalation, proof-of-concept study. *Lancet Neurol* 8, 918-928, doi:S1474-4422(09)70211-X [pii]1 0.1016/S1474-4422(09)70211-X [doi] (2009).

39 Lu, Q. L. et al. Systemic delivery of antisense oligoribonucleotide restores dystrophin expression in body-wide skeletal muscles. *Proc Natl Acad Sci USA* 102, 198-203 (2005).

40 van Deutekom, J. C. et al. Local dystrophin restoration with antisense oligonucleotide PRO051. *N Engl J Med* 357, 2677-2686, doi:357/26/2677 [pii]10.1056/NEJMoa073108 [doi] (2007).

41 Wu, B. et al. Dose-dependent restoration of dystrophin expression in cardiac muscle of dystrophic mice by systemically delivered morpholino. *Gene Ther* 17, 132-140, doi:gt2009120 [pii]1 0.1038/gt.2009.120 [doi] (2010).

42 Cirak, S. et al. Exon skipping and dystrophin restoration in patients with Duchenne muscular dystrophy after systemic phosphorodiamidate morpholino oligomer treatment: an open-label, phase 2, dose-escalation study. *Lancet* 378, 595-605, doi:10.1016/s0140-6736(11)60756-3 (2011).

---

The invention claimed is:

1. A molecule comprising:
   i. a biologically active siRNA or antisense oligonucleotide moiety, comprising a phosphorodiamidate morpholino oligonucleotide (PMO) covalently linked via a bi-functional linker moiety (BFL) to,
   ii. a peptide moiety comprising a stapled peptide (StaP) or a stitched peptide (StiP), wherein the StaP or StiP, is a stabilized peptide which has a conformation comprising at least one alpha helix by olefin cross linking comprising in the StaP an olefin cross link between two unnatural amino acids of the peptide at positions i, i+4, and/or i, i+7 and in the StiP at least two olefin cross links between at least three unnatural amino acids of the peptide at positions i, i+4, and i+11, and the StaP or the StiP can penetrate a cell membrane and has the amino acid sequence comprising SEQ ID NO: 29, 30, 35, 43, 46, 61, 92, 93, 94, 95, 96, 97, 98, 113, 120, 151, 152, 175, 176, 177, 178, 180, 181, 182, 183, or 184, and wherein the molecule can penetrate a cell membrane, and has biological activity of the oligonucleotide moiety.

2. The molecule according to claim 1, wherein the StaP or StiP comprises at least two unnatural amino acids bearing all-hydrocarbon tethers and at least one of those unnatural amino acids has an α-methyl group.

3. The molecule according to claim 1, wherein each cross link is formed by ring-closing olefin metathesis.

4. The molecule according to claim 1, wherein each cross link comprises a hydrocarbon bridge, and wherein at least one cross linked unnatural amino acid comprises an a-methyl group.

5. The molecule according to claim 1, wherein the StaP or StiP comprises at least two unnatural amino acids bearing all-hydrocarbon tethers.

6. The molecule of claim 5, wherein the StaP or StiP is stabilized by at least one cross link between the unnatural amino acid R-octenylalanine and the unnatural amino acid S-pentenylalanine.

7. The molecule according to claim 3, wherein the StaP or StiP is stabilized by at least one cross link between one or more of the unnatural amino acids: (S)-pentenylalanine (S5) or its enantiomer (R5); S-octenylalanine (S8) or its enantiomer (R8); or combinations thereof.

8. The molecule according to claim 1, wherein the StaP or StiP is stabilized by at least one cross link between one or more of the unnatural amino acids:

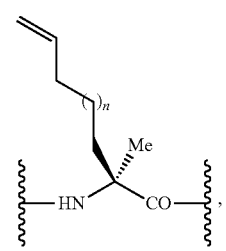

S5: n = 1
S8: n = 4

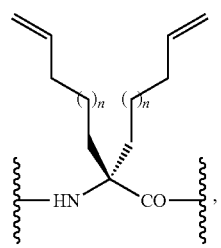

B5: n = 1
B8: n = 4

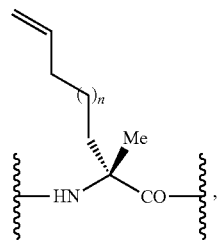

R5: n = 1
R8: n = 4

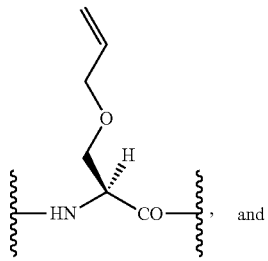

S-OAS

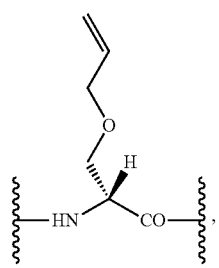

R-OAS wherein S5 is (S)-pentenylalanine, R5 is (R)-pentenylalanine, S8 is (S)-octenylalanine, R8 is (R)-octenylalanine, B5 is α,α-di-substituted pentenylalanine, B8 is α,α-di-substituted octenylalanine, and S-OAS and R-OAS are 0-allylserine analogues.

9. The molecule according to claim 5, wherein the StaP or StiP is stabilized by at least one cross link the unnatural amino acid R-octenylalanine and the unnatural amino acid R-pentenylalanine.

10. The compound according to claim 1, wherein the stabilized conformation comprises at least one beta sheet.

11. The molecule of claim 1, wherein the BFL comprises:

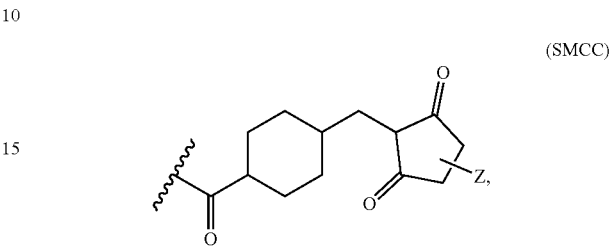

(SMCC)

a residue of succinimidyl 4-(N-maleimidomethyl) cyclohexane-l-carboxylate, where Z is

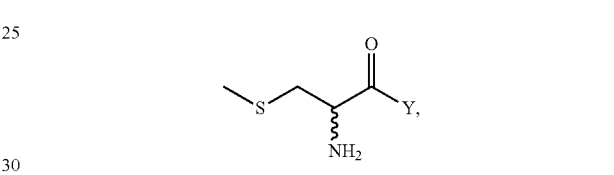

and Y is a covalent bond to the N-terminus of the StP or the StiP, or Y is

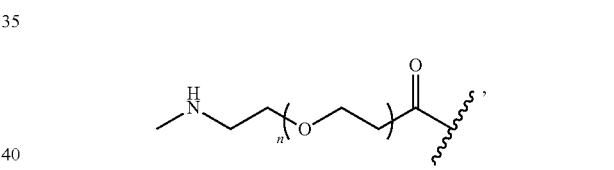

where n is 1 to 10;

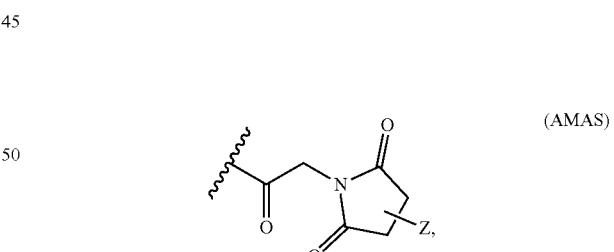

(AMAS)

a residue of N-α-maleimidoacet-oxysuccinimide ester, where Z is

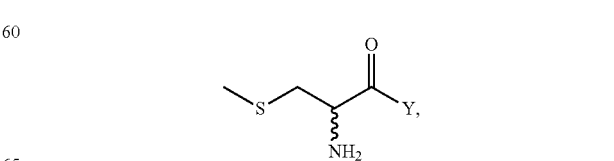

and Y is a covalent bond to the N-terminus of the StaP or the StiP, or Y is

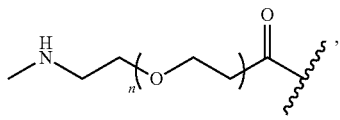

where n is 1 to 10;

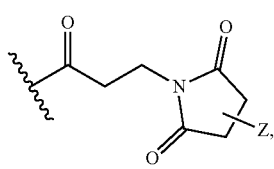
(BMPS)

a residue of N-β-maleimidopropyl-oxysuccinimide ester, where Z is

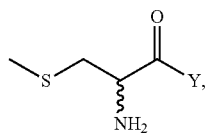

and Y is a covalent bond to the N-terminus of the StaP or the StiP, or Y is

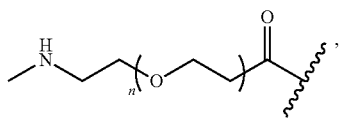

where n is 1 to 10;

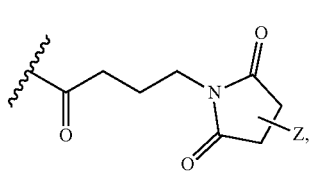
(GMBS)

a residue of N-γ-aleimidobutyryl-oxysuccinimide ester, where Z is

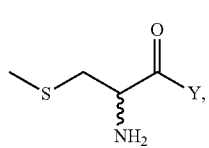

and Y is a covalent bond to the N-terminus of the StaP or the StiP, or Y is

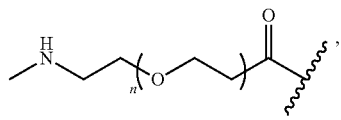

where n is 1 to 10;

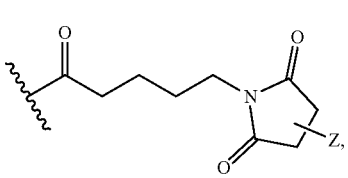
(DMVS)

a residue of N-δ-maleimidovaleryl-oxysuccinimide ester, where Z is

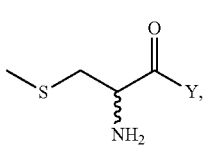

and Y is a covalent bond to the N-terminus of the StaP or the StiP, or Y is

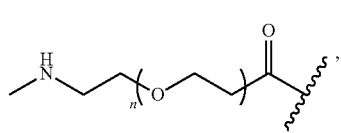

where n is 1 to 10;

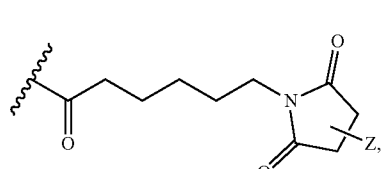
(EMCS)

a residue of N-ε-malemidocaproyl-oxysuccinimide ester, where Z is

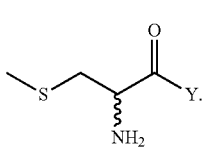

and Y is a covalent bond to the N-terminus of the StaP or the StiP, or Y is

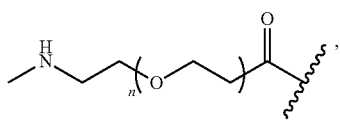

where n is 1 to 10

(LC-SMCC)

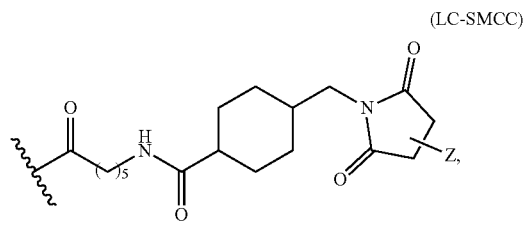

a residue of succinimidyl 4-(N-maleimidomethyl) cyclohexane-1-carboxy-(6-amidocaproate), where Z is

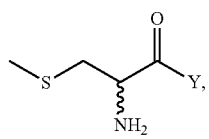

and Y is a covalent bond to the N-terminus of the StaP or the StiP, or Y is

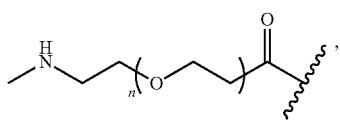

where n is 1 to 10;

(SM(PEG)$_n$)

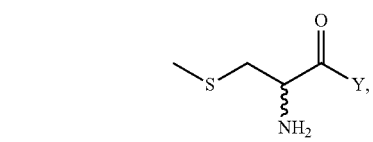

a residue of succinimidyl 4-(N-maleimidomethyl) cyclohexane-1-carboxylate (polyethylene glycol), wherein n equals 1 to 10, Z is and, Y is either present or not present, and when Y is present, Y is

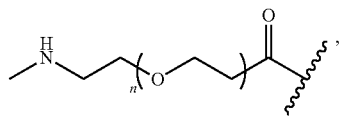

where n is 1 to 10, and when Y is not present, Y is a covalent bond to the N-terminus of the StaP or the StiP;

(DGS)

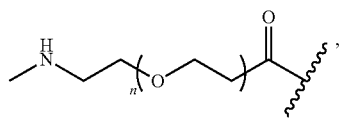

a residue of disuccinimidyl gluterate, where Z is not present, and instead there is a covalent bond to the N-terminus of the StaP or the StiP, or to the N of

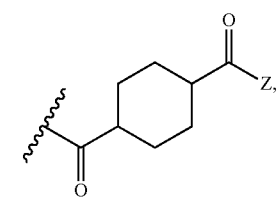

wherein n is 1 to 10; or, (DSCDS)

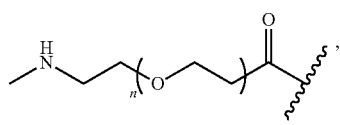

a residue of disuccinimidyl-cyclohexl-1,4-diester, where Z is not present, and instead there is a covalent bond to the N-terminus of the StaP or the StiP, or to the N of

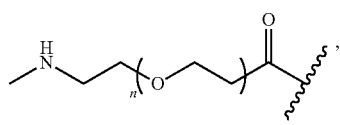

wherein n is 1 to 10.

12. The molecule of claim 11, wherein in each Y moiety, n is 5.

13. The molecule of claim 11, wherein the BFL comprises SMCC.

14. The molecule of claim 1, wherein the BFL comprises:

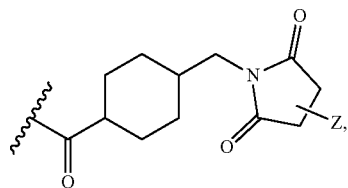

a residue of succinimidyl 4-(N-maleimidomethyl) cyclohexane-1-carboxylate, where Z is

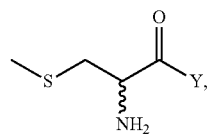

and Y is a covalent bond to the N-terminus of the StaP or the StiP;

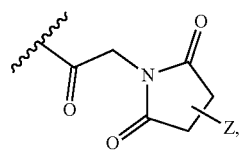

a residue of N-a-maleimidoacet-oxysuccinimide ester, where Z is

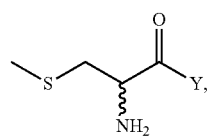

and Y is a covalent bond to the N-terminus of the StaP or the StiP;

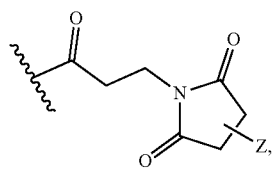

a residue of N-β-maleimidopropyl-oxysuccinimide ester, where Z is

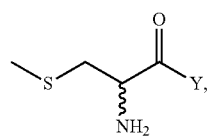

and Y is a covalent bond to the N-terminus of the StaP or the StiP;

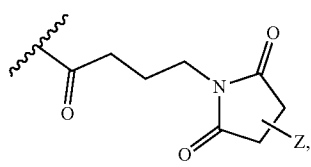

a residue of N-γ-aleimidobutyryl-oxysuccinimide ester, where Z is

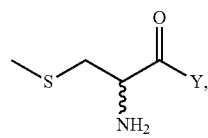

and Y is a covalent bond to the N-terminus of the StaP or the StiP;

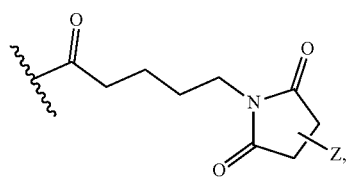

a residue of N-δ-maleimidovaleryl-oxysuccinimide ester, where Z is

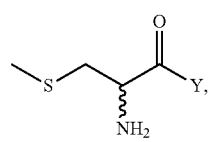

and Y is a covalent bond to the N-terminus of the StaP or the StiP;

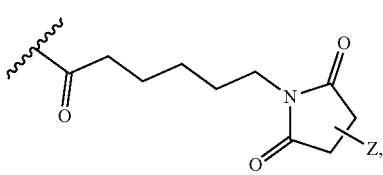

a residue of N-ϵc-malemidocaproyl-oxysuccinimide ester, where Z is

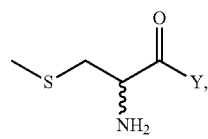

and Y is a covalent bond to the N-terminus of the StaP or the StiP;

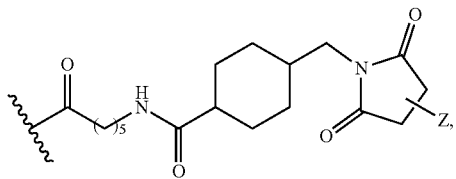

a residue of succinimidyl 4-(N-maleimidomethyl) cyclohexane-1-carboxy-(6-amidocaproate), where Z is

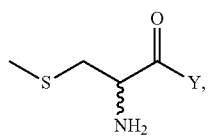

and Y is a covalent bond to the N-terminus of the StaP or the StiP;

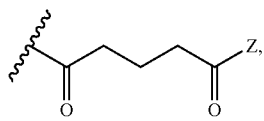

a residue of disuccinimidyl gluterate, where Z is not present;
or,

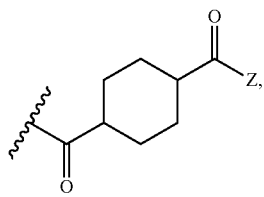

a residue of disuccinimidyl-cyclohexl-1,4-diester, where Z is not present.

15. The molecule of claim 12, wherein the BFL comprises SMCC.

16. The molecule of claim 15, wherein the oligonucleotide comprises 5'CUCCAACAUCAAGGAAGAUGG-CAUUUCUAG3' (SEQ ID NO:2).

17. The molecule of claim 1, wherein the oligonucleotide comprises 5'CUCCAACAUCAAGGAAGAUGG-CAUUUCUAG3' (SEQ ID NO:2).

18. The molecule of claim 1 wherein the StaP or the StiP has the amino acid sequence comprising SEQ ID NO: 43, 46, 61, 92, 93, 94, 95, 96, 97, 98, 151 or 152.

19. The molecule of claim 17, wherein the StiP or StaP comprises pentenylalanine.

20. The molecule of claim 16, wherein the StiP or StaP comprises pentenylalanine.

21. The molecule according to claim 1, wherein the BFL comprises a residue of an amine to sulphydryl cross linker containing N-hydroxysuccinimide esters and malemide reactive groups separated by a cyclohexane spacer.

22. The molecule according to claim 1, wherein the oligonucleotide moiety comprises RNA.

23. The molecule according to claim 19, wherein the BFL comprises a residue of succinimidyl 4-(N-maleimidomethyl) cyclohexane-1-carboxylate (SMCC).

24. The molecule of claim 21, wherein the oligonucleotide comprises 5'CUCCAACAUCAAGGAAGAUGG-CAUUUCUAG3' (SEQ ID NO:2).

25. A composition comprising the molecule according to claim 1 and one or more pharmaceutically acceptable excipients.

26. The molecule of claim 18 wherein the oligonucleotide comprises SEQ ID NO:1 or SEQ ID NO:2, and StaP or the StiP has the amino acid sequence comprising SEQ ID NO: 61.

27. A composition comprising the molecule according to claim 17 and one or more pharmaceutically acceptable excipients.

28. A composition comprising the molecule according to claim 18 and one or more pharmaceutically acceptable excipients.

29. A composition comprising the molecule according to claim 23 and one or more pharmaceutically acceptable excipients.

30. The composition of claim 29, formulated for oral, parenteral, intravenous, or topical administration.

* * * * *